US012130290B2

(12) United States Patent
Walt et al.

(10) Patent No.: US 12,130,290 B2
(45) Date of Patent: Oct. 29, 2024

(54) COMPOSITIONS AND METHODS FOR DIAGNOSING BREAST CANCER

(71) Applicant: TRUSTEES OF TUFTS COLLEGE, Medford, MA (US)

(72) Inventors: David R. Walt, Medford, MA (US); Shazia Baig, Medford, MA (US); Stephanie Schubert, Medford, MA (US)

(73) Assignee: Trustees of Tufts College, Medford, MA (US)

(*) Notice: Subject to any disclaimer, the term of this patent is extended or adjusted under 35 U.S.C. 154(b) by 1182 days.

(21) Appl. No.: 15/824,761

(22) Filed: Nov. 28, 2017

(65) Prior Publication Data
US 2018/0149653 A1 May 31, 2018

Related U.S. Application Data

(60) Provisional application No. 62/427,663, filed on Nov. 29, 2016.

(51) Int. Cl.
G01N 33/53 (2006.01)
G01N 33/574 (2006.01)

(52) U.S. Cl.
CPC ... *G01N 33/57415* (2013.01); *G01N 2333/46* (2013.01); *G01N 2333/4703* (2013.01); *G01N 2333/475* (2013.01); *G01N 2333/71* (2013.01); *G01N 2333/723* (2013.01)

(58) Field of Classification Search
CPC ......... G01N 33/57415; G01N 2333/46; G01N 2333/475; G01N 2333/723; G01N 2333/71; G01N 2333/4703
See application file for complete search history.

(56) References Cited

U.S. PATENT DOCUMENTS

| 5,837,832 | A | 11/1998 | Chee et al. |
|---|---|---|---|
| 6,436,665 | B1 | 8/2002 | Kuimelis |
| 8,222,047 | B2 | 7/2012 | Duffy et al. |
| 8,236,574 | B2 | 8/2012 | Duffy et al. |
| 8,415,171 | B2 | 4/2013 | Rissin et al. |
| 8,846,415 | B2 | 9/2014 | Duffy et al. |
| 9,110,025 | B2 | 8/2015 | Rissin et al. |
| 9,310,360 | B2 | 4/2016 | Duffy et al. |
| 9,482,662 | B2 | 11/2016 | Duffy et al. |
| 2005/0118574 | A1 | 6/2005 | Chandler et al. |
| 2007/0269345 | A1 | 11/2007 | Schilffarth et al. |
| 2009/0170214 | A1 | 7/2009 | Meek et al. |
| 2010/0075355 | A1 | 3/2010 | Duffy et al. |
| 2010/0075407 | A1 | 3/2010 | Duffy et al. |
| 2010/0075439 | A1 | 3/2010 | Duffy et al. |
| 2010/0075862 | A1 | 3/2010 | Duffy et al. |
| 2010/0178709 | A1 | 7/2010 | Chandler et al. |
| 2010/0329929 | A1 | 12/2010 | Goix et al. |
| 2011/0212462 | A1 | 9/2011 | Duffy et al. |
| 2011/0212848 | A1* | 9/2011 | Duffy ............... G01N 33/54306 506/9 |
| 2012/0040863 | A1* | 2/2012 | Wang .................. C12Q 1/6886 506/9 |
| 2012/0312085 | A1 | 12/2012 | Schilffarth |
| 2013/0059400 | A1 | 3/2013 | Livingston |
| 2013/0261009 | A1 | 10/2013 | Goix et al. |
| 2014/0042366 | A1 | 2/2014 | Chandler et al. |
| 2014/0243223 | A1 | 8/2014 | Duffy et al. |
| 2014/0342468 | A1 | 11/2014 | Todd et al. |
| 2015/0353997 | A1 | 12/2015 | Duffy et al. |
| 2015/0355182 | A1 | 12/2015 | Rissin et al. |
| 2016/0101421 | A1 | 4/2016 | Ching et al. |
| 2016/0123969 | A1 | 5/2016 | Rissin et al. |
| 2016/0266103 | A1 | 9/2016 | Chandler et al. |

OTHER PUBLICATIONS

Wilson et al (Journal of Laboratory Automation, 2016, vol. 21(4) 533-547.*
Rissin et al (Lab Chip, 2013, 13, 2902-2911).*
Wei et al (Xiandai Shengwuyixue Jinzhan, 2011 Volume: 11, Issue: 9, pp. 1754-1756, Abstract.*
Bae et al (BMC Cancer (2015) 15:138).*
Xie et al (JBC; 2001, vol. 276, No. 17, Issue of Apr. 27, pp. 14187-14194).*
Ge, Hui, "UPA, a universal protein array system for quantitative detection of protein-protein, protein-DNA, protein-RNA and protein-ligand interactions," Nucleic Acids Research, Jan. 2000, vol. 28, No. 2, e3, pp. i-vii (7 pages).
Heller et al., "Discovery and analysis of inflammatory disease-related genes using cDNA microarrays," Proceedings of the National Academy of Sciences (USA), Mar. 1997, vol. 94, No. 6, pp. 2150-2155 (6 pages).
Lockhart et al. "Expression monitoring by hybridization to high-density oligonucleotide arrays," Nature Biotechnology, Dec. 1996, vol. 14, No. 13, pp. 1675-1680 (6 pages).
MacBeath et al., "Printing Proteins as Microarrays for High-Throughput Function Determination," Science, 2000, vol. 289, Iss. 5485, pp. 1760-1763 (5 pages).
Samy et al., "Prognostic significance of serum Her2/neu, BCL2, CA15-3 and CEA in breast cancer patients: A short follow-up," Cancer Biomarkers, 2010, vol. 6, No. 2, pp. 63-72 (11 pages).

(Continued)

*Primary Examiner* — Carmencita M Belei
(74) *Attorney, Agent, or Firm* — Melissa Hunter-Ensor; Leslie Serunian; Greenberg Traurig, LLP

(57) ABSTRACT

The invention provides methods and compositions for distinguishing breast cancer.

4 Claims, 13 Drawing Sheets
Specification includes a Sequence Listing.

(56) References Cited

OTHER PUBLICATIONS

Schena et al., "Parallel human genome analysis: microarray-based expression monitoring of 1000 genes," Proceedings of the National Academy of Sciences (USA), Oct. 1996, vol. 93, No. 20, pp. 10614-10619 (6 pages).

Zhang et al., "Expression and Significance of ER, PR, VEGF, CA15-3, CA125 and CEA in Judging the Prognosis of Breast Cancer," Asian Pacific Journal of Cancer Prevention, 2013, vol. 14, No. 6, pp. 3937-3940 (4 pages).

Zhu et al., "Analysis of yeast protein kinases using protein chips," Nature Genetics, Nov. 2000, vol. 26, No. 3, pp. 283-289 (8 pages).

\* cited by examiner

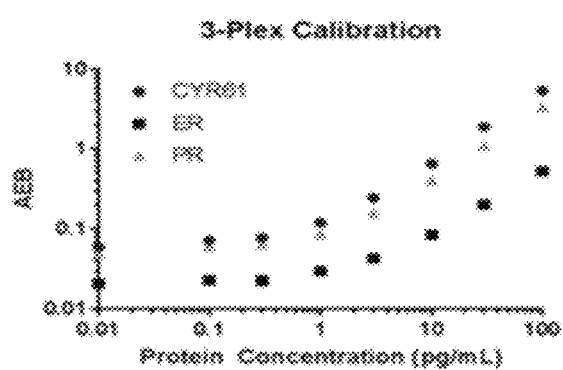
FIG. 1A
FIG. 1B
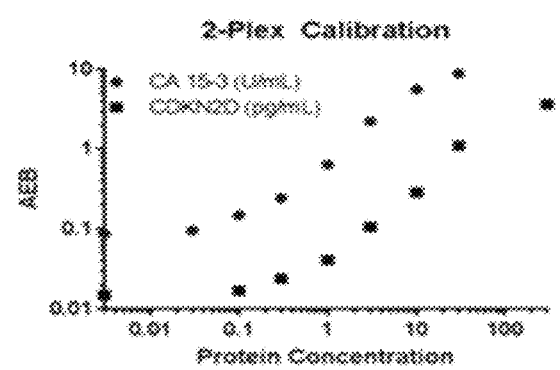
FIG. 1C
FIG. 1D
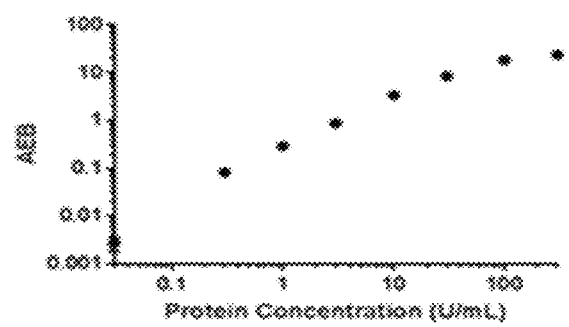

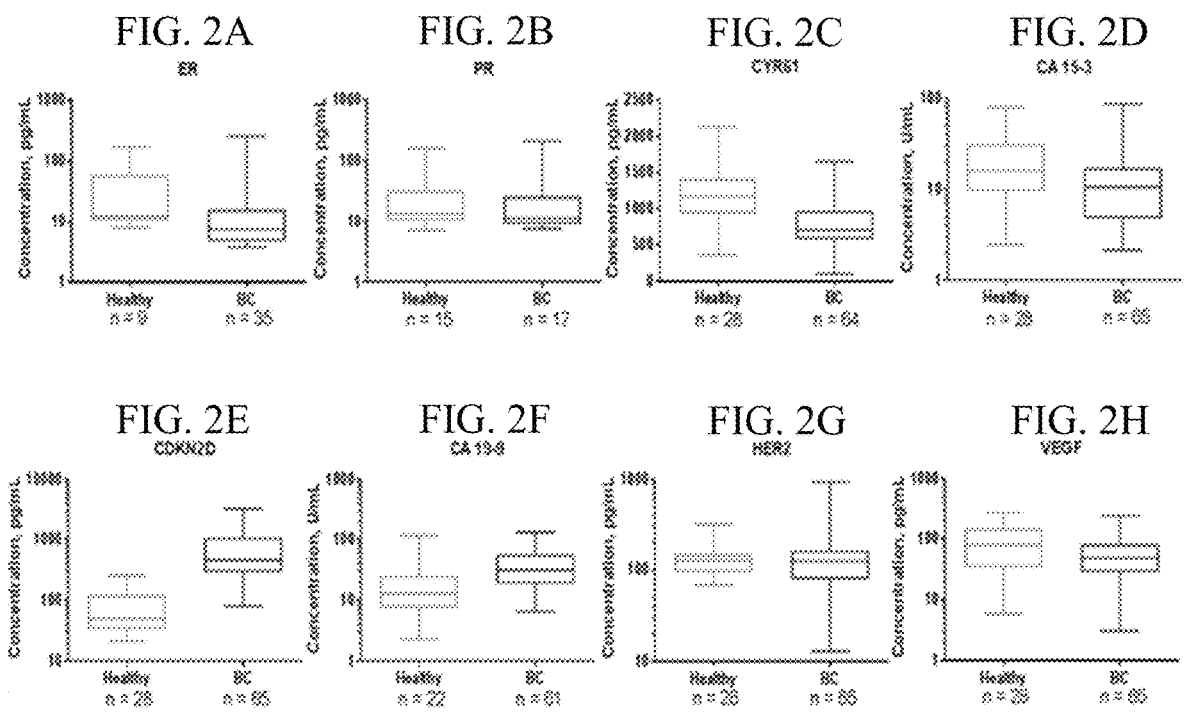

Digital ELISA – as shown in the art

FIG. 11A
FIG. 11B
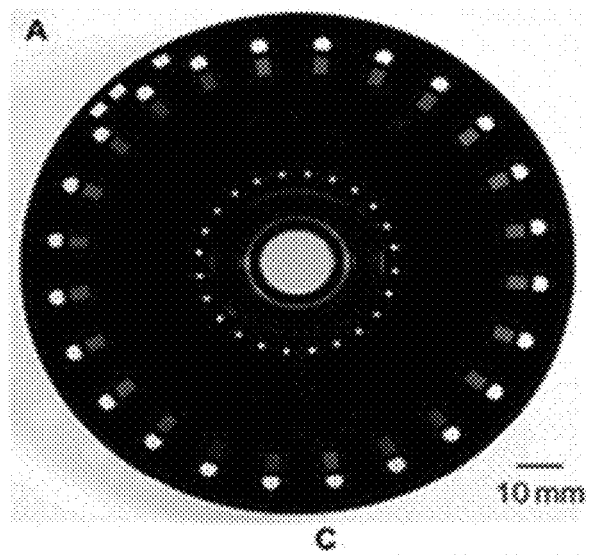
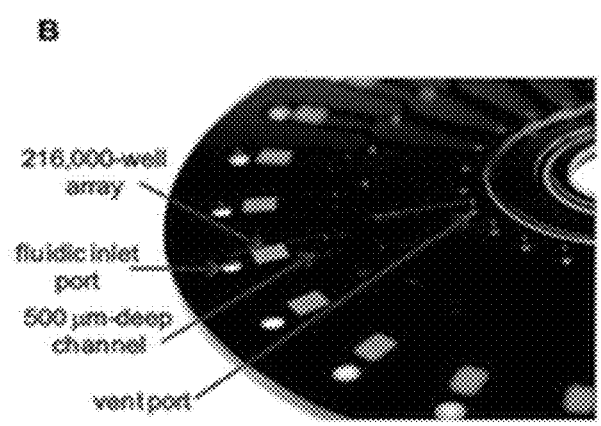
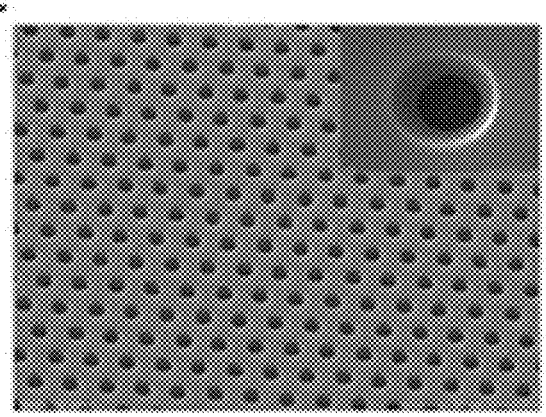
FIG. 11C
Simoa Disc – as shown in the art

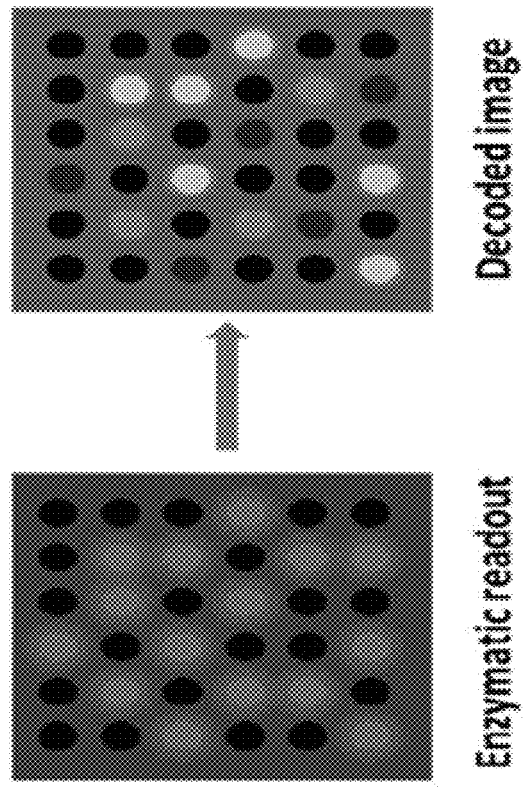
FIG. 12B
FIG. 12A
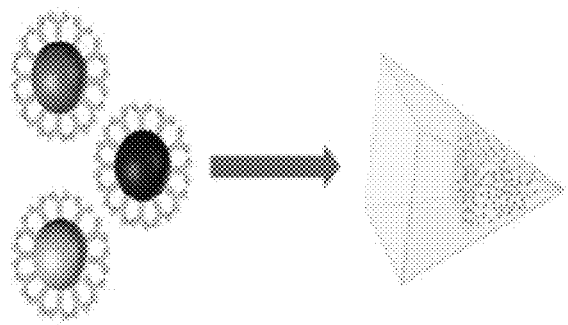
Multiplex Simoa Assay Scheme and Illustration of Enzymatic Readout as known in the art

SEQUENCE LISTING

<160> NUMBER OF SEQ ID NOS: 15

<210> SEQ ID NO 1
<211> LENGTH: 273
<212> TYPE: PRT
<213> ORGANISM: Homo sapiens

<400> SEQUENCE: 1

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Leu Ser Thr Gly Val Ser Phe Phe Phe Leu Ser
        50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
                85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
        195                 200                 205

Tyr Gly Gln Leu Asp Ile Phe Pro Ala Arg Asp Thr Tyr His Pro Met
    210                 215                 220
```

```
Ser Glu Tyr Pro Thr Tyr His Thr His Gly Arg Tyr Val Pro Pro Ser
225                 230                 235                 240

Ser Thr Asp Arg Ser Pro Tyr Glu Lys Val Ser Ala Gly Asn Gly Gly
            245                 250                 255

Ser Ser Leu Ser Tyr Thr Asn Pro Ala Val Ala Ala Thr Ser Ala Asn
            260                 265                 270

Leu

<210> SEQ ID NO 2
<211> LENGTH: 1220
<212> TYPE: DNA
<213> ORGANISM: Homo sapiens

<400> SEQUENCE: 2
cgctccacct ctcaagcagc cagcgcctgc ctgaatctgt tctgccccct ccccacccat      60
ttcaccacca ccatgacacc gggcacccag tctcctttct tcctgctgct gctcctcaca     120
gtgcttacag ttgttacggg ttctggtcat gcaagctcta ccccaggtgg agaaaaggag     180
acttcggcta cccagagaag ttcagtgccc agctctactg agaagaatgc tttgtctact     240
ggggtctctt tcttttttcct gtcttttcac atttcaaacc tccagtttaa ttcctctctg     300
gaagatccca gcaccgacta ctaccaagag ctgcagagag acatttctga aatgttttg     360 cagatttata acaagggggg ttttctgggc ctctccaata ttaagttcag gccaggatct     420
gtggtggtac aattgactct ggccttccga gaaggtacca tcaatgtcca cgacgtggag     480
acacagttca atcagtataa aacggaagca gcctctcgat ataacctgac gatctcagac     540
gtcagcgtga gtgatgtgcc atttcctttc tctgcccagt ctggggctgg ggtgccaggc     600
tggggcatcg cgctgctggt gctggtctgt gttctggttg cgctggccat tgtctatctc     660
attgccttgg ctgtctgtca gtgccgccga aagaactacg gcagctgga catctttcca     720 gcccgggata cctaccatcc tatgagcgag taccccacct accacaccca tgggcgctat     780 gtgccccta gcagtaccga tcgtagcccc tatgagaagg tttctgcagg taatggtggc     840
agcagcctct cttacacaaa cccagcagtg gcagccactt ctgccaactt gtaggggcac     900
gtcgcccgct gagctgagtg gccagccagt gccattccac tccactcagg ttcttcaggg     960
ccagagcccc tgcaccctgt ttgggctggt gagctgggag ttcaggtggg ctgctcacag    1020
cctccttcag aggccccacc aatttctcgg acacttctca gtgtgtggaa gctcatgtgg    1080 gccctgagg gctcatgcct gggaagtgtt gtggtggggg ctcccaggag gactggccca    1140
gagagccctg agatagcggg gatcctgaac tggactgaat aaaacgtggt ctcccactgc    1200
gccaaaaaaa aaaaaaaaa                                                 1220

<210> SEQ ID NO 3
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly His His His His His His Ser Gly Ser Glu Phe Arg Val Ser
1               5                   10                  15

Arg Asp Asp Ala Thr Gly Ser Pro Arg Ala Pro Ser Gly Ser Ser Arg
            20                  25                  30

Gln Asp Thr Thr Pro Thr Arg Pro Thr Leu Leu Ile Leu Leu Trp Thr
```

```
                35                  40                  45
Trp Pro Phe His Ile Pro Val Ala Leu Ser Arg Cys Ser Glu Met Val
 50                  55                  60
Pro Gly Thr Ala Asp Cys His Ile Thr Ala Asp Arg Lys Val Tyr Pro
 65                  70                  75                  80
Gln Ala Asp Thr Val Ile Val His His Trp Asp Ile Met Ser Asn Pro
                 85                  90                  95
Lys Ser Arg Leu Pro Pro Ser Pro Arg Pro Gln Gly Gln Arg Trp Ile
                100                 105                 110
Trp Phe Asn Leu Glu Pro Pro Asn Cys Gln His Leu Glu Ala Leu
                115                 120                 125
Asp Arg Tyr Phe Asn Leu Thr Met Ser Tyr Arg Ser Asp Ser Asp Ile
130                 135                 140
Phe Thr Pro Tyr Gly Trp Leu Glu Pro Trp Ser Gly Pro Ala His
145                 150                 155                 160
Pro Pro Leu Asn Leu Ser Ala Lys Thr Glu Leu Val Ala Trp Ala Val
                165                 170                 175
Ser Asn Trp Lys Pro Asp Ser Ala Arg Val Arg Tyr Tyr Gln Ser Leu
                180                 185                 190
Gln Ala His Leu Lys Val Asp Val Tyr Gly Arg Ser His Lys Pro Leu
                195                 200                 205
Pro Lys Gly Thr Met Met Glu Thr Leu Ser Arg Tyr Lys Phe Tyr Leu
210                 215                 220
Ala Phe Glu Asn Ser Leu His Pro Asp Tyr Ile Thr Glu Lys Leu Trp
225                 230                 235                 240
Arg Asn Ala Leu Glu Ala Trp Ala Val Pro Val Val Leu Gly Pro Ser
                245                 250                 255
Arg Ser Asn Tyr Glu Arg Phe Leu Pro Pro Asp Ala Phe Ile His Val
                260                 265                 270
Asp Asp Phe Gln Ser Pro Lys Asp Leu Ala Arg Tyr Leu Gln Glu Leu
                275                 280                 285
Asp Lys Asp His Ala Arg Tyr Leu Ser Tyr Phe Arg
                290                 295                 300

<210> SEQ ID NO 4
<211> LENGTH: 381
<212> TYPE: PRT
<213> ORGANISM: Homo sapiens

<400> SEQUENCE: 4

Met Ser Ser Arg Ile Ala Arg Ala Leu Ala Leu Val Val Thr Leu Leu
 1                5                  10                  15
His Leu Thr Arg Leu Ala Leu Ser Thr Cys Pro Ala Ala Cys His Cys
                 20                  25                  30
Pro Leu Glu Ala Pro Lys Cys Ala Pro Gly Val Gly Leu Val Arg Asp
                 35                  40                  45
Gly Cys Gly Cys Cys Lys Val Cys Ala Lys Gln Leu Asn Glu Asp Cys
 50                  55                  60
Ser Lys Thr Gln Pro Cys Asp His Thr Lys Gly Leu Glu Cys Asn Phe
 65                  70                  75                  80
Gly Ala Ser Ser Thr Ala Leu Lys Gly Ile Cys Arg Ala Gln Ser Glu
                 85                  90                  95
Gly Arg Pro Cys Glu Tyr Asn Ser Arg Ile Tyr Gln Asn Gly Glu Ser
                100                 105                 110
```

```
Phe Gln Pro Asn Cys Lys His Gln Cys Thr Cys Ile Asp Gly Ala Val
            115                 120                 125
Gly Cys Ile Pro Leu Cys Pro Gln Glu Leu Ser Leu Pro Asn Leu Gly
        130                 135                 140
Cys Pro Asn Pro Arg Leu Val Lys Val Thr Gly Gln Cys Cys Glu Glu
145                 150                 155                 160
Trp Val Cys Asp Glu Asp Ser Ile Lys Asp Pro Met Glu Asp Gln Asp
                165                 170                 175
Gly Leu Leu Gly Lys Glu Leu Gly Phe Asp Ala Ser Glu Val Glu Leu
            180                 185                 190
Thr Arg Asn Asn Glu Leu Ile Ala Val Gly Lys Gly Ser Ser Leu Lys
        195                 200                 205
Arg Leu Pro Val Phe Gly Met Glu Pro Arg Ile Leu Tyr Asn Pro Leu
210                 215                 220
Gln Gly Gln Lys Cys Ile Val Gln Thr Thr Ser Trp Ser Gln Cys Ser
225                 230                 235                 240
Lys Thr Cys Gly Thr Gly Ile Ser Thr Arg Val Thr Asn Asp Asn Pro
                245                 250                 255
Glu Cys Arg Leu Val Lys Glu Thr Arg Ile Cys Glu Val Arg Pro Cys
            260                 265                 270
Gly Gln Pro Val Tyr Ser Ser Leu Lys Lys Gly Lys Lys Cys Ser Lys
        275                 280                 285
Thr Lys Lys Ser Pro Glu Pro Val Arg Phe Thr Tyr Ala Gly Cys Leu
        290                 295                 300
Ser Val Lys Lys Tyr Arg Pro Lys Tyr Cys Gly Ser Cys Val Asp Gly
305                 310                 315                 320
Arg Cys Cys Thr Pro Gln Leu Thr Arg Thr Val Lys Met Arg Phe Arg
                325                 330                 335
Cys Glu Asp Gly Glu Thr Phe Ser Lys Asn Val Met Met Ile Gln Ser
            340                 345                 350
Cys Lys Cys Asn Tyr Asn Cys Pro His Ala Asn Glu Ala Ala Phe Pro
        355                 360                 365
Phe Tyr Arg Leu Phe Asn Asp Ile His Lys Phe Arg Asp
370                 375                 380

<210> SEQ ID NO 5
<211> LENGTH: 2295
<212> TYPE: DNA
<213> ORGANISM: Homo sapiens

<400> SEQUENCE: 5
agaccgcgag cgagagcgcc cccgagcagc gcccgcgccc tccgcgcctt ctccgccggg      60
acctcgagcg aaagacgccc gccgccgcc cagccctcgc ctccctgccc accgggccca     120
ccgcgccgcc accccgaccc cgctgcgcac ggcctgtccg ctgcacacca gcttgttggc     180
gtcttcgtcg ccgcgctcgc cccgggctac tcctgcgcgc acaatgagc tcccgcatcg     240
ccagggcgct cgccttagtc gtcacccttc tccacttgac caggctggcg ctctccacct     300
gccccgctgc ctgccactgc cccctggagg cgcccaagtg cgcgccggga gtcgggctgg     360
tccgggacgt ctgcggctgc tgtaaggtct gcgccaagca gctcaacgag gactgcagca     420
aaacgcagcc ctgcgaccac accaaggggc tggaatgcaa cttcggcgcc agctccaccg     480
ctctgaaggg gatctgcaga gctcagtcag agggcagacc ctgtgaatat aactccagaa     540
tctaccaaaa cggggaaagt ttccagccca actgtaaaca tcagtgcaca tgtattgatg     600
```

```
gcgccgtggg ctgcattcct ctgtgtcccc aagaactatc tctccccaac ttgggctgtc      660
ccaaccctcg gctggtcaaa gttaccgggc agtgctgcga ggagtgggtc tgtgacgagg      720
atagtatcaa ggaccccatg gaggaccagg acggcctcct tggcaaggag ctgggattcg      780
atgcctccga ggtggagttg acgagaaaca atgaattgat gcagttggaa aaggcagct      840 cactgaagcg gctccctgtt tttggaatgg agcctcgcat cctatacaac cctttacaag      900
gccagaaatg tattgttcaa caacttcat ggtcccagtg ctcaaagacc tgtgaactg        960 gtatctccac acgagttacc aatgacaacc ctgagtgccg ccttgtgaaa gaaacccgga     1020
tttgtgaggt gcggccttgt ggacagccag tgtacagcag cctgaaaaag gcaagaaat     1080 gcagcaagac caagaaatcc cccgaaccag tcaggtttac ttacgctgga tgtttgagtg     1140
tgaagaaata ccggcccaag tactgcggtt cctgcgtgga cggccgatgc tgcacgcccc     1200
agctgaccag gactgtgaag atgcggttcc gctgcgaaga tggggagaca ttttccaaga     1260
acgtcatgat gatccagtcc tgcaaatgca actacaactg cccgcatgcc aatgaagcag     1320
cgtttcccct ctacaggctg ttcaatgaca ttcacaaatt tagggactaa atgctacctg     1380
ggtttccagg gcacacctag acaaacaagg gagaagagtg tcagaatcag aatcatggag     1440
aaaatgggcg ggggtggtgt gggtgatggg actcattgta gaaggaagc cttgctcatt      1500 cttgaggagc attaaggtat ttcgaaactg ccaagggtgc tggtgcggat ggacactaat     1560
gcagccacga ttggagaata ctttgcttca gtattggga gcacatgtta ctgcttcatt      1620
ttggagcttg tggagttgat gactttctgt tttctgtttg taaattattt gctaagcata     1680
ttttctctag gcttttttcc ttttgggagtt ctacagtcgt aaaagagata ataagattag    1740
ttggacagtt taaagctttt attcgtcctt tgacaaaagt aaatgggagg gcattccatc     1800
ccttcctgaa gggggacact ccatgagtgt ctgtgagagg cagctatctg cactctaaac    1860
tgcaaacaga aatcaggtgt tttaagactg aatgttttat ttatcaaaat gtagcttttg     1920 gggaggggagg ggaaatgtaa tactggaata atttgtaaat gattttaatt ttatattcag   1980
tgaaaagatt ttatttatgg aattaaccat ttaataaaga aatatttacc taatatctga    2040
gtgtatgcca ttcggtattt ttagaggtgc tccaaagtca ttaggaacaa cctagctcac    2100
gtactcaatt attcaaacag gacttattgg gatacagcag tgaattaagc tattaaaata    2160
agataatgat tgcttttata ccttcagtag agaaaagtct ttgcatataa agtaatgttt    2220
aaaaaacatg tattgaacac gacattgtat gaagcacaat aaagattctg aagctaaatt    2280
tgtgatttaa gaaaa                                                     2295
```

<210> SEQ ID NO 6
<211> LENGTH: 166
<212> TYPE: PRT
<213> ORGANISM: Homo sapiens

<400> SEQUENCE: 6

Met Leu Leu Glu Glu Val Arg Ala Gly Asp Arg Leu Ser Gly Ala Ala
1               5                   10                  15

Ala Arg Gly Asp Val Gln Glu Val Arg Arg Leu Leu His Arg Glu Leu
                20                  25                  30

Val His Pro Asp Ala Leu Asn Arg Phe Gly Lys Thr Ala Leu Gln Val
            35                  40                  45

Met Met Phe Gly Ser Thr Ala Ile Ala Leu Glu Leu Leu Lys Gln Gly
        50                  55                  60

Ala Ser Pro Asn Val Gln Asp Thr Ser Gly Thr Ser Pro Val His Asp

|   |   |   |   |   |   |   |   |   |   |   |   |   |   |   |
|---|---|---|---|---|---|---|---|---|---|---|---|---|---|---|
| | | 65 | | | | 70 | | | | 75 | | | | 80 |
| Ala | Ala | Arg | Thr | Gly | Phe | Leu | Asp | Thr | Leu | Lys | Val | Leu | Val | Glu | His |
| | | | | | 85 | | | | | 90 | | | | | 95 |

Ala Ala Arg Thr Gly Phe Leu Asp Thr Leu Lys Val Leu Val Glu His
                85                      90                   95

Gly Ala Asp Val Asn Val Pro Asp Gly Thr Gly Ala Leu Pro Ile His
            100                 105                 110

Leu Ala Val Gln Glu Gly His Thr Ala Val Val Ser Phe Leu Ala Ala
        115                 120                 125

Glu Ser Asp Leu His Arg Arg Asp Ala Arg Gly Leu Thr Pro Leu Glu
    130                 135                 140

Leu Ala Leu Gln Arg Gly Ala Gln Asp Leu Val Asp Ile Leu Gln Gly
145                 150                 155                 160

His Met Val Ala Pro Leu
            165

<210> SEQ ID NO 7
<211> LENGTH: 1416
<212> TYPE: DNA
<213> ORGANISM: Homo sapiens

<400> SEQUENCE: 7
ggagggaggg tgagttaggg ggagacccgg cccccaaggg gcgggcgccg ggcagggccc        60
cgcgggcggc cgagggttgg gcccggctcc cagcccctcg ccgtcctccg gctgacaggg       120
ggaggagccc gccgggaggg ccggggtctc gggctgggga gccgggacgg agagcagcg        180
cagccgggtg caccgcggcc gcgccccggg agggctgttc gggccagcgc ccgccggctg       240
ctccgcgctg acagcgccgg gctggggcgg ggcggggggc tttgcaggcc gccagtgtcg       300
acatgctgct ggaggaggtt cgcgccggcg accggctgag tggggcggcg gcccggggcg       360
acgtgcagga ggtgcgccgc cttctgcacc gcgagctggt gcatcccgac gccctcaacc       420
gcttcggcaa gacggcgctg caggtcatga tgtttggcag caccgccatc gccctggagc       480
tgctgaagca aggtgccagc cccaatgtcc aggacacctc cggtaccagt ccagtccatg       540
acgcagcccg cactggattc ctggacaccc tgaaggtcct agtggagcac ggggctgatg       600
tcaacgtgcc tgatggcacc ggggcacttc caatccatct ggcagttcaa gagggtcaca       660
ctgctgtggt cagctttctg gcagctgaat ctgatctcca tcgcagggac gccaggggtc       720
tcacaccctt ggagctggca ctgcagagag ggctcagga cctcgtggac atcctgcagg       780
gccacatggt ggccccgctg tgatctgggg tcaccctctc cagcaagaga accccgtggg       840
gttatgtatc agaagagagg ggaagaaaca ctttctcttc ttgtttctcc tgcccactgc       900
tgcagtaggg gaggagcaca gtttgtggct tataggtgtt ggttttgggg gtgtgagtgt       960
ttggggacg tttctcattt gtttttctca ctccttttgg tgtgttggac agagaagggc      1020
tcctgcaggc cacagccacc taaacggttc agtttcttct gcgcctcagg ctgctgggc       1080
ctcagacgag acccaagggc agagcattta agagtgaagt catgacctcc agggagccta      1140
gaagctggtg gccttggccg gctgtgctca gagacctgaa gtgtgcacgt tgcttcaggc      1200
atggggggtg gggggagcgt cccaaatcaa taagaaggta gaatgagtta tgagttattc      1260
atattctgtt ggaagcttgt tttccagtct cttgtacagc gttttaaaag aaatggattc      1320
tatttattat gctttattgg aaaaaatgtt gtaataattt aatgttttta cccattaaat      1380
taagacttgt gcatgatcaa aaaaaaaaaa aaaaaa                                1416

<210> SEQ ID NO 8
<211> LENGTH: 595

<212> TYPE: PRT
<213> ORGANISM: Homo sapiens

<400> SEQUENCE: 8

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400
```

```
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Lys Asn Val Val Pro Leu Tyr Asp Leu Leu Leu Glu Met Leu
    530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595

<210> SEQ ID NO 9
<211> LENGTH: 6330
<212> TYPE: DNA
<213> ORGANISM: Homo sapiens

<400> SEQUENCE: 9
aggagctggc ggagggcgtt cgtcctggga ctgcacttgc tcccgtcggg tcgcccggct      60
tcaccggacc cgcaggctcc cggggcaggg ccggggccag agctcgcgtg tcggcgggac     120
atgcgctgcg tcgcctctaa cctcgggctg tgctcttttt ccaggtggcc cgccggtttc     180
tgagccttct gccctgcggg gacacggtct gcaccctgcc cgcggccacg gaccatgacc     240
atgaccctcc acaccaaagc atctgggatg gccctactgc atcagatcca agggaacgag     300
ctggagcccc tgaaccgtcc gcagctcaag atcccctgg agcggcccct gggcgaggtg     360
tacctggaca gcagcaagcc cgccgtgtac aactaccccg agggcgccgc ctacgagttc     420
aacgccgcgg ccgccgccaa cgcgcaggtc tacggtcaga ccggcctccc ctacggcccc     480
gggtctgagg ctgcggcgtt cggctccaac ggcctggggg gtttcccccc actcaacagc     540
gtgtctccga gcccgctgat gctactgcac ccgccgccgc agctgtcgcc tttcctgcag     600
ccccacggcc agcaggtgcc ctactacctg gagaacgagc cagcggcta cggtgcgc      660
gaggccggcc gccggcatt ctacaggcca aattcagata tcgacgcca gggtggcaga      720
gaaagattgg ccagtaccaa tgacaaggga agtatggcta tggaatctgc caaggagact     780
cgctactgtg cagtgtgcaa tgactatgct tcaggctacc attatggagt ctggtcctgt     840
gagggctgca aggccttctt caagagaagt attcaaggac ataacgacta tatgtgtcca     900
gccaccaacc agtgcaccat tgataaaaac aggaggaaga gctgccaggc ctgccggctc     960
```

```
cgcaaatgct acgaagtggg aatgatgaaa ggtgggatac gaaaagaccg aagaggaggg    1020
agaatgttga aacacaagcg ccagagagat gatggggagg gcaggggtga agtggggtct    1080
gctggagaca tgagagctgc caaccttcgg ccaagcccgc tcatgatcaa acgctctaag    1140
aagaacagcc tggccttgtc cctgacggcc gaccagatgg tcagtgcctt gttggatgct    1200
gagcccccca tactctattc cgagtatgat cctaccagac ccttcagtga agcttcgatg    1260
atgggcttac tgaccaacct ggcagacagg gagctggttc acatgatcaa ctgggcgaag    1320
agggtgccag gctttgtgga tttgaccctc catgatcagg tccaccttct agaatgtgcc    1380
tggctagaga tcctgatgat tggtctcgtc tggcgctcca tggagcaccc agggaagcta    1440
ctgtttgctc ctaacttgct cttggacagg aaccagggaa aatgtgtaga gggcatggtg    1500
gagatcttcg acatgctgct ggctacatca tctcggttcc gcatgatgaa tctgcaggga    1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc    1680
acagacactt tgatccacct gatggccaag gcaggcctga ccctgcagca gcagcaccag    1740
cggctggccc agctcctcct catcctctcc cacatcaggc acatgagtaa caaaggcatg    1800
gagcatctgt acagcatgaa gtgcaagaac gtggtgcccc tctatgacct gctgctggag    1860
atgctggacg cccaccgcct acatgcgccc actagccgtg gaggggcatc cgtggaggag    1920
acggaccaaa gccacttggc cactgcgggc tctacttcat cgcattcctt gcaaaagtat    1980
tacatcacgg gggaggcaga gggtttccct gccacggtct gagagctccc tggctcccac    2040
acggttcaga taatccctgc tgcattttac cctcatcatg caccacttta gccaaattct    2100
gtctcctgca tacactccgg catgcatcca acaccaatgg ctttctagat gagtggccat    2160
tcatttgctt gctcagttct tagtggcaca tcttctgtct tctgttggga acagccaaag    2220
ggattccaag gctaaatctt tgtaacagct ctctttcccc cttgctatgt tactaagcgt    2280
gaggattccc gtagctcttc acagctgaac tcagtctatg ggttggggct cagataactc    2340
tgtgcattta agctacttgt agagacccag gcctggagag tagacatttt gcctctgata    2400 agcactttt aaaatggctct aagaataagc cacagcaaag aatttaaagt ggctcccttta    2460 attggtgact tggagaaagc taggtcaagg gtttattata gcaccctctt gtattcctat    2520
ggcaatgcat cctttatga agtggtaca ccttaaagct tttatatgac tgtagcagag    2580
tatctggtga ttgtcaattc attcccccta taggaataca aggggcacac agggaaggca    2640
gatcccctag ttggcaagac tattttaact tgatacactg cagattcaga tgtgctgaaa    2700
gctctgcctc tggctttccg gtcatgggtt ccagttaatt catgcctccc atggacctat    2760
ggagagcagc aagttgatct tagttaagtc tccctatatg agggataagt tcctgatttt    2820 tgttttatt tttgtgttac aaaagaaagc cctccctccc tgaacttgca gtaaggtcag    2880
cttcaggacc tgttccagtg ggcactgtac ttggatcttc ccggcgtgtg tgtgccttac    2940
acaggggtga actgttcact gtggtgatgc atgatgaggg taaatggtag ttgaaaggag    3000
caggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttgggggtg ccctgggatc cctggggtag tccagctctt    3240
cttcatttcc cagcgtggcc ctggttggaa gaagcagctg tcacagctgc tgtagacagc    3300
```

-continued

```
tgtgttccta caattggccc agcaccctgg ggcacgggag aagggtgggg accgttgctg    3360
tcactactca ggctgactgg ggcctggtca gattacgtat gcccttggtg gtttagagat    3420
aatccaaaat cagggtttgg tttggggaag aaaatcctcc cccttcctcc cccgcccgt     3480 tccctaccgc ctccactcct gccagctcat ttccttcaat ttcctttgac ctataggcta    3540
aaaaagaaag gctcattcca gccacagggc agccttccct gggcctttgc ttctctagca    3600
caattatggg ttacttcctt tttcttaaca aaaagaatg tttgatttcc tctgggtgac    3660
cttattgtct gtaattgaaa ccctattgag aggtgatgtc tgtgttagcc aatgacccag    3720
gtgagctgct cgggcttctc ttggtatgtc ttgtttggaa aagtggattt cattcatttc    3780
tgattgtcca gttaagtgat caccaaagga ctgagaatct gggagggcaa aaaaaaaaa     3840 aaagttttta tgtgcactta aatttgggga caattttatg tatctgtgtt aaggatatgt    3900
ttaagaacat aattctttg ttgctgtttg tttaagaagc accttagttt gtttaagaag     3960
caccttatat agtataatat atatttttt gaaattacat tgcttgttta tcagacaatt     4020
gaatgtagta attctgttct ggatttaatt tgactgggtt aacatgcaaa aaccaaggaa    4080
aaatatttag ttttttttt tttttttgta tactttcaa gctaccttgt catgtataca      4140
gtcatttatg cctaaagcct ggtgattatt catttaaatg aagatcacat ttcatatcaa    4200
cttttgtatc cacagtagac aaaatagcac taatccagat gcctattgtt ggatactgaa    4260
tgacagacaa tcttatgtag caaagattat gcctgaaaag gaaaattatt cagggcagct    4320
aattttgctt ttaccaaaat atcagtagta atatttttgg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatattttct ggctgatgtt    4680
ggtattgggt gtaggaacat gatttaaaaa aaaactcttg cctctgcttt cccccactct    4740
gaggcaagtt aaaatgtaaa agatgtgatt tatctggggg gctcaggtat ggtgggaag    4800 tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttcttttcg    5040
ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220
atgccttttg agggctgaac aaataaggga cttactgata atttacttt gatcacatta     5280 aggtgttctc accttgaaat cttatacact gaaatggcca ttgatttagg ccactggctt    5340
agagtactcc ttcccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctcttttggtg caggtcttgg gagcgtgatc tagattacac    5580
tgcaccattc ccaagttaat cccctgaaaa cttactctca actggagcaa atgaactttg    5640
gtcccaaata tccatctttt cagtagcgtt aattatgctc tgtttccaac tgcatttcct    5700
```

-continued

```
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820
tattcttttt tttgcatcca attgtgcctg aacttttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agtttctgtt ctctcacagg tgataaacaa    6060 tgcttttttgt gcactacata ctcttcagtg tagagctctt gttttatggg aaaaggctca    6120
aatgccaaat tgtgtttgat ggattaatat gcccttttgc cgatgcatac tattactgat    6180
gtgactcggt tttgtcgcag ctttgctttg tttaatgaaa cacacttgta aacctctttt    6240
gcactttgaa aaagaatcca gcgggatgct cgagcacctg taaacaattt tctcaaccta    6300
tttgatgttc aaataaagaa ttaaactaaa                                     6330
```

<210> SEQ ID NO 10
<211> LENGTH: 1255
<212> TYPE: PRT
<213> ORGANISM: Homo sapiens

<400> SEQUENCE: 10

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

```
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
```

```
                675                 680                 685
Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095
```

```
Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 11
<211> LENGTH: 4663
<212> TYPE: DNA
<213> ORGANISM: Homo sapiens

<400> SEQUENCE: 11
gcttgctccc aatcacagga aaggaggag gtggaggagg agggctgctt gaggaagtat     60
aagaatgaag ttgtgaagct gagattcccc tccattggga ccggagaaac caggggagcc    120
ccccgggcag ccgcgcgccc cttcccacgg ggcccttttac tgcgccgcgc gcccggcccc   180 caccccctcgc agcaccccgc gccccgcgcc ctcccagccg ggtccagccg agccatggg    240 gccggagccg cagtgagcac catggagctg gcggccttgt gccgctgggg gctcctcctc    300
gccctcttgc cccccggagc cgcgagcacc caagtgtgca ccggcacaga catgaagctg    360
cggctccctg ccagtcccga gacccacctg gacatgctcc gccacctcta ccagggctgc    420
caggtggtgc agggaaacct ggaactcacc tacctgccca ccaatgccag cctgtccttc    480
ctgcaggata tccaggaggt gcagggctac gtgctcatcg ctcacaacca agtgaggcag    540
gtcccactgc agaggctgcg gattgtgcga ggcacccagc tctttgagga caactatgcc    600
ctggccgtgc tagacaatgg agacccgctg aacaatacca cccctgtcac aggggcctcc    660
ccaggaggcc tgcgggagct gcagcttcga agcctcacag agatcttgaa aggagggtc    720 ttgatccagc ggaaccccca gctctgctac caggacacga ttttgtggaa ggacatcttc    780
cacaagaaca accagctggc tctcacactg atagacacca accgctctcg ggcctgccac    840
ccctgttctc cgatgtgtaa gggctcccgc tgctgggag agagttctga ggattgtcag    900
agcctgacgc gcactgtctg tgccggtggc tgtgcccgct gcaagggcc actgcccact    960 gactgctgcc atgagcagtg tgctgccggc tgcacgggcc ccaagcactc tgactgcctg   1020
gcctgcctcc acttcaacca cagtggcatc tgtgagctgc actgcccagc cctggtcacc   1080
tacaacacag acacgtttga gtccatgccc aatcccgagg ccggtatac attcggcgcc   1140
```

```
agctgtgtga ctgcctgtcc ctacaactac ctttctacgg acgtgggatc ctgcaccctc   1200
gtctgccccc tgcacaacca agaggtgaca gcagaggatg aaacacagcg gtgtgagaag   1260
tgcagcaagc cctgtgcccg agtgtgctat ggtctgggca tggagcactt gcgagaggtg   1320
agggcagtta ccagtgccaa tatccaggag tttgctggct gcaagaagat ctttgggagc   1380
ctggcatttc tgccggagag ctttgatggg gacccagcct ccaacactgc cccgctccag   1440
ccagagcagc tccaagtgtt tgagactctg aagagatca caggttacct atacatctca   1500
gcatggccgg acagcctgcc tgacctcagc gtcttccaga acctgcaagt aatccgggga   1560
cgaattctgc acaatggcgc ctactcgctg accctgcaag ggctgggcat cagctggctg   1620
gggctgcgct cactgaggga actgggcagt ggactggccc tcatccacca taacacccac   1680
ctctgcttcg tgcacacggt gccctgggac cagctctttc ggaacccgca ccaagctctg   1740
ctccacactg ccaaccggcc agaggacgag tgtgtgggcg agggcctggc ctgccaccag   1800
ctgtgcgccc gagggcactg ctggggtcca gggcccaccc agtgtgtcaa ctgcagccag   1860
ttccttcggg gccaggagtg cgtggaggaa tgccgagtac tgcagggggct ccccagggag   1920 tatgtgaatg ccaggcactg tttgccgtgc caccctgagt gtcagcccca gaatggctca   1980
gtgacctgtt ttggaccgga ggctgaccag tgtgtggcct gtgcccacta taaggaccct   2040
cccttctgcg tggcccgctg ccccagcggt gtgaaacctg acctctccta catgcccatc   2100
tggaagtttc cagatgagga gggcgcatgc cagccttgcc ccatcaactg cacccactcc   2160
tgtgtggacc tggatgacaa gggctgcccc gccgagcaga gagccagccc tctgacgtcc   2220
atcatctctg cggtggttgg cattctgctg gtcgtggtct tgggggtggt cttggggtatc   2280 ctcatcaagc gacggcagca gaagatccgg aagtacacga tgcggagact gctgcaggaa   2340
acggagctgg tggagccgct gacacctagc ggagcgatgc ccaaccaggc gcagatgcgg   2400
atcctgaaag agacggagct gaggaaggtg aaggtgcttg gatctggcgc ttttggcaca   2460
gtctacaagg gcatctggat ccctgatggg gagaatgtga aaattccagt ggccatcaaa   2520
gtgttgaggg aaaacacatc ccccaaagcc aacaaagaaa tcttagacga agcatacgtg   2580
atggctggtg tgggctcccc atatgtctcc cgccttctgg gcatctgcct gacatccacg   2640
gtgcagctgg tgacacagct tatgcccta ggctgcctct tagaccatgt ccgggaaaac   2700
cgcggacgcc tgggctccca ggacctgctg aactggtgta gcagattgc caaggggatg   2760 agctacctgg aggatgtgcg gctcgtacac agggacttgg ccgctcggaa cgtgctggtc   2820
aagagtccca accatgtcaa aattacagac ttcgggctgg ctcggctgct ggacattgac   2880
gagacagagt accatgcaga tgggggcaag gtgcccatca gtggatggc gctggagtcc   2940 attctccgcc ggcggttcac ccaccagagt gatgtgtgga gttatggtgt gactgtgtgg   3000
gagctgatga cttttgggc caaaccttac gatgggatcc cagcccggga gatccctgac   3060
ctgctggaaa aggggagcg gctgcccag cccccatct gcaccattga tgtctacatg   3120
atcatggtca aatgttggat gattgactct gaatgtcggc caagattccg ggagttggtg   3180
tctgaattct cccgcatggc cagggacccc cagcgctttg tggtcatcca gaatgaggac   3240
ttgggcccag ccagtcccct tggacagcacc ttctaccgct cactgctgga ggacgatgac   3300
atgggggacc tggtggatgc tgaggagtat ctggtacccc agcagggctt cttctgtcca   3360
gaccctgccc cggcgctgg gggcatggtc caccacaggc accgcagctc atctaccagg   3420
agtggcggtg gggacctgac actagggctg gagccctctg aagaggaggc ccccaggtct   3480
```

-continued

```
ccactggcac cctccgaagg ggctggctcc gatgtatttg atggtgacct gggaatgggg    3540
gcagccaagg ggctgcaaag cctccccaca catgaccccca gccctctaca gcggtacagt    3600 gaggaccccca cagtacccct gccctctgag actgatggct acgttgcccc cctgacctgc    3660 agccccccagc ctgaatatgt gaaccagcca gatgttcggc cccagccccc ttcgccccga    3720
gagggccctc tgcctgctgc ccgacctgct ggtgccactc tggaaaggcc caagactctc    3780
tccccaggga agaatggggt cgtcaaagac gttttttgcct ttgggggtgc cgtggagaac    3840
cccgagtact tgacacccca gggaggagct gcccctcagc ccacccctcc tcctgccttc    3900
agcccagcct tcgacaacct ctattactgg gaccaggacc caccagagcg ggggctcca    3960 cccagcacct tcaaagggac acctacggca gagaacccag agtacctggg tctggacgtg    4020
ccagtgtgaa ccagaaggcc aagtccgcag aagccctgat gtgtcctcag ggagcaggga    4080
aggcctgact tctgctggca tcaagaggtg ggagggccct ccgaccactt ccaggggaac    4140
ctgccatgcc aggaacctgt cctaaggaac cttccttcct gcttgagttc ccagatggct    4200 ggaagggggtc cagcctcgtt ggaagaggaa cagcactggg gagtctttgt ggattctgag    4260
gccctgccca atgagactct agggtccagt ggatgccaca gcccagcttg ccctttcct    4320 tccagatcct gggtactgaa agccttaggg aagctggcct gagaggggaa gcggccctaa    4380
gggagtgtct aagaacaaaa gcgacccatt cagagactgt ccctgaaacc tagtactgcc    4440
ccccatgagg aaggaacagc aatggtgtca gtatccaggc tttgtacaga gtgcttttct    4500
gtttagtttt tacttttttt gttttgtttt tttaaagatg aaataaagac ccaggggag    4560 aatgggtgtt gtatggggag gcaagtgtgg ggggtccttc tccacaccca ctttgtccat    4620
ttgcaaatat attttggaaa acagctaaaa aaaaaaaaaa aaa                     4663
```

<210> SEQ ID NO 12
<211> LENGTH: 933
<212> TYPE: PRT
<213> ORGANISM: Homo sapiens

<400> SEQUENCE: 12

```
Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
            20                  25                  30

Ala Gly Pro Phe Pro Gly Ser Gln Thr Ser Asp Thr Leu Pro Glu Val
        35                  40                  45

Ser Ala Ile Pro Ile Ser Leu Asp Gly Leu Leu Phe Pro Arg Pro Cys
    50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
    130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
```

```
                165                 170                 175
Gly Thr Ala Ala Ala His Lys Val Leu Pro Arg Gly Leu Ser Pro Ala
                180                 185                 190

Arg Gln Leu Leu Leu Pro Ala Ser Glu Ser Pro His Trp Ser Gly Ala
                195                 200                 205

Pro Val Lys Pro Ser Pro Gln Ala Ala Val Glu Val Glu Glu Glu
                210                 215                 220

Asp Gly Ser Glu Ser Glu Ser Ala Gly Pro Leu Leu Lys Gly Lys
225                 230                 235                 240

Pro Arg Ala Leu Gly Ala Ala Gly Gly Ala Ala Val
                245                 250                 255

Pro Pro Gly Ala Ala Gly Gly Val Ala Leu Val Pro Lys Glu Asp
                260                 265                 270

Ser Arg Phe Ser Ala Pro Arg Val Ala Leu Val Glu Gln Asp Ala Pro
                275                 280                 285

Met Ala Pro Gly Arg Ser Pro Leu Ala Thr Thr Val Met Asp Phe Ile
                290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Ala Gly Ala Ala
                325                 330                 335

Ser Ala Phe Ala Pro Pro Arg Ser Pro Cys Ala Ser Ser Thr Pro
                340                 345                 350

Val Ala Val Gly Asp Phe Pro Asp Cys Ala Tyr Pro Pro Asp Ala Glu
                355                 360                 365

Pro Lys Asp Asp Ala Tyr Pro Leu Tyr Ser Asp Phe Gln Pro Pro Ala
                370                 375                 380

Leu Lys Ile Lys Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Leu Pro Pro Arg Ala Thr Pro Ser
                420                 425                 430

Arg Pro Gly Glu Ala Ala Val Thr Ala Ala Pro Ala Ser Ala Ser Val
                435                 440                 445

Ser Ser Ala Ser Ser Gly Ser Thr Leu Glu Cys Ile Leu Tyr Lys
                450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Gly Ala Ala Pro Ala Leu Tyr
                500                 505                 510

Pro Ala Leu Gly Leu Asn Gly Leu Pro Gln Leu Gly Tyr Gln Ala Ala
                515                 520                 525

Val Leu Lys Glu Gly Leu Pro Gln Val Tyr Pro Pro Tyr Leu Asn Tyr
                530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
                580                 585                 590
```

```
Arg Ala Met Glu Gly Gln His Asn Tyr Leu Cys Ala Gly Arg Asn Asp
            595                 600                 605

Cys Ile Val Asp Lys Ile Arg Lys Asn Cys Pro Ala Cys Arg Leu
610                 615                 620

Arg Lys Cys Cys Gln Ala Gly Met Val Leu Gly Gly Arg Lys Phe Lys
625                 630                 635                 640

Lys Phe Asn Lys Val Arg Val Arg Ala Leu Asp Ala Val Ala Leu
            645                 650                 655

Pro Gln Pro Val Gly Val Pro Asn Glu Ser Gln Ala Leu Ser Gln Arg
                660                 665                 670

Phe Thr Phe Ser Pro Gly Gln Asp Ile Gln Leu Ile Pro Pro Leu Ile
            675                 680                 685

Asn Leu Leu Met Ser Ile Glu Pro Asp Val Ile Tyr Ala Gly His Asp
    690                 695                 700

Asn Thr Lys Pro Asp Thr Ser Ser Ser Leu Leu Thr Ser Leu Asn Gln
705                 710                 715                 720

Leu Gly Glu Arg Gln Leu Leu Ser Val Val Lys Trp Ser Lys Ser Leu
                725                 730                 735

Pro Gly Phe Arg Asn Leu His Ile Asp Asp Gln Ile Thr Leu Ile Gln
            740                 745                 750

Tyr Ser Trp Met Ser Leu Met Val Phe Gly Leu Gly Trp Arg Ser Tyr
        755                 760                 765

Lys His Val Ser Gly Gln Met Leu Tyr Phe Ala Pro Asp Leu Ile Leu
    770                 775                 780

Asn Glu Gln Arg Met Lys Glu Ser Ser Phe Tyr Ser Leu Cys Leu Thr
785                 790                 795                 800

Met Trp Gln Ile Pro Gln Glu Phe Val Lys Leu Gln Val Ser Gln Glu
                805                 810                 815

Glu Phe Leu Cys Met Lys Val Leu Leu Leu Asn Thr Ile Pro Leu
            820                 825                 830

Glu Gly Leu Arg Ser Gln Thr Gln Phe Glu Glu Met Arg Ser Ser Tyr
        835                 840                 845

Ile Arg Glu Leu Ile Lys Ala Ile Gly Leu Arg Gln Lys Gly Val Val
    850                 855                 860

Ser Ser Ser Gln Arg Phe Tyr Gln Leu Thr Lys Leu Leu Asp Asn Leu
865                 870                 875                 880

His Asp Leu Val Lys Gln Leu His Leu Tyr Cys Leu Asn Thr Phe Ile
                885                 890                 895

Gln Ser Arg Ala Leu Ser Val Glu Phe Pro Glu Met Met Ser Glu Val
            900                 905                 910

Ile Ala Ala Gln Leu Pro Lys Ile Leu Ala Gly Met Val Lys Pro Leu
        915                 920                 925

Leu Phe His Lys Lys
    930

<210> SEQ ID NO 13
<211> LENGTH: 3014
<212> TYPE: DNA
<213> ORGANISM: Homo sapiens

<400> SEQUENCE: 13
ctgaccagcg ccgccctccc ccgcccccga cccaggaggt ggagatccct ccggtccagc      60
cacattcaac acccactttc tcctccctct gcccctatat tcccgaaacc ccctcctcct     120
```

| | |
|---|---|
| tcccttttcc ctcctccctg gagacggggg aggagaaaag gggagtccag tcgtcatgac | 180 |
| tgagctgaag gcaaagggtc cccgggctcc ccacgtggcg ggcggcccgc cctccccga | 240 |
| ggtcggatcc ccactgctgt gtcgcccagc cgcaggtccg ttcccgggga gccagacctc | 300 |
| ggacaccttg cctgaagttt cggccatacc tatctccctg gacgggctac tcttccctcg | 360 |
| gccctgccag ggacaggacc cctccgacga aaagacgcag gaccagcagt cgctgtcgga | 420 |
| cgtggagggc gcatattcca gagctgaagc tacaaggggt gctggaggca gcagttctag | 480 |
| tcccccagaa aaggacagcg gactgctgga cagtgtcttg gacactctgt ggcgccctc | 540 |
| aggtcccggg cagagccaac ccagccctcc cgcctgcgag gtcaccagct cttggtgcct | 600 |
| gtttggcccc gaacttcccg aagatccacc ggctgccccc gccacccagc gggtgttgtc | 660 |
| cccgctcatg agccggtccg ggtgcaaggt tggagacagc tccggacgg cagctgccca | 720 |
| taaagtgctg ccccggggcc tgtcaccagc ccggcagctg ctgctcccgg cctctgagag | 780 |
| ccctcactgg tccggggccc cagtgaagcc gtctccgcag gccgctgcgg tggaggttga | 840 |
| ggaggaggat ggctctgagt ccgaggagtc tgcgggtccg cttctgaagg gcaaacctcg | 900 |
| ggctctgggt ggcgcggcgg ctggaggagg agccgcggct gtcccgccgg gggcggcagc | 960 |
| aggaggcgtc gccctggtcc ccaaggaaga ttcccgcttc tcagcgccca gggtcgccct | 1020 |
| ggtggagcag gacgcgccga tggcgcccgg gcgctccccg ctggccacca cggtgatgga | 1080 |
| tttcatccac gtgcctatcc tgcctctcaa tcacgcctta ttggcagccc gcactcggca | 1140 |
| gctgctggaa gacgaaagtt acgacggcgg ggccggggct gccagcgcct ttgccccgcc | 1200 |
| gcggagttca ccctgtgcct cgtccacccc ggtcgctgta ggcgacttcc ccgactcgc | 1260 |
| gtacccgccc gacgccgagc ccaaggacga cgcgtaccct ctctatagcg acttccagcc | 1320 |
| gcccgctcta aagataaagg aggaggagga aggcgcggag gcctccgcgc gctcccccgcg | 1380 |
| ttcctacctt gtggccggtg ccaaccccgc agccttcccg gatttcccgt tggggccacc | 1440 |
| gccccgctg ccgccgcgag cgaccccatc cagacccggg gaagcggcgg tgacggccgc | 1500 |
| acccgccagt gcctcagtct cgtctgcgtc ctcctcgggg tcgaccctgg agtgcatcct | 1560 |
| gtacaaagcg gagggcgcgc cgccccagca gggcccgttc gcgccgccgc cctgcaaggc | 1620 |
| gccgggcgcg agcggctgcc tgctccccgcg ggacggcctg ccctccacct ccgcctctgc | 1680 |
| cgccgccgcc gggggcggccc ccgcgctcta ccctgcactc ggcctcaacg ggctcccgca | 1740 |
| gctcggctac caggccgccg tgctcaagga gggcctgccg caggtctacc cgccctatct | 1800 |
| caactacctg aggccggatt cagaagccag ccagagccca caatacagct tcgagtcatt | 1860 |
| acctcagaag atttgtttaa tctgtgggga tgaagcatca ggctgtcatt atggtgtcct | 1920 |
| tacctgtggg agctgtaagg tcttctttaa gagggcaatg gaaggcagc acaactactt | 1980 |
| atgtgctgga agaaatgact gcatcgttga taaaatccgc agaaaaaact gcccagcatg | 2040 |
| tcgccttaga aagtgctgtc aggctggcat ggtccttgga ggtcgaaaat ttaaaaagtt | 2100 |
| caataaagtc agagttgtga gagcactgga tgctgttgct ctcccacagc cattgggcgt | 2160 |
| tccaaatgaa agccaagccc taagccagag attcactttt tcaccaggtc aagacataca | 2220 |
| gttgattcca ccactgatca acctgttaat gagcattgaa ccagatgtga tctatgcagg | 2280 |
| acatgacaac acaaaacctg cacctccag ttctttgctg acaagtctta atcaactagg | 2340 |
| cgagaggcaa cttctttcag tagtcaagtg gtctaaatca ttgccaggtt ttcgaaactt | 2400 |
| acatattgat gaccagataa ctctcattca gtattcttgg atgagcttaa tggtgtttgg | 2460 |
| tctaggatgg agatcctaca aacatgtcag tgggcagatg ctgtattttg cacctgatct | 2520 |

```
aatactaaat gaacagcgga tgaaagaatc atcattctat tcattatgcc ttaccatgtg    2580
gcagatccca caggagtttg tcaagcttca agttagccaa gaagagttcc tctgtatgaa    2640
agtattgtta cttcttaata caattccttt ggaagggcta cgaagtcaaa cccagtttga    2700
ggagatgagg tcaagctaca ttagagagct catcaaggca attggtttga ggcaaaaagg    2760
agttgtgtcg agctcacagc gtttctatca acttacaaaa cttcttgata acttgcatga    2820
tcttgtcaaa caacttcatc tgtactgctt gaatacattt atccagtccc gggcactgag    2880
tgttgaattt ccagaaatga tgtctgaagt tattgctgca caattaccca agatattggc    2940
agggatggtg aaaccccttc tctttcataa aaagtgaatg tcatcttttt cttttaaaga    3000
attaaatttt gtgg                                                      3014
```

<210> SEQ ID NO 14
<211> LENGTH: 412
<212> TYPE: PRT
<213> ORGANISM: Homo sapiens

<400> SEQUENCE: 14

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Gly Val Gly Ala Arg
        35                  40                  45

Gly Val Ala Leu Lys Leu Phe Val Gln Leu Leu Gly Cys Ser Arg Phe
 50                 55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
```

-continued

```
                275                 280                 285
Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
                340                 345                 350

Leu Met Pro Trp Ser Leu Pro Gly Pro His Pro Cys Gly Pro Cys Ser
                355                 360                 365

Glu Arg Arg Lys His Leu Phe Val Gln Asp Pro Gln Thr Cys Lys Cys
                370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 15
<211> LENGTH: 581
<212> TYPE: DNA
<213> ORGANISM: Homo sapiens

<400> SEQUENCE: 15
atgaactttc tgctgtcttg ggtgcattgg agccttgcct tgctgctcta cctccaccat    60
gccaagtggt cccaggctgc acccatggca gaaggaggag ggcagaatca tcacgaagtg   120
gtgaagttca tggatgtcta tcagcgcagc tactgccatc caatcgagac cctggtggac   180
atcttccagg agtaccctga tgagatcgag tacatcttca agccatcctg tgtgcccctg   240
atgcgatgcg ggggctgctg caatgacgag ggcctggagt gtgtgcccac tgaggagtcc   300
aacatcacca tgcagattat gcggatcaaa cctcaccaag gccagcacat aggagagatg   360
agcttcctac agcacaacaa atgtgaatgc agaccaaaga aagatagagc aagacaagaa   420
atccctgtgg gccttgctca gagcggagaa agcatttgtt tgtacaagat ccgcagacgt   480
gtaaatgttc ctgcaaaaac acagactcgc gttgcaaggc gaggcagctt gagttaaacg   540
aacgtacttg aagatgtgac aagccgaggc ggtgatgaat g                       581
```

COMPOSITIONS AND METHODS FOR DIAGNOSING BREAST CANCER

This application claims benefit of U.S. Provisional Patent Application No. 62/427,663, filed Nov. 29, 2016, the entire contents of which are incorporated herein by reference.

STATEMENT OF RIGHTS TO INVENTIONS MADE UNDER FEDERALLY SPONSORED RESEARCH

This invention was made with government support under Grant W81XWH-11-1-0814 awarded by the United States Army. The government has certain rights in the invention.

SEQUENCE LISTING

This application contains a Sequence Listing which has been submitted electronically in ASCII format and is hereby incorporated by reference in its entirety. The ASCII copy, created on Jan. 8, 2018, is named 167774_011601-US-_SL.txt and is 63,835 bytes in size.

BACKGROUND OF THE INVENTION

Current approaches to breast cancer screening, such as mammography, have proven to be limited in clinical sensitivity and specificity. Furthermore, invasive biopsy techniques are required to characterize the disease biologically and formulate a treatment plan. Improved methods for detecting breast cancer at an early stage are urgently required.

SUMMARY OF THE INVENTION

As described below, the present invention features compositions and methods for detecting breast cancer. In particular embodiments, the invention provides methods for detecting breast cancer using one or more of the following biomarkers: CA 15-3, CA 19-9, CDKN2D, CYR61, ER alpha, HER2, PR, and VEGF.

The invention provides compositions and methods for detecting breast cancer in a sample of a subject (e.g., serum, plasma). Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Cancer antigen 15-3 (CA 15-3) polypeptide" is meant a protein or fragment thereof having at least 85% homology to the sequence provided at NCBI Accession No. NP_002447.4 that binds a Cancer antigen 15-3 antibody. An exemplary amino acid sequence is provided below.

```
                                                            (SEQ ID NO: 1)
  1 mtpgtqspff lllltvltv vtgsghasst pggeketsat qrssvpsste knalstgvsf 61 fflsfhisnl qfnssledps tdyyqelqrd isemflqiyk qggflglsni kfrpgsvvvq 121 ltlafregti nvhdvetqfn qykteaasry nltisdvsvs dvpfpfsaqs gagvpgwgia 181 llvlvcvlva laivyliala vcqcrrknyg qldifpardt yhpmseypty hthgryvpps 241 stdrspyekv sagnggssls ytnpavaats anl
```

By "Cancer antigen 15-3 (CA 15-3) nucleic acid molecule" is meant a polynucleotide or fragment thereof that encodes a CA 15-3 polypeptide. An exemplary CA 15-3 nucleic acid sequence is provided at NCBI Accession No. NM_002456.5 and shown below.

```
                                                            (SEQ ID NO: 2)
  1 cgctccacct ctcaagcagc cagcgcctgc ctgaatctgt tctgccccct ccccacccat 61 ttcaccacca ccatgacacc gggcacccag tctcctttct tcctgctgct gctcctcaca 121 gtgcttacag ttgttacggg ttctggtcat gcaagctcta ccccaggtgg agaaaaggag 181 acttcggcta cccagagaag ttcagtgccc agctctactg agaagaatgc tttgtctact 241 ggggtctctt tcttttcct gtcttttcac atttcaaacc tccagtttaa ttcctctctg 301 gaagatccca gcaccgacta ctaccaagag ctgcagagag acatttctga aatgttttg 361 cagatttata aacaagggg ttttctgggc ctctccaata ttaagttcag gccaggatct
```

```
421 gtggtggtac aattgactct ggccttccga gaaggtacca tcaatgtcca cgacgtggag 481 acacagttca atcagtataa aacggaagca gcctctcgat ataacctgac gatctcagac 541 gtcagcgtga gtgatgtgcc atttcctttc tctgcccagt ctggggctgg ggtgccaggc 601 tggggcatcg cgctgctggt gctggtctgt gttctggttg cgctggccat tgtctatctc 661 attgccttgg ctgtctgtca gtgccgccga aagaactacg ggcagctgga catctttcca 721 gcccgggata cctaccatcc tatgagcgag tacccacct accacaccca tgggcgctat 781 gtgccccta gcagtaccga tcgtagcccc tatgagaagg tttctgcagg taatggtggc 841 agcagcctct cttacacaaa cccagcagtg gcagccactt ctgccaactt gtaggggcac 901 gtcgcccgct gagctgagtg gccagccagt gccattccac tccactcagg ttcttcaggg 961 ccagagcccc tgcaccctgt ttgggctggt gagctgggag ttcaggtggg ctgctcacag 1021 cctccttcag aggcccacc aatttctcgg acacttctca gtgtgtggaa gctcatgtgg 1081 gcccctgagg gctcatgcct gggaagtgtt gtggtgggg ctcccaggag gactggccca 1141 gagagccctg agatagcggg gatcctgaac tggactgaat aaaacgtggt ctcccactgc 1201 gccaaaaaa aaaaaaaaa
```

By "Cancer antigen 19-9 (CA 19-9) polypeptide" is meant a protein or fragment thereof that binds a CA 19-9 antibody. In one embodiment, a CA 19-9 polypeptide has at least 85% homology to the sequence provided below:

```
                                                          (SEQ ID NO: 3)
  1 MGHHHHHHSG SEFRVSRDDA TGSPRAPSGS SRQDTTPTRP TLLILLWTWP FHIPVALSRC

61 SEMVPGTADC HITADRKVYP QADTVIVHHW DIMSNPKSRL PPSPRPQGQR WIWFNLEPPP

121 NCQHLEALDR YFNLTMSYRS DSDIFTPYGW LEPWSGQPAH PPLNLSAKTE LVAWAVSNWK

181 PDSARVRYYQ SLQAHLKVDV YGRSHKPLPK GTMMETLSRY KFYLAFENSL HPDYITEKLW

241 RNALEAWAVP VVLGPSRSNY ERFLPPDAFI HVDDFQSPKD LARYLQELDK DHARYLSYFR
```

By "Cancer antigen 19-9 (CA 19-9) nucleic acid molecule" is meant a polynucleotide or fragment thereof that encodes a CA 19-9 polypeptide.

By "cysteine rich angiogenic inducer 61 (CYR61) polypeptide" is meant a protein or fragment thereof having at least 85% homology to the sequence provided at GenBank Accession No. CAG38757.1 that regulates a cellular activity (e.g., cell adhesion, migration, proliferation, differentiation, apoptosis). An exemplary amino acid sequence is provided below.

```
                                                          (SEQ ID NO: 4)
  1 mssriarala lvvtllhltr lalstcpaac hcpleapkca pgvglvrdgc gcckvcakql 61 nedcsktqpc dhtkglecnf gasstalkgi craqsegrpc eynsriyqng esfqpnckhq 121 ctcidgavgc iplcpqelsl pnlgcpnprl vkvtgqccee wvcdedsikd pmedqdgllg 181 kelgfdasev eltrnnelia vgkgsslkrl pvfgmepril ynplqgqkci vqttswsqcs 241 ktcgtgistr vtndnpecrl vketricevr pcgqpvyssl kkgkkcsktk kspepvrfty 301 agclsvkkyr pkycgscvdg rcctpqltrt vkmrfrcedg etfsknvmmi qsckcnyncp 361 haneaafpfy rlfndihkfr d
```

By "cysteine rich angiogenic inducer 61 (CYR61) nucleic acid molecule" is meant a polynucleotide or fragment thereof that encodes a CYR61 polypeptide. An exemplary CYR61 nucleic acid sequence is provided at NCBI Accession No. NM_001554.4 and shown below.

(SEQ ID NO: 5)

```
   1 agaccgcgag cgagagcgcc cccgagcagc gcccgcgccc tccgcgcctt ctccgccggg
  61 acctcgagcg aaagacgccc gcccgccgcc cagcccgcgc ctccctgccc accgggccca
 121 ccgcgccgcc accccgaccc cgctgcgcac ggcctgtccg ctgcacacca gcttgttggc
 181 gtcttcgtcg ccgcgctcgc cccgggctac tcctgcgcgc acaatgagc tcccgcatcg
 241 ccagggcgct cgccttagtc gtcacccttc tccacttgac caggctggcg ctctccacct
 301 gccccgctgc ctgccactgc ccctggagg cgcccaagtg cgcgccggga gtcgggctgg
 361 tccgggacgg ctgcggctgc tgtaaggtct gcgccaagca gctcaacgag gactgcagca
 421 aaacgcagcc ctgcgaccac accaggggc tggaatgcaa cttcggcgcc agctccaccg
 481 ctctgaaggg gatctgcaga gctcagtcag agggcagacc ctgtgaatat aactccagaa
 541 tctaccaaaa cggggaaagt ttccagccca actgtaaaca tcagtgcaca tgtattgatg
 601 gcgccgtggg ctgcattcct ctgtgtcccc aagaactatc tctccccaac ttgggctgtc
 661 ccaaccctcg gctggtcaaa gttaccgggc agtgctgcga ggagtgggtc tgtgacgagg
 721 atagtatcaa ggaccccatg gaggaccagg acggcctcct tggcaaggag ctgggattcg
 781 atgcctccga ggtggagttg acgagaaaca atgaattgat tgcagttgga aaaggcagct
 841 cactgaagcg gctccctgtt tttggaatgg agcctcgcat cctatacaac cctttacaag
 901 gccagaaatg tattgttcaa acaacttcat ggtcccagtg ctcaaagacc tgtgaactg
 961 gtatctccac acgagttacc aatgacaacc ctgagtgccg ccttgtgaaa gaaacccgga
1021 tttgtgaggt gcggccttgt ggacagccag tgtacagcag cctgaaaaag ggcaagaaat
1081 gcagcaagac caagaaatcc cccgaaccag tcaggtttac ttacgctgga tgtttgagtg
1141 tgaagaaata ccggcccaag tactgcggtt cctgcgtgga cggccgatgc tgcacgcccc
1201 agctgaccag gactgtgaag atgcggttcc gctgcgaaga tggggagaca ttttccaaga
1261 acgtcatgat gatccagtcc tgcaaatgca actacaactg cccgcatgcc aatgaagcag
1321 cgtttccctt ctacaggctg ttcaatgaca ttcacaaatt tagggactaa atgctacctg
1381 ggtttccagg gcacacctag acaaacaagg gagaagagtg tcagaatcag aatcatggag
1441 aaaatgggcg ggggtggtgt gggtgatggg actcattgta gaaaggaagc cttgctcatt
1501 cttgaggagc attaaggtat ttcgaaactg ccaagggtgc tggtgcggat ggacactaat
1561 gcagccacga ttggagaata ctttgcttca tagtattgga gcacatgtta ctgcttcatt
1621 ttggagcttg tggagttgat gactttctgt tttctgtttg taaattattt gctaagcata
1681 ttttctctag gcttttttcc ttttgggtt ctacagtcgt aaaagagata ataagattag
1741 ttggacagtt taaagctttt attcgtcctt tgacaaaagt aaatgggagg gcattccatc
1801 ccttcctgaa gggggacact ccatgagtgt ctgtgagagg cagctatctg cactctaaac
1861 tgcaaacaga atcaggtgt tttaagactg aatgttttat ttatcaaaat gtagcttttg
1921 ggagggagg ggaaatgtaa tactggaata atttgtaaat gattttaatt ttatattcag
1981 tgaaaagatt ttatttatgg aattaaccat ttaataaaga aatatttacc taatatctga
2041 gtgtatgcca ttcggtattt ttagaggtgc tccaaagtca ttaggaacaa cctagctcac
2101 gtactcaatt attcaaacag gacttattgg gatacagcag tgaattaagc tattaaaata
2161 agataatgat tgcttttata ccttcagtag agaaaagtct ttgcatataa agtaatgttt
2221 aaaaaacatg tattgaacac gacattgtat gaagcacaat aaagattctg aagctaaatt
2281 tgtgatttaa gaaaa
```

By "Cyclin Dependent Kinase Inhibitor 2D (CDKN2D) polypeptide" is meant a protein or fragment thereof having at least 85% homology to the sequence provided at GenBank Accession No. AAM54045.1 that inhibits a kinase. An exemplary amino acid sequence is provided below.

(SEQ ID NO: 6)
```
  1 mlleevragd rlsgaaargd vqevrrllhr elvhpdalnr fgktalqvmm fgstaialel
 61 lkqgaspnvq dtsgtspvhd aartgfldtl kvlvehgadv nvpdgtgalp ihlavqeght
121 avvsflaaes dlhrrdargl tplelalqrg aqdlvdilqg hmvapl
```

By "Cyclin Dependent Kinase Inhibitor 2D (CDKN2D) nucleic acid molecule" is meant a polynucleotide or fragment thereof that encodes a CDKN2D polypeptide. An exemplary CDKN2D nucleic acid sequence is provided at NCBI Accession No. NM_001800.3 and shown below.

(SEQ ID NO: 7)
```
   1 ggagggaggg tgagttaggg ggagacccgg cccccaaggg gcgggcgccg ggcagggccc
  61 cgcgggcggc cgagggttgg gcccggctcc cagcccctcg ccgtcctccg gctgacaggg
 121 ggaggagccc gccgggaggg ccggggtctc gggctgggga gccgggacgg gagagcagcg
 181 cagccgggtg caccgcggcc gcgccccggg agggctgttc gggccagcgc ccgccggctg
 241 ctccgcgctg acacgccgg gctgggg cgg gcgggggggc tttgcaggcc gccagtgtcg
 301 acatgctgct ggaggaggtt cgcgccggcg accggctgag tggggcggcg gcccggggcg
 361 acgtgcagga ggtgcgccgc cttctgcacc gcgagctggt gcatcccgac gccctcaacc
 421 gcttcggcaa gacggcgctg caggtcatga tgtttggcag caccgccatc gccctggagc
 481 tgctgaagca aggtgccagc cccaatgtcc aggacacctc cggtaccagt ccagtccatg
 541 acgcagcccg cactggattc ctggacaccc tgaaggtcct agtggagcac ggggctgatg
 601 tcaacgtgcc tgatggcacc ggggcacttc caatccatct ggcagttcaa gagggtcaca
 661 ctgctgtggt cagctttctg gcagctgaat ctgatctcca tcgcagggac gccagggggtc
 721 tcacacccct tggagctggca ctgcagagag gggctcagga cctcgtggac atcctgcagg
 781 gccacatggt ggccccgctg tgatctgggg tcaccctctc cagcaagaga accccgtggg
 841 gttatgtatc agaagagagg ggaagaaaca ctttctcttc ttgtttctcc tgcccactgc
 901 tgcagtaggg gaggagcaca gtttgtggct tataggtgtt ggttttgggg gtgtgagtgt
 961 ttgggggacg tttctcattt gttttctca ctccttttgg tgtgttggac agagaagggc
1021 tcctgcaggc cacagccacc taaacggttc agtttcttct gcgcctcagg ctgctggggc
1081 ctcagacgag acccaagggc agagcattta agagtgaagt catgacctcc agggagccta
1141 gaagctggtg gccttggccg gctgtgctca gagacctgaa gtgtgcacgt tgcttcaggc
1201 atggggggtg gggggagcgt cccaaatcaa taagaaggta gaatgagtta tgagttattc
1261 atattctgtt ggaagcttgt tttccagtct cttgtacagc gttttaaaag aaatggattc
1321 tatttattat gctttattgg aaaaaatgtt gtaataattt aatgttttta cccattaaat
1381 taagacttgt gcatgatcaa aaaaaaaaaa aaaaaa
```

By "Estrogen receptor alpha (ER alpha, ER-α) polypeptide" is meant a protein or fragment thereof having at least 85% homology to the sequence provided at UniProtKB/Swiss-Prot Accession No. P03372.2 that binds estrogen. An exemplary amino acid sequence is provided below.

(SEQ ID NO: 8)
```
  1 mtmtlhtkas gmallhqiqg neleplnrpq lkiplerplg evyldsskpa vynypegaay
 61 efnaaaaana qvyggtglpy gpgseaaafg snglggfppl nsvspsplml lhpppqlspf
121 lqphgqqvpy ylenepsgyt vreagppafy rpnsdnrrqg grerlastnd kgsmamesak
```

-continued

```
181 etrycavcnd yasgyhygvw scegckaffk rsiqghndym cpatnqctid knrrkscqac 241 rlrkcyevgm mkggirkdrr ggrmlkhkrq rddgegrgev gsagdmraan lwpsplmikr 301 skknslalsl tadqmvsall daeppilyse ydptrpfsea smmglltnla drelvhminw 361 akrvpgfvdl tlhdqvhlle cawleilmig lvwrsmehpg kllfapnlll drnqgkcveg 421 mveifdmlla tssrfrmmnl qgeefvclks iillnsgvyt flsstlksle ekdhihrvld 481 kitdtlihlm akagltlqqq hqrlaqllli lshirhmsnk gmehlysmkc knvvplydll 541 lemldahrlh aptsrggasv eetdqshlat agstsshslq kyyitgeaeg fpatv
```

By "Estrogen receptor alpha (ER alpha, ER-α) nucleic acid molecule" is meant a polynucleotide or fragment thereof that encodes an ER alpha polypeptide. An exemplary ER alpha nucleic acid sequence is provided at NCBI Accession No. NM_000125.3 and shown below.

(SEQ ID NO: 9)

```
   1 aggagctggc ggagggcgtt cgtcctggga ctgcacttgc tcccgtcggg tcgcccggct
  61 tcaccggacc cgcaggctcc cggggcaggg ccggggccag agctcgcgtg tcggcgggac
 121 atgcgctgcg tcgcctctaa cctcgggctg tgctcttttt ccaggtggcc cgccggtttc
 181 tgagccttct gccctgcggg gacacggtct gcaccctgcc cgcggccacg gaccatgacc
 241 atgaccctcc acaccaaagc atctgggatg ccctactgc atcagatcca agggaacgag
 301 ctggagcccc tgaaccgtcc gcagctcaag atcccctgg agcggcccct gggcgaggtg
 361 tacctggaca gcagcaagcc cgccgtgtac aactaccccg agggcgccgc ctacgagttc
 421 aacgccgcgg ccgccgccaa cgcgcaggtc tacggtcaga ccggcctccc ctacggcccc
 481 gggtctgagg ctgcggcgtt cggctccaac ggcctggggg gtttcccccc actcaacagc
 541 gtgtctccga gcccgctgat gctactgcac ccgccgccgc agctgtcgcc tttcctgcag
 601 ccccacggcc agcaggtgcc ctactacctg gagaacgagc cagcggcta cacggtgcgc
 661 gaggccggcc cgccggcatt ctacaggcca aattcagata tcgacgcca gggtggcaga
 721 gaaagattgg ccagtaccaa tgacaaggga agtatggcta tggaatctgc caaggagact
 781 cgctactgtg cagtgtgcaa tgactatgct tcaggctacc attatggagt ctggtcctgt
 841 gagggctgca aggccttctt caagagaagt attcaaggac ataacgacta tatgtgtcca
 901 gccaccaacc agtgcaccat tgataaaaac aggaggaaga ctgccaggc ctgccggctc
 961 cgcaaatgct acgaagtggg aatgatgaaa ggtgggatac gaaaagaccg aagaggaggg
1021 agaatgttga acacaagcg ccagagagat gatggggagg cagggggtga agtggggtct
1081 gctggagaca tgagagctgc caacctttgg ccaagcccgc tcatgatcaa acgctctaag
1141 aagaacagcc tggccttgtc cctgacggcc gaccagatgg tcagtgcctt gttggatgct
1201 gagccccca tactctattc cgagtatgat cctaccagac ccttcagtga agcttcgatg
1261 atgggcttac tgaccaacct ggcagacagg gagctggttc acatgatcaa ctgggcgaag
1321 agggtgccag gctttgtgga tttgaccctc catgatcagg tccaccttct agaatgtgcc
1381 tggctagaga tcctgatgat tggtctcgtc tggcgctcca tggagcaccc agggaagcta
1441 ctgtttgctc ctaacttgct cttggacagg aaccaggaa aatgtgtaga gggcatggtg
1501 gagatcttcg acatgctgct ggctacatca tctcggttcc gcatgatgaa tctgcaggga
1561 gaggagtttg tgtgcctcaa atctattatt ttgcttaatt ctggagtgta cacatttctg
1621 tccagcaccc tgaagtctct ggaagagaag gaccatatcc accgagtcct ggacaagatc
1681 acagacactt tgatccacct gatggccaag gcaggcctga ccctgcagca gcagcaccag
1741 cggctggccc agctcctcct catcctctcc cacatcaggc acatgagtaa caaaggcatg
1801 gagcatctgt acagcatgaa gtgcaagaac gtggtgcccc tctatgacct gctgctggag
1861 atgctggacg cccaccgcct acatgcgccc actagccgtg aggggcatc cgtggaggag
1921 acggaccaaa gccacttggc cactgcgggc tctacttcat cgcattcctt gcaaaagtat
1981 tacatcacgg gggaggcaga gggtttccct gccacggtct gagagctccc tggctcccac
2041 acggttcaga taatccctgc tgcatttta cctcatcatg caccactta gccaaattct
2101 gtctcctgca tacactccgg catgcatcca acaccaatgg ctttctagat gagtggccat
2161 tcatttgctt gctcagttct tagtggcaca tcttctgtct tctgttggga acagccaaag
2221 ggattccaag gctaaatctt tgtaacagct ctctttcccc cttgctatgt tactaagcgt
2281 gaggattccc gtagctcttc acagctgaac tcagtctatg ggttggggct cagataactc
2341 tgtgcattta agctacttgt agagacccag gcctggagag tagacatttt gcctctgata
```

-continued

```
2401 agcactttt  aaatggctct  aagaataagc  cacagcaaag  aatttaaagt  ggctccttta
2461 attggtgact  tggagaaagc  taggtcaagg  gtttattata  gcaccctctt  gtattcctat
2521 ggcaatgcat  ccttttatga  aagtggtaca  ccttaaagct  tttatatgac  tgtagcagag
2581 tatctggtga  ttgtcaattc  attccccta   taggaataca  aggggcacac  agggaaggca
2641 gatcccctag  ttggcaagac  tatttaact   tgatacactg  cagattcaga  tgtgctgaaa
2701 gctctgcctc  tggctttccg  gtcatgggtt  ccagttaatt  catgcctccc  atggacctat
2761 ggagagcagc  aagttgatct  tagttaagtc  tccctatatg  agggataagt  tcctgatttt
2821 tgtttttatt  tttgtgttac  aaaagaaagc  cctccctccc  tgaacttgca  gtaaggtcag
2881 cttcaggacc  tgttccagtg  ggcactgtac  ttggatcttc  ccggcgtgtg  tgtgccttac
2941 acagggtga   actgttcact  gtggtgatgc  atgatgaggg  taaatggtag  ttgaaaggag
3001 caggggccct  ggtgttgcat  ttagccctgg  ggcatggagc  tgaacagtac  ttgtgcagga
3061 ttgttgtggc  tactagagaa  caagaggaa   agtagggcag  aaactggata  cagttctgag
3121 gcacagccag  acttgctcag  ggtggccctg  ccacaggctg  cagctaccta  ggaacattcc
3181 ttgcagaccc  cgcattgccc  tttggggtg   ccctgggatc  cctggggtag  tccagctctt
3241 cttcatttcc  cagcgtggcc  ctggttggaa  gaagcagctg  tcacagctgc  tgtagacagc
3301 tgtgttccta  caattggccc  agcaccctgg  ggcacgggag  aagggtgggg  accgttgctg
3361 tcactactca  ggctgactgg  ggcctggtca  gattacgtat  gccccttggtg gtttagagat
3421 aatccaaaat  cagggtttgg  tttggggaag  aaaatcctcc  cccttcctcc  cccgccccgt
3481 tccctaccgc  ctccactcct  gccagctcat  ttccttcaat  ttcctttgac  ctataggcta
3541 aaaagaaag   gctcattcca  gccacaggc   agccttccct  gggcctttgc  ttctctagca
3601 caattatggg  ttacttcctt  tttcttaaca  aaaagaatg   tttgatttcc  tctgggtgac
3661 cttattgtct  gtaattgaaa  ccctattgag  aggtgatgtc  tgtgttagcc  aatgacccag
3721 gtgagctgct  cgggcttctc  ttggtatgtc  ttgtttggaa  aagtggattt  cattcatttc
3781 tgattgtcca  gttaagtgat  caccaaagga  ctgagaatct  gggagggcaa  aaaaaaaaa
3841 aaagttttta  tgtgcactta  aatttgggga  caatttatg   tatctgtgtt  aaggatatgt
3901 ttaagaacat  aattctttg   ttgctgtttg  tttaagaagc  accttagttt  gtttaagaag
3961 caccttatat  agtataatat  atattttttt  gaaattacat  tgcttgttta  tcagacaatt
4021 gaatgtagta  attctgttct  ggatttaatt  tgactgggtt  aacatgcaaa  aaccaaggaa
4081 aaatatttag  tttttttttt  tttttttgta  tacttttcaa  gctaccttgt  catgtataca
4141 gtcatttatg  cctaaagcct  ggtgattatt  catttaaatg  aagatcacat  ttcatatcaa
4201 cttttgtatc  cacagtagac  aaaatagcac  taatccagat  gcctattgtt  ggatactgaa
4261 tgacagacaa  tcttatgtag  caaagattat  gcctgaaaag  gaaaattatt  cagggcagct
4321 aatttttgctt taccaaaat   atcagtagta  atattttgg   acagtagcta  atgggtcagt
4381 gggttctttt  taatgtttat  acttagattt  tcttttaaaa  aattaaaat   aaaacaaaaa
4441 aaaatttcta  ggactagacg  atgtaatacc  agctaaagcc  aaacaattat  acagtggaag
4501 gttttacatt  attcatccaa  tgtgtttcta  ttcatgttaa  gatactacta  catttgaagt
4561 gggcagagaa  catcagatga  ttgaaatgtt  cgcccagggg  tctccagcaa  ctttggaaat
4621 ctctttgtat  ttttacttga  agtgccacta  atggacagca  gatatttct   ggctgatgtt
4681 ggtattgggt  gtaggaacat  gatttaaaa   aaactcttg   cctctgcttt  ccccactct
4741 gaggcaagtt  aaaatgtaaa  agatgtgatt  tatctggggg  gctcaggtat  ggtggggaag
4801 tggattcagg  aatctgggga  atggcaaata  tattaagaag  agtattgaaa  gtatttggag
```

-continued

```
4861 gaaaatggtt aattctgggt gtgcaccagg gttcagtaga gtccacttct gccctggaga
4921 ccacaaatca actagctcca tttacagcca tttctaaaat ggcagcttca gttctagaga
4981 agaaagaaca acatcagcag taaagtccat ggaatagcta gtggtctgtg tttcttttcg
5041 ccattgccta gcttgccgta atgattctat aatgccatca tgcagcaatt atgagaggct
5101 aggtcatcca aagagaagac cctatcaatg taggttgcaa aatctaaccc ctaaggaagt
5161 gcagtctttg atttgatttc cctagtaacc ttgcagatat gtttaaccaa gccatagccc
5221 atgcctttg agggctgaac aaataaggga cttactgata atttactttt gatcacatta
5281 aggtgttctc accttgaaat cttatacact gaaatggcca ttgatttagg ccactggctt
5341 agagtactcc ttcccctgca tgacactgat tacaaatact ttcctattca tactttccaa
5401 ttatgagatg gactgtgggt actgggagtg atcactaaca ccatagtaat gtctaatatt
5461 cacaggcaga tctgcttggg gaagctagtt atgtgaaagg caaatagagt catacagtag
5521 ctcaaaaggc aaccataatt ctctttggtg caggtcttgg gagcgtgatc tagattacac
5581 tgcaccattc ccaagttaat ccctgaaaa cttactctca actggagcaa atgaactttg
5641 gtcccaaata tccatctttt cagtagcgtt aattatgctc tgtttccaac tgcatttcct
5701 ttccaattga attaaagtgt ggcctcgttt ttagtcattt aaaattgttt tctaagtaat
5761 tgctgcctct attatggcac ttcaattttg cactgtcttt tgagattcaa gaaaaatttc
5821 tattctttt tttgcatcca attgtgcctg aacttttaaa atatgtaaat gctgccatgt
5881 tccaaaccca tcgtcagtgt gtgtgtttag agctgtgcac cctagaaaca acatattgtc
5941 ccatgagcag gtgcctgaga cacagacccc tttgcattca cagagaggtc attggttata
6001 gagacttgaa ttaataagtg acattatgcc agtttctgtt ctctcacagg tgataaacaa
6061 tgcttttgt gcactacata ctcttcagtg tagagctctt gttttatggg aaaaggctca
6121 aatgccaaat tgtgtttgat ggattaatat gccctttgc cgatgcatac tattactgat
6181 gtgactcggt tttgtcgcag ctttgctttg tttaatgaaa cacacttgta aacctctttt
6241 gcactttgaa aagaatcca gcgggatgct cgagcacctg taaacaattt tctcaaccta
6301 tttgatgttc aaataaagaa ttaaactaaa
```

By "human epidermal growth factor receptor 2 (HER2) polypeptide" is meant a protein or fragment thereof having at least 85% homology to the sequence provided at NCBI Accession No. NP_004439.2 and having EGF binding activity. An exemplary amino acid sequence is provided below.

(SEQ ID NO: 10)

```
  1 melaalcrwg lllallppga astqvctgtd mklrlpaspe thldmlrhly qgcqvvqgnl
 61 eltylptnas lsflqdiqev qgyvliahnq vrqvplqrlr ivrgtqlfed nyalavldng
121 dplnnttpvt gaspgglrel qlrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtqr cekcskpcar vcyglgmehl revravtsan
361 iqefagckki fgslaflpes fdgdpasnta plqpeqlqvf etleeitgyl yisawpdslp
421 dlsvfqnlqv irgrilhnga ysltlqglgi swlglrslre lgsglalihh nthlcfvhtv
481 pwdqlfrnph qallhtanrp edecvgegla chqlcarghc wgpgptqcvn csqflrgqec
541 veecrvlqgl preyvnarhc lpchpecqpq ngsvtcfgpe adqcvacahy kdppfcvarc
601 psgvkpdlsy mpiwkfpdee gacqpcpinc thscvdlddk gcpaeqrasp ltsiisavvg
```

```
 661 illvvvlgvv fgilikrrqq kirkytmrrl lqetelvepl tpsgampnqa qmrilketel 721 rkvkvlgsga fgtvykgiwi pdgenvkipv aikvlrents pkankeilde ayvmagvgsp 781 yvsrllgicl tstvqlvtql mpygclldhv renrgrlgsq dllnwcmqia kgmsyledvr 841 lvhrdlaarn vlvkspnhvk itdfglarll dideteyhad ggkvpikwma lesilrrrft 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag gmvhhrhrss strsgggdlt lglepseeea prsplapseg 1081 agsdvfdgdl gmgaakglqs lpthdpsplq rysedptvpl psetdgyvap ltcspqpeyv 1141 nqpdvrpqpp spregplpaa rpagatlerp ktlspgkngv vkdvfafgga venpeyltpq 1201 ggaapqphpp pafspafdnl yywdqdpper gappstfkgt ptaenpeylg ldvpv
```

By "human epidermal growth factor receptor 2 (HER2) nucleic acid molecule" is meant a polynucleotide or fragment thereof that encodes a HER2 polypeptide. An exemplary HER2 nucleic acid sequence is provided at NCBI Accession No. NM_004448.3 and shown below.

(SEQ ID NO: 11)

```
   1 gcttgctccc aatcacagga gaaggaggag gtggaggagg agggctgctt gaggaagtat
  61 aagaatgaag ttgtgaagct gagattcccc tccattggga ccggagaaac caggggagcc
 121 ccccgggcag ccgcgcgccc cttcccacgg ggccctttac tgcgccgcgc gcccggcccc
 181 caccccctcgc agcaccccgc gccccgcgcc ctcccagccg gtccagccg gagccatggg
 241 gccggagccg cagtgagcac catggagctg gcggccttgt gccgctgggg gctcctcctc
 301 gccctcttgc cccccggagc cgcgagcacc caagtgtgca ccggcacaga catgaagctg
 361 cggctccctg ccagtcccga gacccacctg gacatgctcc gccacctcta ccagggctgc
 421 caggtggtgc agggaaacct ggaactcacc tacctgccca ccaatgccag cctgtccttc
 481 ctgcaggata tccaggaggt gcagggctac gtgctcatcg ctcacaacca agtgaggcag
 541 gtcccactgc agaggctgcg gattgtgcga ggcacccagc tctttgagga caactatgcc
 601 ctggccgtgc tagacaatgg agacccgctg aacaatacca cccctgtcac aggggcctcc
 661 ccaggaggcc tgcgggagct gcagcttcga agcctcacag agatcttgaa aggaggggtc
 721 ttgatccagc ggaaccccca gctctgctac caggacacga ttttgtggaa ggacatcttc
 781 cacaagaaca accagctggc tctcacactg atagacacca accgctctcg ggcctgccac
 841 ccctgttctc cgatgtgtaa gggctcccgc tgctggggag agagttctga ggattgtcag
 901 agcctgacgc gcactgtctg tgccggtggc tgtgcccgct gcaaggggcc actgccact
 961 gactgctgcc atgagcagtg tgctgccggc tgcacgggcc ccaagcactc tgactgcctg
1021 gcctgcctcc acttcaacca cagtggcatc tgtgagctgc actgcccagc cctggtcacc
1081 tacaacacag acacgtttga gtccatgccc aatcccgagg gccggtatac attcggcgcc
1141 agctgtgtga ctgcctgtcc ctacaactac ctttctacgg acgtgggatc ctgcacccct
1201 gtctgccccc tgcacaacca agaggtgaca gcagaggatg gaacacagcg tgtgtgaaag
1261 tgcagcaagc cctgtgcccg agtgtgctat ggtctgggca tggagcactt gcgagaggtg
1321 agggcagtta ccagtgccaa tatccaggag tttgctggct gcaagaagat ctttgggagc
1381 ctggcatttc tgccggagag ctttgatggg gacccagcct ccaacactgc ccgctccag
1441 ccagagcagc tccaagtgtt tgagactctg aagagatca caggttacct atacatctca
1501 gcatggccgg acagcctgcc tgacctcagc gtcttccaga acctgcaagt aatccgggga
1561 cgaattctgc acaatggcgc ctactcgctg acccctgcaag ggctgggcat cagctggctg
1621 gggctgcgct cactgaggga actgggcagt ggactggccc tcatccacca taacacccac
1681 ctctgcttcg tgcacacggt gcctgggac cagctctttc ggaacccgca ccaagctctg
1741 ctccacactg ccaaccggcc agaggacgag tgtgtgggcg agggcctggc ctgccaccag
1801 ctgtgcgccc gagggcactg ctggggtcca gggcccaccc agtgtgtcaa ctgcagccag
1861 ttccttcggg gccaggagtg cgtggaggaa tgccgagtac tgcagggct ccccagggag
1921 tatgtgaatg ccaggcactg tttgccgtgc caccctgagt gtcagcccca gaatggctca
1981 gtgacctgtt ttggaccgga ggctgaccag tgtgtggcct gtgcccacta taaggaccct
2041 cccttctgcg tggcccgctg ccccagcggt gtgaaacctg acctctccta catgcccatc
2101 tggaagtttc cagatgagga gggcgcatgc cagccttgcc ccatcaactg cacccactcc
2161 tgtgtggacc tggatgacaa gggctgcccc gccgagcaga gagccagccc tctgacgtcc
2221 atcatctctg cggtggttgg cattctgctg gtcgtggtct tggggtggt ctttgggatc
2281 ctcatcaagc gacggcagca gaagatccgg aagtacacga tgcggagact gctgcaggaa
2341 acggagctgg tggagccgct gacacctagc ggagcgatgc caaccaggc gcagatgcgg
```

-continued

```
2401 atcctgaaag agacggagct gaggaaggtg aaggtgcttg gatctggcgc ttttggcaca 2461 gtctacaagg gcatctggat ccctgatggg gagaatgtga aaattccagt ggccatcaaa 2521 gtgttgaggg aaaacacatc ccccaaagcc aacaaagaaa tcttagacga agcatacgtg 2581 atggctggtg tgggctcccc atatgtctcc cgccttctgg gcatctgcct gacatccacg 2641 gtgcagctgg tgacacagct tatgccctat ggctgcctct tagaccatgt ccgggaaaac 2701 cgcggacgcc tgggctccca ggacctgctg aactggtgta tgcagattgc caaggggatg 2761 agctacctgg aggatgtgcg gctcgtacac agggacttgg ccgctcggaa cgtgctggtc 2821 aagagtccca accatgtcaa aattacagac ttcgggctgg ctcggctgct ggacattgac 2881 gagacagagt accatgcaga tgggggcaag gtgcccatca agtggatggc gctggagtcc 2941 attctccgcc ggcggttcac ccaccagagt gatgtgtgga gttatggtgt gactgtgtgg 3001 gagctgatga ctttggggc caaaccttac gatgggatcc cagcccggga gatccctgac 3061 ctgctggaaa aggggagcg gctgcccag ccccccatct gcaccattga tgtctacatg 3121 atcatggtca aatgttggat gattgactct gaatgtcggc caagattccg ggagttggtg 3181 tctgaattct cccgcatggc caggacccc cagcgctttg tggtcatcca gaatgaggac 3241 ttgggcccag ccagtccctt ggacagcacc ttctaccgct cactgctgga ggacgatgac 3301 atgggggacc tggtggatgc tgaggagtat ctggtacccc agcagggctt cttctgtcca 3361 gaccctgccc cgggcgctgg gggcatggtc caccacaggc accgcagctc atctaccagg 3421 agtggcggtg gggacctgac actagggctg gagccctctg aagaggaggc ccccaggtct 3481 ccactggcac cctccgaagg ggctggctcc gatgtatttg atggtgacct gggaatgggg 3541 gcagccaagg ggctgcaaag cctccccaca catgacccca gccctctaca gcggtacagt 3601 gaggacccca cagtacccct gccctctgag actgatggct acgttgcccc cctgacctgc 3661 agcccccagc ctgaatatgt gaaccagcca gatgttcggc cccagccccc ttcgccccga 3721 gagggccctc tgcctgctgc ccgacctgct ggtgccactc tggaaaggcc caagactctc 3781 tccccaggga agaatggggt cgtcaaagac gttttttgcct ttgggggtgc cgtggagaac 3841 cccgagtact tgacacccca gggaggagct gcccctcagc cccaccctcc tcctgccttc 3901 agcccagcct tcgacaacct ctattactgg gaccaggacc accagagcg gggggctcca 3961 cccagcacct tcaagggac acctacggca gagaacccag agtacctggg tctggacgtg 4021 ccagtgtgaa ccagaaggcc aagtccgcag aagccctgat gtgtcctcag ggagcaggga 4081 aggcctgact tctgctggca tcaagaggtg ggagggccct ccgaccactt ccaggggaac 4141 ctgccatgcc aggaacctgt cctaaggaac cttccttcct gcttgagttc ccagatggct 4201 ggaaggggtc cagcctcgtt ggaagaggaa cagcactggg gagtctttgt ggattctgag 4261 gccctgccca atgagactct agggtccagt ggatgccaca gcccagcttg gccctttcct 4321 tccagatcct gggtactgaa agccttaggg aagctggcct gagaggggaa gcggccctaa 4381 gggagtgtct aagaacaaaa gcgacccatt cagagactgt ccctgaaacc tagtactgcc 4441 cccatgagg aaggaacagc aatggtgtca gtatccaggc tttgtacaga gtgcttttct 4501 gtttagtttt tactttttt gttttgtttt tttaaagatg aaataaagac ccaggggag 4561 aatgggtgtt gtatggggag gcaagtgtgg ggggtccttc tccacaccca ctttgtccat 4621 ttgcaaatat attttggaaa acagctaaaa aaaaaaaaa aaa
```

By "progesterone-receptor (PR) polypeptide" is meant a protein or fragment thereof having at least 85% homology to the sequence provided at GenBank Accession No. AAA60081.1 having progesterone binding activity. An exemplary amino acid sequence is provided below.

```
                                                          (SEQ ID NO: 12)
  1 mtelkakgpr aphvaggpps pevgspllcr paagpfpgsq tsdtlpevsa ipisldgllf
 61 prpcqgqdps dektqdqqsl sdvegaysra eatrgaggss ssppekdsgl ldsvldtlla
121 psgpgqsqps ppacevtssw clfgpelped ppaapatqrv lsplmsrsgc kvgdssgtaa
181 ahkvlprgls parqlllpas esphwsgapv kpspqaaave veeedgsese esagpllkgk
241 pralggaaag ggaaavppga aaggvalvpk edsrfsaprv alveqdapma pgrsplattv
301 mdfihvpilp lnhallaart rqlledesyd ggagaasafa pprsspcass tpvavgdfpd
361 cayppdaepk ddayplysdf qppalkikee eegaeasars prsylvagan paafpdfplg
421 ppplpprat psrpgeaavt aapasasvss asssgstlec ilykaegapp qqgpfapppc
481 kapgasgcll prdglpstsa saaaagaapa lypalglngl pqlgyqaavl keglpqvypp
541 ylnylrpdse asqspqysfe slpqkiclic gdeasgchyg vltcgsckvf fkramegqhn
601 ylcagrndci vdkirrkncp acrlrkccqa gmvlggrkfk kfnkvrvvra ldavalpqpv
661 gvpnesqals qrftfspgqd iqlipplinl lmsiepdviy aghdntkpdt sssltslnq
721 lgerqllsvv kwskslpgfr nlhiddqitl iqyswmslmv fglgwrsykh vsgqmlyfap
781 dlilneqrmk essfyslclt mwqipqefvk lqvsqeeflc mkvllllnti pleglrsqtq
841 feemrssyir elikaiglrq kgvvsssqrf yqltklldnl hdlvkqlhly clntfiqsra
901 lsvefpemms eviaaqlpki lagmvkpllf hkk
```

By "progesterone-receptor (PR) nucleic acid molecule" is meant a polynucleotide or fragment thereof that encodes a PR polypeptide. An exemplary PR nucleic acid sequence is provided at GenBank: Accession No. AF016381.1 and shown below.

(SEQ ID NO: 13)

```
   1 ctgaccagcg ccgccctccc ccgcccccga cccaggaggt ggagatccct ccggtccagc
  61 cacattcaac acccactttc tcctccctct gccctatat  tcccgaaacc ccctcctcct
 121 tccctttcc  ctcctccctg gagacggggg aggagaaaag gggagtccag tcgtcatgac
 181 tgagctgaag gcaaagggtc cccgggctcc cacgtggcg  gcggcccgc  cctcccccga
 241 ggtcggatcc ccactgctgt gtcgcccagc cgcaggtccg ttcccgggga gccagacctc
 301 ggacaccttg cctgaagttt cggccatacc tatctccctg gacgggctac tcttccctcg
 361 gccctgccag ggacaggacc cctccgacga aagacgcag  gaccagcagt cgctgtcgga
 421 cgtggagggc gcatattcca gagctgaagc tacaagggt  gctggaggca gcagttctag
 481 tcccccagaa aaggacagcg gactgctgga cagtgtcttg gacactctgt ggcgccctc
 541 aggtcccggg cagagccaac ccagccctcc cgcctgcgag gtcaccagct cttggtgcct
 601 gtttggcccc gaacttcccg aagatccacc ggctgccccc gccacccagc gggtgttgtc
 661 cccgctcatg agccggtccg ggtgcaaggt tggagacagc tccgggacgg cagctgccca
 721 taaagtgctg ccccggggcc tgtcaccagc ccggcagctg ctgctcccgg cctctgagag
 781 ccctcactgg tccggggccc cagtgaagcc gtctccgcag gccgctgcgg tggaggttga
 841 ggaggaggat ggctctgagt ccgaggagtc tgcgggtccg cttctgaagg gcaaacctcg
 901 ggctctgggt ggcgcggcgg ctggaggagg agccgcggct gtcccgccgg gggcggcagc
 961 aggaggcgtc gccctggtcc ccaaggaaga ttcccgcttc tcagcgccca gggtcgccct
1021 ggtggagcag gacgcgccga tggcgcccgg gcgctcccg  ctggccacca cggtgatgga
1081 tttcatccac gtgcctatcc tgcctctcaa tcacgcctta ttggcagccc gcactcggca
1141 gctgctggaa gacgaaagtt acgacggcgg ggccgggct  gccagcgcct ttgccccgcc
1201 gcggagttca ccctgtgcct cgtccacccc ggtcgctgta ggcgacttcc ccgactgcgc
1261 gtacccgccc gacgccgagc ccaaggacga cgcgtaccct ctctatagcg acttccagcc
1321 gcccgctcta aagataaagg aggaggagga aggcgcggag gcctccgcgc gctccccgcg
1381 ttcctacctt gtggccggtg ccaacccccgc agccttcccg gatttcccgt tggggccacc
1441 gccccgctgc ccgccgcgag cgaccccatc cagacccggg gaagcggcgg tgacggccgc
1501 acccgccagt gcctcagtct cgtctgcgtc ctcctcgggg tcgaccctgg agtgcatcct
1561 gtacaaagcg gagggcgcgc cgccccagca gggcccgttc gcgccgccgc cctgcaaggc
1621 gccgggcgcg agcggctgcc tgctcccgcg ggacggcctg ccctccacct ccgcctctgc
1681 cgccgccgcc ggggcggccc ccgcgctcta ccctgcactc ggcctcaacg gctcccgca
1741 gctcggctac caggccgccg tgctcaagga gggcctgccg caggtctacc cgccctatct
1801 caactacctg aggccggatt cagaagccag ccagagccca caatacagct tcgagtcatt
1861 acctcagaag attttgttaa tctgtgggga tgaagcatca ggctgtcatt atggtgtcct
1921 tacctgtggg agctgtaagg tcttctttaa gagggcaatg gaagggcagc acaactactt
1981 atgtgctgga agaaatgact gcatcgttga taaaatccgc agaaaaaact gcccagcatg
2041 tcgccttaga aagtgctgtc aggctggcat ggtccttgga ggtcgaaaat ttaaaaagtt
2101 caataaagtc agagttgtga gagcactgga tgctgttgct ctcccacagc cattgggcgt
2161 tccaaatgaa agccaagccc taagccgag  attcactttt tcaccaggtc aagacataca
2221 gttgattcca ccactgatca acctgttaat gagcattgaa ccagatgtga tctatgcagg
2281 acatgacaac acaaaacctg acacctccag ttctttgctg acaagtctta atcaactagg
2341 cgagaggcaa cttctttcag tagtcaagtg gtctaaatca ttgccaggtt ttcgaaactt
```

```
-continued
2401 acatattgat gaccagataa ctctcattca gtattcttgg atgagcttaa tggtgtttgg 2461 tctaggatgg agatcctaca aacatgtcag tgggcagatg ctgtattttg cacctgatct 2521 aatactaaat gaacagcgga tgaaagaatc atcattctat tcattatgcc ttaccatgtg 2581 gcagatccca caggagtttg tcaagcttca agttagccaa gaagagttcc tctgtatgaa 2641 agtattgtta cttcttaata caattccttt ggaagggcta cgaagtcaaa cccagtttga 2701 ggagatgagg tcaagctaca ttagagagct catcaaggca attggtttga ggcaaaaagg 2761 agttgtgtcg agctcacagc gtttctatca acttacaaaa cttcttgata acttgcatga 2821 tcttgtcaaa caacttcatc tgtactgctt gaatacattt atccagtccc gggcactgag 2881 tgttgaattt ccagaaatga tgtctgaagt tattgctgca caattaccca agatattggc 2941 agggatggtg aaacccttc tctttcataa aaagtgaatg tcatctttt cttttaaaga 3001 attaaatttt gtgg
```

By "Vascular endothelial growth factor (VEGF) polypeptide" is meant a protein or fragment thereof having at least 85% homology to the sequence provided at NCBI Accession No. NP_001020537 having angiogenic activity. An exemplary amino acid sequence is provided below.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, 100%, 200%, 300% or more. In particular embodiments, an alteration in the level of a marker poly-

```
                                                           (SEQ ID NO: 14)
  1 mtdrqtdtap spsyhllpgr rrtvdaaasr gqgpepapgg gvegvgargv alklfvqllg 61 csrfggavvr ageaepsgaa rsassgreep qpeegeeeee keeergpqwr lgarkpgswt 121 geaavcadsa paarapqala rasgrggrva rrgaeesgpp hspsrrgsas ragpgraset 181 mnfllswvhw slalllylhh akwsqaapma egggqnhhev vkfmdvyqrs ychpietlvd 241 ifqeypdeie yifkpscvpl mrcggccnde glecvptees nitmqimrik phqgqhigem 301 sflqhnkcec rpkkdrarqe kksvrgkgkg qkrkrkksry kswsvyvgar cclmpwslpg 361 phpcgpcser rkhlfvqdpq tckcsckntd srckarqlel nertcrcdkp rr
```

By "Vascular endothelial growth factor (VEGF) nucleic acid molecule" is meant a polynucleotide or fragment thereof that encodes a VEGF polypeptide. An exemplary VEGF nucleic acid sequence is provided at GenBank: Accession No. AY500353.1 and shown below.

peptide is 2×, 3×, 4×, 5×, 10×, 20×, 30× or 100× greater than the level of marker present in a reference.

By "antibody" is meant any immunoglobulin polypeptide, or fragment thereof, having immunogen binding ability.

```
                                                           (SEQ ID NO: 15)
  1 atgaactttc tgctgtcttg ggtgcattgg agccttgcct tgctgctcta cctccaccat 61 gccaagtggt cccaggctgc acccatggca gaaggaggag ggcagaatca tcacgaagtg 121 gtgaagttca tggatgtcta tcagcgcagc tactgccatc caatcgagac cctggtggac 181 atcttccagg agtaccctga tgagatcgag tacatcttca gccatcctg tgtgccctg 241 atgcgatgcg ggggctgctg caatgacgag ggcctggagt gtgtgcccac tgaggagtcc 301 aacatcacca tgcagattat gcggatcaaa cctcaccaag ccagcacat aggagagatg 361 agcttcctac agcacaacaa atgtgaatgc agaccaaaga agatagagc aagacaagaa 421 atccctgtgg gccttgctca gagcggagaa agcatttgtt tgtacaagat ccgcagacgt 481 gtaaatgttc ctgcaaaaac acagactcgc gttgcaaggc gaggcagctt gagttaaacg 541 aacgtacttg aagatgtgac aagccgaggc ggtgatgaat g
```

By "agent" is meant any small molecule chemical compound, antibody, nucleic acid molecule, or polypeptide, or fragments thereof.

"Array" also termed "microarray" is meant a collection of capture molecules (e.g., nucleic acid molecules or polypeptides) from one or more organisms arranged on a solid support (for example, a chip, plate, or bead). In one embodiment, these nucleic acid molecules or polypeptides may be arranged in a grid where the location of each nucleic acid molecule or polypeptide remains fixed to aid in identification of the individual nucleic acid molecules or polypeptides. In one embodiment, the array comprises a series of wells configured to receive a bead or beads.

The term "breast cancer" refers to primary breast or mammary tumors, as well as metastases of the primary breast tumors that may have settled anywhere in the body.

The term "breast cancer status" refers to the status of the disease in the patient. Examples of types of breast or mammary cancer statuses include, but are not limited to, the subject's risk of cancer, the presence or absence of disease, the stage of disease in a patient, and the effectiveness of treatment of disease.

By "biologic sample" is meant any tissue, cell, fluid, or other material derived from an organism. For example, tissue samples include cell samples and biopsy samples. Bodily fluids include but are not limited to, blood, blood serum, plasma, saliva, urine, peritoneal fluid, ascites, pleural effusions, and mammary cyst fluid.

By "capture molecule" or "capture reagent" is meant any polypeptide or polynucleotide capable of specifically binding a polypeptide of interest. In one embodiment, a capture molecule is an antibody the specifically binds a polypeptide marker of interest. In another embodiment, the capture molecule is a polynucleotide that hybridizes to a polynucleotide encoding a polypeptide marker of interest. In another embodiment, the capture molecule is an aptamer that specifically binds a polypeptide marker of interest.

As used herein, the terms "determining", "assessing", "assaying", "measuring" and "detecting" refer to both quantitative and qualitative determinations, and as such, the term "detecting" is used interchangeably herein with "assaying," "measuring," and the like.

By "reference" is meant a standard of comparison. For example, the CA 15-3, CA 19-9, CDKN2D, CYR61, ER alpha, HER2, PR, and/or VEGF polypeptide or polynucleotide level present in a patient sample may be compared to the level of said polypeptide or polynucleotide present in a corresponding healthy cell or tissue.

By "periodic" is meant at regular intervals. Periodic patient monitoring includes, for example, a schedule of tests that are administered daily, bi-weekly, bi-monthly, monthly, bi-annually, or annually.

A "biomarker" or "marker" as used herein generally refers to a protein, nucleic acid molecule, clinical indicator, or other analyte that is associated with a disease. In one embodiment, a marker of breast cancer is a polypeptide that is differentially present in a biological sample obtained from a subject having or at risk of developing breast cancer relative to a reference. A marker is differentially present if the mean or median level of the biomarker present in the sample is statistically different from the level present in a reference. A reference level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. Markers useful in the panels of the invention include, for example, CA 15-3, CA 19-9, CDKN2D, CYR61, ER alpha, HER2, PR, and/or VEGF proteins. Fragments useful in the methods of the invention are sufficient to bind an antibody that specifically recognizes the protein from which the fragment is derived. The invention includes markers that are substantially identical to the following sequences. Preferably, such a sequence is at least 85%, 90%, 95% or even 99% identical at the amino acid level or nucleic acid to the sequence used for comparison. In other embodiments, a marker of the invention is the age of the subject.

By "immunological assay" is meant an assay that relies on an immunological reaction, for example, antibody binding to an antigen. Examples of immunological assays include ELISAs, Western blots, immunoprecipitations, and other assays known to the skilled artisan.

By "marker profile" is meant a characterization of the expression or expression level of two or more polypeptides or polynucleotides. In particular, the levels of one or more of the following polypeptide markers: CA 15-3, CA 19-9, CDKN2D, CYR61, ER alpha, HER2, PR, and/or VEGF.

By "multiplex assay" is meant an assay where two or more analytes are detected concurrently.

By "panel" is meant a collection of molecules. If desired, the panel is fixed to a solid substrate.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

By "specifically binds" is meant a compound (e.g., antibody) that recognizes and binds a molecule (e.g., polypeptide), but which does not substantially recognize and bind other molecules in a sample, for example, a biological sample.

The accuracy of a diagnostic test can be characterized using any method well known in the art, including, but not limited to, a Receiver Operating Characteristic curve ("ROC curve"). An ROC curve shows the relationship between sensitivity and specificity. Sensitivity is the percentage of true positives that are predicted by a test to be positive, while specificity is the percentage of true negatives that are predicted by a test to be negative. An ROC is a plot of the true positive rate against the false positive rate for the different possible cutpoints of a diagnostic test. Thus, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. The area under the ROC is a measure of test accuracy. The accuracy of the test depends on how well the test separates the group being tested into those with and without the disease in question. An area under the curve (referred to as "AUC") of 1 represents a perfect test. In embodiments, biomarkers and diagnostic methods of the present invention have an AUC greater than 0.50, greater than 0.60, greater than 0.70, greater than 0.80, or greater than 0.9.

Other useful measures of the utility of a test are positive predictive value ("PPV") and negative predictive value ("NPV"). PPV is the percentage of actual positives who test as positive. NPV is the percentage of actual negatives that test as negative.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural. Thus, for example, reference to "a biomarker" includes reference to more than one biomarker.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The term "including" is used herein to mean, and is used interchangeably with, the phrase "including but not limited to."

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1D provide calibration curve graphs for the assays described herein and a chart showing ELISA and multiplex Simoa limit of detection (LOD) results. FIG. 1A provides a graph showing the calibration curve for the three-plex assay for ER, PR, and CYR61. FIG. 1B provides a graph showing the calibration curve for the two-plex assays for CA 15-3 and CDKN2D. FIG. 1C provides a graph showing the calibration curve for the singleplex CA 19-9. Error bars depict standard deviation of triplicate measurements. Error bars smaller than the marker are not visible. FIG. 1D provides a chart listing the ELISA and multiplex Simoa LODs for each measured protein and the fold difference between the two.

FIGS. 2A-2I provide a series of graphs showing the concentrations of different protein biomarkers in healthy and breast cancer serum (FIGS. 2A-2H) and a table of p-value results from Mann-Whitney statistical analyses of various serum proteins (FIG. 2I). In FIGS. 2A-2H, each graph reflects measurements above the limit of detection, with the sample size (n) listed below each group. Listed concentrations account for the assay's dilution factor. The markers shown are ER (FIG. 2A), PR (FIG. 2B), CYR61 (FIG. 2C), CA 15-3 (FIG. 2D), CDKN2D (FIG. 2E), CA 19-9 (FIG. 2F), HER2 (FIG. 2G), and VEGF (FIG. 2H). FIG. 2I provides a table in showing the p value results from Mann-Whitney statistical analysis of serum protein concentrations in healthy, all breast cancer, early stage (Stage 0, I, II), hormone receptor positive (HR+), and triple negative breast cancer samples. Values in red indicate a significant difference between the two groups, with a p value<0.05.

FIG. 9A provides a graph showing the overall accuracy of Model 2 (Healthy vs Stage 0-II) plotted against the marker excluded from the model. FIG. 9B provides a chart showing the number of correctly assigned samples, the total number of samples, and the resulting accuracy listed for each marker exclusion scenario.

FIGS. 11A-11C illustrate Simoa HD-1 Discs (FIGS. 11A and 11B) and a scanning electron microscopy image (FIG. 11C). FIG. 11A shows a Sony DADC disc with 24 microwell arrays radially arranged. FIG. 11B shows a photographic close-up with the different liquid channel features labeled. FIG. 11C is a scanning electron microscopy (SEM) image of a single microwell array on a disc, with a single well pictured on the inset.

FIGS. 12A and 12B show a Multiplex Simoa assay scheme and an illustration of the enzymatic readout. FIG. 12A: Beads with different antibodies are combined into a single reaction vessel to undergo a Simoa assay. Each bead represents a different dye conjugated to the surface, or a different plex. FIG. 12B: The illustration of the enzymatic readout shows no difference between the plexes until it is decoded, showing which wells are contained each plex.

FIG. 13A shows the outside of the Simoa HD-1 Analyzer and FIG. 13B shows where the assay reagents and consumables are located inside the instrument. The wash and incubation rings, as well as the imaging module are shown.

DETAILED DESCRIPTION OF THE INVENTION

Figure 3:
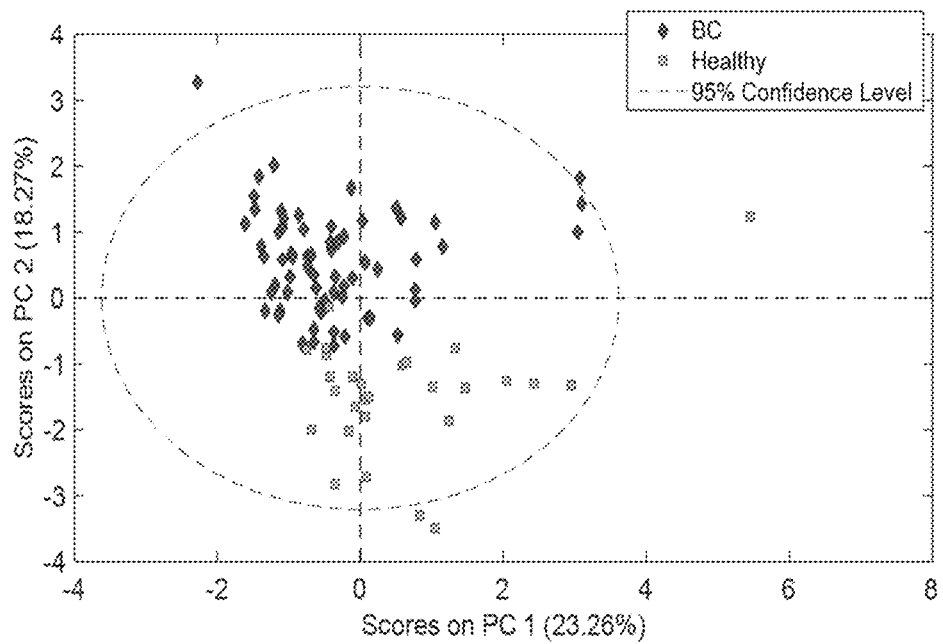
FIG. 3 provides a graph showing the principal component analysis biplot of scores along PC1 and PC2. All breast cancer samples are shown in dark gray, and healthy samples are shown in light gray. The 95% confidence level is shown as a dotted line.

The invention features compositions and methods that are useful for diagnosing breast cancer.

The invention is based, at least in part, on the discovery of a panel of biomarkers for detecting breast cancer. This panel of biomarkers includes one or more of the following markers: CA 15-3, CA 19-9, CDKN2D, CYR61, ER alpha, HER2, PR, and VEGF whose levels are altered in breast cancer. The present invention provides ultrasensitive immunoassays for detection of these biomarkers using single molecule array (Simoa) technology. More specifically, the markers were measured using a combination of single and multiplexed bead-based ultrasensitive assays on the Simoa HD-1 (Quanterix). When a healthy cohort was compared to the breast cancer group using these markers, a supervised predictive model was able to classify samples to the correct group with an overall accuracy of 95%. As described in detail below, these assays were demonstrated to have high analytical sensitivity for low abundance markers.

Conventional Methods for Detecting Breast Cancer

Breast cancer screening relies largely on imaging techniques such as mammography. Recent studies report that only approximately 29% of women are getting regular mammograms. Barriers to patient compliance with mammography include the time and inconvenience associated with the imaging, as well as anxiety and pain associated with the technique. The results of mammography are not consistently reliable. The reliability of the method varies with false positive and negative rates depending heavily upon the skill of the technician and the tissue density of the breast (which correlates with patient age). If mammography reveals a mass, or a palpable mass is discovered by a breast exam, the diagnostic process moves forward with additional imaging and a biopsy to obtain detailed size, spread, and biological information about the tumor. This process is invasive, expensive, and time-consuming.

A simple blood test would bypass the problem of variable sensitivity based on tissue density, as well as screening based on a visible or palpable tumor. Because a blood sample could be obtained by the primary care provider at the time of a patient visit, patient compliance with screening would likely increase. Furthermore, biological information could be obtained quickly and less invasively, without having to take tissue from the patient. Accordingly, the invention provides compositions and methods for detecting a biomarker signature in a serum sample that is likely to be useful for breast cancer screening, as well as identifying a molecular subtype, monitoring recurrence, or tracking therapeutic efficacy.

Circulating Biomarkers and Breast Cancer

Circulating biomarkers were introduced as a relatively noninvasive way to screen and track disease progression in cancer. Early stage tumors secrete small amounts of biomarkers into the bloodstream, and high analytical sensitivity may be necessary to detect these markers. The present invention provides ultrasensitive immunoassays for detection of a panel of biomarkers using a single molecule array (Simoa) technology. As described in detail below, these assays were demonstrated to have high analytical sensitivity for low abundance markers. This sensitivity has been shown to be advantageous in studies measuring PSA to track tumor growth and recurrence in prostate cancer, as these early changes were only detectable at levels below the Limit of Detection (LOD) of current "ultrasensitive" tests. This approach to prostate cancer work has now been extended to breast cancer biomarkers, where ultrasensitive singleplex protein assays were developed and tested in commercially available serum. These assays were 40-400× more sensitive than their bulk ELISA counterparts, and this sensitivity was important, since some measurements were below the LOD of standard ELISA. Individual biomarkers were then statistically evaluated to assess differences between healthy and breast cancer populations.

The present invention provides multiplex assays for detecting several proteins in serum simultaneously, which provides a useful diagnostic fingerprint for breast cancer. The proteins used for this signature include ER, PR, CYR61, CDKN2D, CA 15-3, CA 19-9, HER2, and VEGF. Clinical serum samples were tested with these assays and these measurements were compared to commercially available healthy controls. Each marker was individually evaluated for significant differences between subgroups within healthy and breast cancer cohorts. The protein markers and patient age were then used as inputs for a supervised classification technique to assess all of the markers as a signature to discriminate between healthy samples and different groups of breast cancer patients. The development of these predictive models, the results of their classifications, and implications for their potential diagnostic utility are described herein below.

Compositions and methods of the invention are useful for distinguishing stages of breast cancer. Characteristics of various stages are detailed below.

| Stage | Tumor | Node | Metastasis |
|---|---|---|---|
| Stage 0 | Tis | N0 | M0 |
| Stage IA | T1 | N0 | M0 |
| Stage IB | T0 | N1mi | M0 |
|  | TI | N1mi | M0 |
| Stage IIA | T0 | N1 | M0 |
|  | T1 | N1 | M0 |

-continued

| Stage | Tumor | Node | Metastasis |
|---|---|---|---|
|  | T2 | N0 | M0 |
| Stage IIB | T2 | N1 | M0 |
|  | T3 | N0 | M0 |
| Stage IIIA | T0 | N2 | M0 |
|  | T1 | N2 | M0 |
|  | T2 | N2 | M0 |
|  | T3 | N1 | M0 |
|  | T3 | N2 | M0 |

-continued

| Stage | Tumor | Node | Metastasis |
|---|---|---|---|
| Stage IIIB | T4 | N0 | M0 |
|  | T4 | N2 | M0 |
|  | T4 | N2 | M0 |
| Stage IIIC | Any T | N3 | M0 |
| Stage IV | Any T | Any N | M1 |

The AJCC defines specific diagnostic criteria for breast cancer, as shown below:

| | Primary tumor (T) | | Regional lymph nodes (N) |
|---|---|---|---|
| TX | Primary tumor cannot be assessed | NX | Regional lymph nodes cannot be assessed (e.g., previously removed) |
| T0 | No evidence of primary tumor | N0 | No regional lymph node metastasis |
| Tis | Carcinoma in situ | N1 | Metastasis to movable ipsilateral level I, II axillary lymph node(s) |
| Tis (DCIS) | Ductal carcinoma in situ | N2 | Metastases in ipsilateral level I, II axillary lymph nodes that are clinically fixed or matted or in clinically detected* ipsilateral internal mammary nodes in the absence of clinically evident axillary lymph node metastasis |
| Tis (LCIS) | Lobular carcinoma in situ | N2a | Metastases in ipsilateral level I, II axillary lymph nodes fixed to one another (matted) or to other structures |
| T1 | Tumor ≤20 mm in greatest dimension | N2b | Metastases only in clinically detected* ipsilateral internal mammary nodes and in the absence of clinically evident level I, II axillary lymph node metastases |
| T1mi | Tumor ≤1 mm in greatest dimension | N3 | Metastases in ipsilateral infraclavicular (level III axillary) lymph node(s), with or without level I, II axillary node involvement, or in clinically detected* ipsilateral internal mammary lymph node(s) and in the presence of clincially evident level I, II axillary lymph node metastasis; or metastasis in ipsilateral supraclavicular lymph node(s), with or without axillary or internal mammary lymph node involvement |
| T1a | Tumor >1 mm but ≤5 mm in greatest dimension | | |
| T1b | Tumor >5 mm but ≤10 mm in greatest dimension | N3a | Metastasis in ipsilateral infraclavicular lymph node(s) |
| T1c | Tumor >10 mm but ≤20 mm in greatest dimension | N3b | Metastasis in ipsilateral internal mammary lymph node(s) and axillary lymph node(s) |
| T2 | Tumor >20 mm but ≤50 mm in greatest dimension | N3c | Metastasis in ipsilateral supraclavicular lymph node(s) |
| T3 | Tumor >50 mm in greatest dimension | | Distant Metastasis (M) |
| T4 | Tumor of any size with direct extension to the chest wall and/or to the skin (ulceration or skin nodules) | M0 | No clinical or radiographic evidence of distant metastasis |
| T4a | Extension to chest wall, not including only pectoralis muscle adherence/invasion | cM0(i+) | No clinical or radiographic evidence of distant metastases, but deposits of molecularly or microscopically detected tumor cells in circulating blood, bone marrow, or other nonregional nodal tissue that are no larger than 0.2 mm in a patient without symptoms or signs of metastases |
| T4b | Ulceration and/or ipsilateral satellite nodules and/or edema (including peau d'orange) of the skin, which do not meet the criteria for inflammatory carcinoma | | |
| T4c | Both T4a and T4b | M1 | Distant detectable metastases as determined by classic clinical and radiographic means and/or histologically proven >0.2 mm |
| T4d | Inflammatory carcinoma | | |

Biomarkers

The diagnostic signature provided by the invention includes one, two, three, four, five, six, seven, or eight of the following biomarkers: Estrogen receptor (ER), CYR61, CDKN2D, CA 15-3, CA 19-9, HER2, and VEGF.

CYR61 is a secreted cysteine-rich signaling protein that acts as an angiogenic inducer that is linked to more aggressive cancer.

CA19-9 is a protein that has traditionally been used to monitor pancreatic cancer. It has also been found overexpressed in a number of breast cancers.

CA 15-3 is a membrane-bound mucin, which is overexpressed and aberrantly glycosylated in cancer patients, inducing cell growth and promoting metastasis.

CDKN2D functions as a cell growth regulator by preventing the activation of CDK kinases. CDKN2D has also been associated with sporadic breast cancer, specifically in triple negative breast patients.

ER-α (ER) is a hormone receptor protein that plays a role in reproductive physiology and bone remodeling. ER-α is ovexpressed in up to 75% of breast cancers PR is a hormone receptor protein that is overexpressed in up to 65% of breast cancer, and is associated with migration and invasion.

HER2 is a plasma membrane-bound receptor tyrosine kinase associated with cell proliferation and suppression of apoptosis. HER2 is overexpressed in 15-30% of breast cancers VEGF, or vascular endothelial growth factor, is an angiogenic cytokine that is overexpressed in breast cancer tissue. This marker is associated with the presence of solid tumors in other cancers such as brain, lung, and ovarian cancer.

Cyclin-dependent kinase inhibitor 2D (CDKN2D) is a cell cycle inhibitor that acts on CDK 4 and 6 kinases to prevent them interacting with Cyclin D. Cyclin D drives the transition between G1 and S phase in the cell cycle, which is when DNA replication occurs. In addition to cell cycle regulation, this protein has been found to respond to genotoxic stress, facilitating DNA repair.

The invention provides panels for distinguishing early stage breast cancer vs. a healthy subject in a biological sample of the subject, where the panel contains beads conjugated to capture molecules that specifically bind CYR61 and CDKN2D polypeptides. In another embodiment, the panel for distinguishing early stage breast cancer vs. a healthy subject in a biological sample of the subject contains beads conjugated to capture molecules that specifically bind ER, CYR61, CDKN2D, CA 15-3, and CA 19-9.

The invention provides a method for distinguishing early stage breast cancer vs. a healthy subject by detecting CYR61 and CDKN2D polypeptides or ER, CYR61, CDKN2D, CA 15-3, and CA 19-9 polypeptides and analyzing the presence of such polypeptide in combination with the age of the patient.

The invention provides a panel for distinguishing early stage (i.e., stage 0-2) vs. late (stage 3) breast cancer in a biological sample of the subject, where the panel contains beads conjugated to capture molecules that specifically bind CA 15-3, CA19-9 and PR.

The invention provides multiplex assays were developed for ER, PR, CDKN2D, CA 15-3, and CYR61. In one embodiment, the invention provides a 3-plex assay measuring ER, PR, and CYR61 simultaneously. In another embodiment, the invention provides a 2-plex assay for measuring CA 15-3 and CDKN2D simultaneously. In another embodiment, the invention provides a 2-plex assay for measuring HER2 and VEGF simultaneously.

Diagnostics

The present invention features assays for detecting breast cancer in a subject having altered levels of CA 15-3, CA 19-9, CDKN2D, CYR61, ER alpha, HER2, PR, and/or VEGF in a biological sample (e.g., plasma, serum) of the subject.

Figure 10:
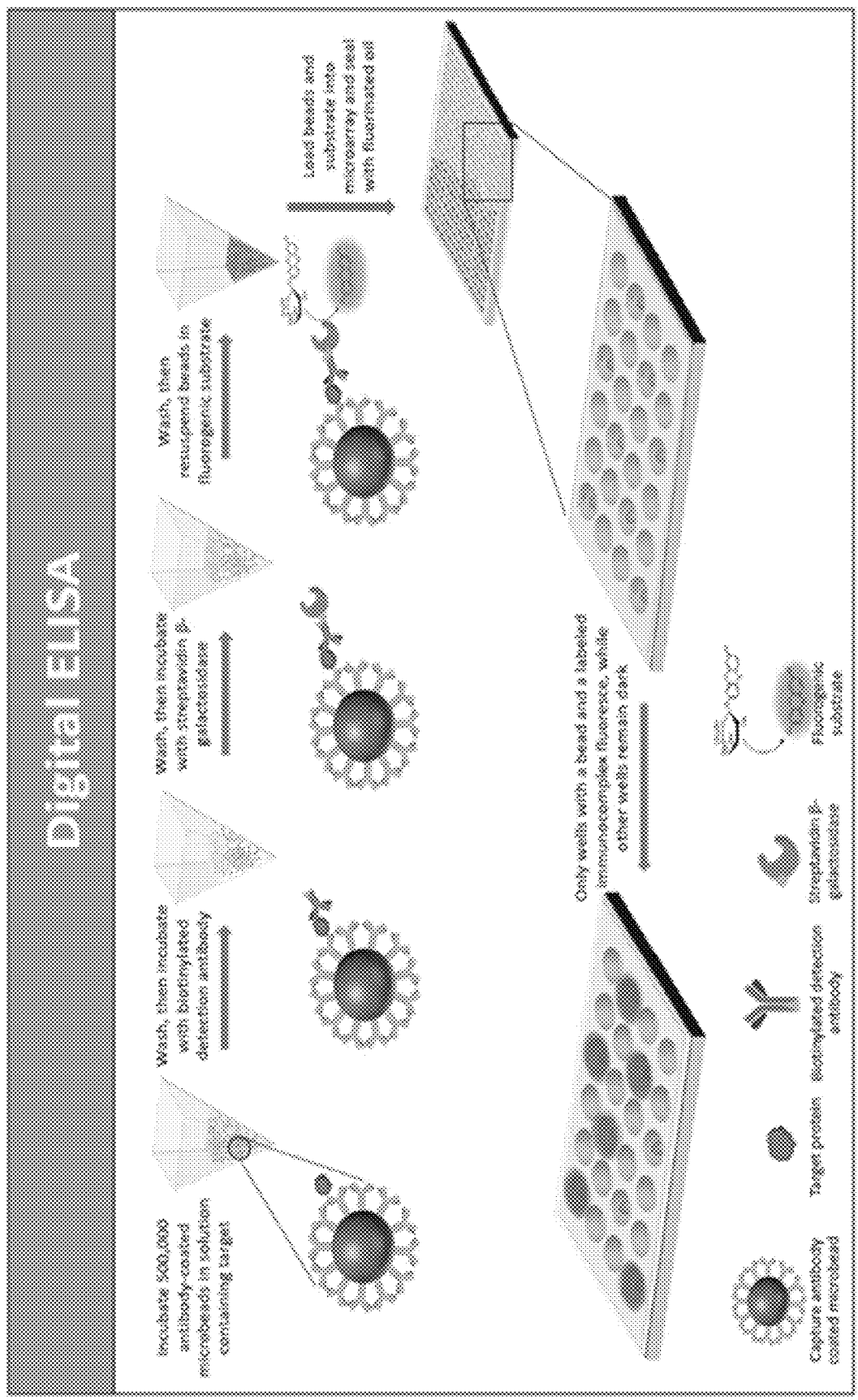
FIG. 10 provides a simplified schematic showing the biomarker microarray using antibody-coated microbeads and detection process via digital ELISA described herein.

Single Molecule Array (Simoa) assays are similar to traditional sandwich ELISA in that antibodies are used to capture and label proteins for subsequent detection via formation of an immunocomplex and production of a measurable signal. In Simoa assays, capture antibodies are covalently coupled to paramagnetic 2.7 μm beads and incubated with target protein in solution. There are several advantages to the bead-based platform: (1) the antibodies are covalently bound to the capture surface instead of physically adsorbed, so the antibody coating is stable during the assay, (2) the beads are stable for several months, so a single batch can be conjugated to antibody and stored for later usage, and (3) the bead suspension in solution allows for a more accessible capture surface for antigens, whereas a traditional plate ELISA is limited by the kinetics of the antigen traveling to a fixed planar surface. A biotinylated secondary detection antibody, which recognizes a different epitope on the target analyte than that of the capture antibody, is added to the solution and binds to the target analyte. After several washes, the beads are incubated with streptavidin-conjugated beta-galactosidase (SβG). The streptavidin on the enzyme binds to the biotin conjugated to the detection antibody during this incubation, and the beads are washed several times before they are re-suspended in fluorogenic substrate, resorufin-β-D-galactopyranoside (RGP). These assay steps are illustrated in FIG. 10.

The Simoa assay procedure diverges from standard methods when the bead and substrate suspension is taken from the reaction cuvette and loaded into the disc microarray via fluidics. Once the array is loaded, fluorocarbon oil is used to remove excess beads that did not load, and it seals the array. Wells containing a bead with an enzyme-labeled immunocomplex build a high local concentration of the fluorescent product over time as the enzymatic reaction progresses. A series of images are then taken of the array, and any the wells that contain a bead and an enzyme molecule will display fluorescence, while empty wells or those without an enzyme molecule will appear to be dark. The product generated from a single enzyme molecule is easily detectable because it is all kept in a 50 fL volume, which is 2 billion times smaller than the working volume of a standard ELISA.

Methods for carrying out Simoa are known in the art and are described, for example, in U.S. Pat. Nos. 9,482,662; 9,310,360; 9,110,025; 8,846,415; 8,415,171; 8,236,574; and 8,222,047; and in US Patent Publication Nos. 20160123969; 20150355182; 20150353997; 20140243223; 20110212462; 20100075862; 20100075439; 20100075407; and 20100075355, each of which is incorporated herein by reference.

Conventional methods may be used to measure levels of a CA 15-3, CA 19-9, CDKN2D, CYR61, ER alpha, HER2, PR, and/or VEGF polypeptide in a biological sample (e.g., plasma, serum). Biological samples include tissue samples (e.g., cell samples, biopsy samples) and bodily fluids, including, but not limited to, blood, blood serum, plasma, saliva, urine, peritoneal fluid and mammary cyst mammary cyst fluid, ascites, and pleural effusions. Exemplary methods for measuring altered levels of polypeptides include immunoassay, ELISA, western blotting and radioimmunoassay or other assays described herein. Altered levels of CA 15-3, CA 19-9, CDKN2D, CYR61, ER alpha, HER2, PR, and VEGF are considered as indicative of breast cancer (e.g., early stage, late stage). The alteration in CA 15-3, CA 19-9, CDKN2D, CYR61, ER alpha, HER2, PR, and VEGF levels may be by at least about 10%, 25%, 50%, 75% or more. In one embodiment, any alteration in the level of one or more markers of the invention relative to a control is indicative of breast cancer. In another embodiment, altered levels of CA 15-3, CA 19-9, CDKN2D, CYR61, ER alpha, HER2, PR, and/or VEGF are used to screen for breast cancer. Suitable controls indicate the levels present in a sample obtained from a healthy control subject.

Other commercially available methods include assays developed by Singulex which involve the use of a standard immunoassay, which is then detected using a laser detection tag. Such assays are described, for example, in US Patent Publication Nos. 20140342468 20130261009, 20130059400, and 20100329929, each of which is incorporated by reference in its entirety. Also, assays developed by Luminex, which are described, for example, in US Patent Publication Nos. 20160266103, 20160101421, 20140042366, 20120312085, 20100178709, 20090170214, 20070269345, and 20050118574, each of which is incorporated by reference in its entirety.

Successful practice of the invention can be achieved with one or a combination of methods that can detect and, if desired, quantify the markers. These methods include, without limitation, Simoa, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)n, atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry, where n is an integer greater than zero.

In particular embodiment, multiple markers selected from CA 15-3, CA 19-9, CDKN2D, CYR61, ER alpha, HER2, PR, and/or VEGF are measured, for example, in a multiplex assay. Expression levels of polypeptide markers are correlated with breast cancer disease status, and thus are useful in diagnosis. Antibodies that bind a polypeptide described herein, oligonucleotides or longer fragments derived from a nucleic acid molecule encoding such polypeptides, or any other method known in the art may be used to monitor expression of a polynucleotide or polypeptide of interest (e.g., CA 15-3, CA 19-9, CDKN2D, CYR61, ER alpha, HER2, PR, and/or VEGF). Detection of an alteration relative to a normal, reference sample can be used as a diagnostic indicator of breast cancer. In particular embodiments, the expression of a CA 15-3, CA 19-9, CDKN2D, CYR61, ER alpha, HER2, PR, and/or VEGF polypeptide is indicative of breast cancer or the propensity to develop breast cancer. In particular embodiments, a 2, 3, 4, 5, or 6-fold change in the level of a marker of the invention is indicative of breast cancer. In yet another embodiment, an expression profile that characterizes alterations in the expression of two or more markers is correlated with a particular disease state (e.g., breast cancer). Such correlations are indicative of breast cancer or the propensity to develop breast cancer. In one embodiment, a breast cancer can be monitored using the methods and compositions of the invention.

In one embodiment, the level of one or more markers is measured on at least two different occasions and an alteration in the levels as compared to normal reference levels over time is used as an indicator of breast cancer or the propensity to develop breast cancer. The level of marker in the biological sample (e.g., cell samples, biopsy sample, blood, blood serum, plasma, saliva, urine, peritoneal fluid, ascites, pleural effusions, and mammary cyst fluid) of a subject having breast cancer or the propensity to develop such a condition may be altered by as little as 10%, 20%, 30%, or 40%, or by as much as 50%, 60%, 70%, 80%, or 90% or more relative to the level of such marker in a normal control. In general, levels of CA 15-3, CA 19-9, CDKN2D, CYR61, ER alpha, HER2, PR, and/or VEGF are compared to levels of these markers in a healthy subject (i.e., those who do not have and/or who will not develop breast cancer).

Microarrays

As reported herein, a number of markers (e.g., CA 15-3, CA 19-9, CDKN2D, CYR61, ER alpha, HER2, PR, and/or VEGF) have been identified that are associated with breast cancer. Methods for assaying the expression of these polypeptides are useful for characterizing breast cancer. In particular, the invention provides diagnostic methods and compositions useful for identifying a polypeptide expression profile that identifies a subject as having or having a propensity to develop breast cancer. Such assays can be used to measure an alteration in the level of a polypeptide.

The polypeptides and nucleic acid molecules of the invention are useful as hybridizable array elements in a microarray. The array elements are organized in an ordered fashion such that each element is present at a specified location on the substrate. Useful substrate materials include beads, membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

Protein Microarrays

Proteins (e.g., CA 15-3, CA 19-9, CDKN2D, CYR61, ER alpha, HER2, PR, and/or VEGF) may be analyzed using protein arrays. Such arrays are useful in high-throughput low-cost screens to identify alterations in the expression or post-translation modification of a polypeptide of the invention, or a fragment thereof. In particular, such microarrays are useful to identify a protein whose expression is altered in breast cancer.

The polypeptides of the invention or capture molecules that specifically bind to such polypeptides are useful as hybridizable array elements in a microarray. The array elements are organized in an ordered fashion such that each element is present at a specified location on a substrate. Useful substrate materials include beads, membranes, composed of paper, nylon or other materials, filters, chips, glass slides, and other solid supports.

In one embodiment, the invention provides Single Molecule Arrays (Simoa). The microarrays used in Simoa assays are composed of ~216,000 wells contained in a 3 mm×4 mm area. Each well is 4.25 μm in diameter and 3.25 μm deep, with 8 μm spacing from center to center. Each well is a total of ~46 fL in volume, which is large enough to fit a single 2.7 μm microsphere and a small volume of substrate. There are 24 arrays positioned radially in a 120 mm disc format (Sony DADC). The disc is comprised of two layers: one contains the arrays, while the other contains the fluidic channels. Both parts utilize injection molding based on DVD manufacturing—the array is composed of cyclic olefin polymer (COP) and the fluidic channels are made of the same material doped with 3% carbon black, giving the disc a black appearance, shown in FIGS. 11A, 11B, and 11C. The two parts are then laser bonded to create a single disc. The fluidic portion of the disc contains the inlet port, channel, and outlet, which allows the pipet to load and flow the beads, substrate, and fluorocarbon oil into the disc. The clear portion of the disc contains the arrays and is positioned closer to the imaging module below, such that the disc is loaded from the top and imaged from the bottom.

In other embodiments, proteins (e.g., antibodies that bind a marker of the invention) are spotted on a substrate using any convenient method known to the skilled artisan (e.g., by hand or by inkjet printer).

The protein microarray is hybridized with a detectable probe. Probes can include antibodies that bind a polypeptide marker described herein. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Nucleic Acid Microarrays

To produce a nucleic acid microarray, oligonucleotides derived from a nucleic acid molecule may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link polynucleotides or oligonucleotides to the surface of a substrate using a vacuum system, thermal, UV, mechanical or chemical bonding procedure.

A nucleic acid molecule may be used as a hybridization probe or aptamer. The nucleic acid molecules are used to probe a biological sample derived from a patient, preferably as a bodily fluid (e.g., blood, blood serum, plasma, saliva, urine, peritoneal fluid, mammary cyst fluid) or tissue sample (e.g. a tissue sample obtained by biopsy). For some applications, cultured cells or other tissue preparations may be used. The mRNA is isolated according to standard methods, and cDNA is produced and used as a template to make complementary RNA suitable for hybridization. Such methods are known in the art. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30 C., more preferably of at least about 37 C, and most preferably of at least about 42 C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30 C in 750 mM NaCl, 75 mM trisodium citrate, and 1% SDS. In a more preferred embodiment, hybridization will occur at 37 C. in 500 mM NaCl, 50 mM trisodium citrate, 1% SDS, 35% formamide, and 100 μg/ml denatured salmon sperm DNA (ssDNA). In a most preferred embodiment, hybridization will occur at 42 C in 250 mM NaCl, 25 mM trisodium citrate, 1% SDS, 50% formamide, and 200 μg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25 C, more preferably of at least about 42 C, and most preferably of at least about 68 C. In a preferred embodiment, wash steps will occur at 25 C in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a most preferred embodiment, wash steps will occur at 68 C in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct nucleic acid sequences simultaneously (e.g., Heller et al., Proc. Natl. Acad. Sci. 94:2150-2155, 1997). Preferably, a scanner is used to determine the levels and patterns of fluorescence.

Multiplex Assays

Multiplex assays work similarly to standard Simoa assays, but dye-encoded beads are utilized to detect multiple proteins simultaneously. Each bead type or "plex" has one of four fluorescent dyes coupled to its surface. The intensity at which each bead type fluoresces under certain wavelengths becomes a unique identifier. Each bead type is coated with capture antibodies to different proteins, and combined to perform a standard Simoa assay with pooled detection antibodies. The multiplex Simoa assay is then performed the same way as a standard singleplex assay, with the same fluorescence readout in the results. The beads in the array are then decoded in the image analysis based on the wavelength and fluorescence intensity of each bead subpopulation or plex, while the enzymatic readout provides the signal values for each individual protein assay. (FIGS. 12A and 12B).

Simoa HD-1 Automation

Figure 13A:
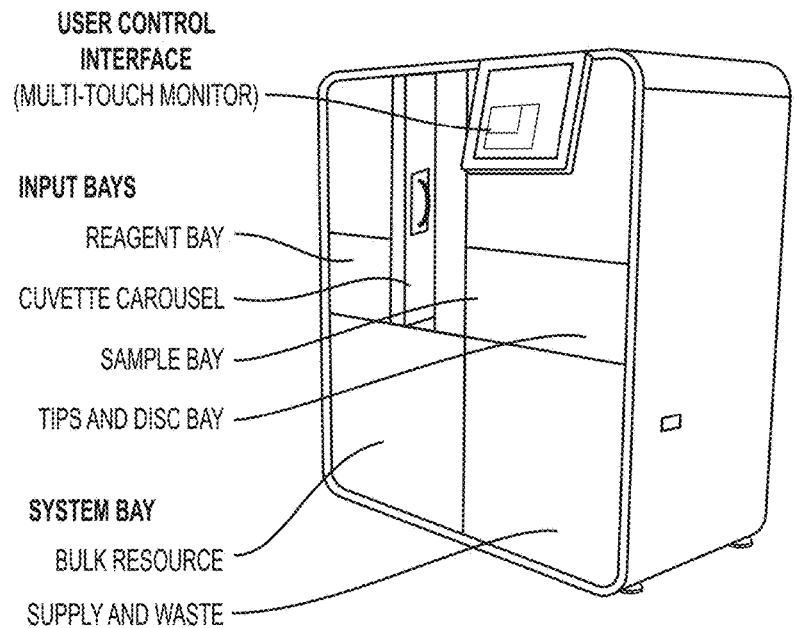
FIGS. 13A and 13B depict the aspects of the Simoa analyzer for performing the assays described herein.
Figure 13B:
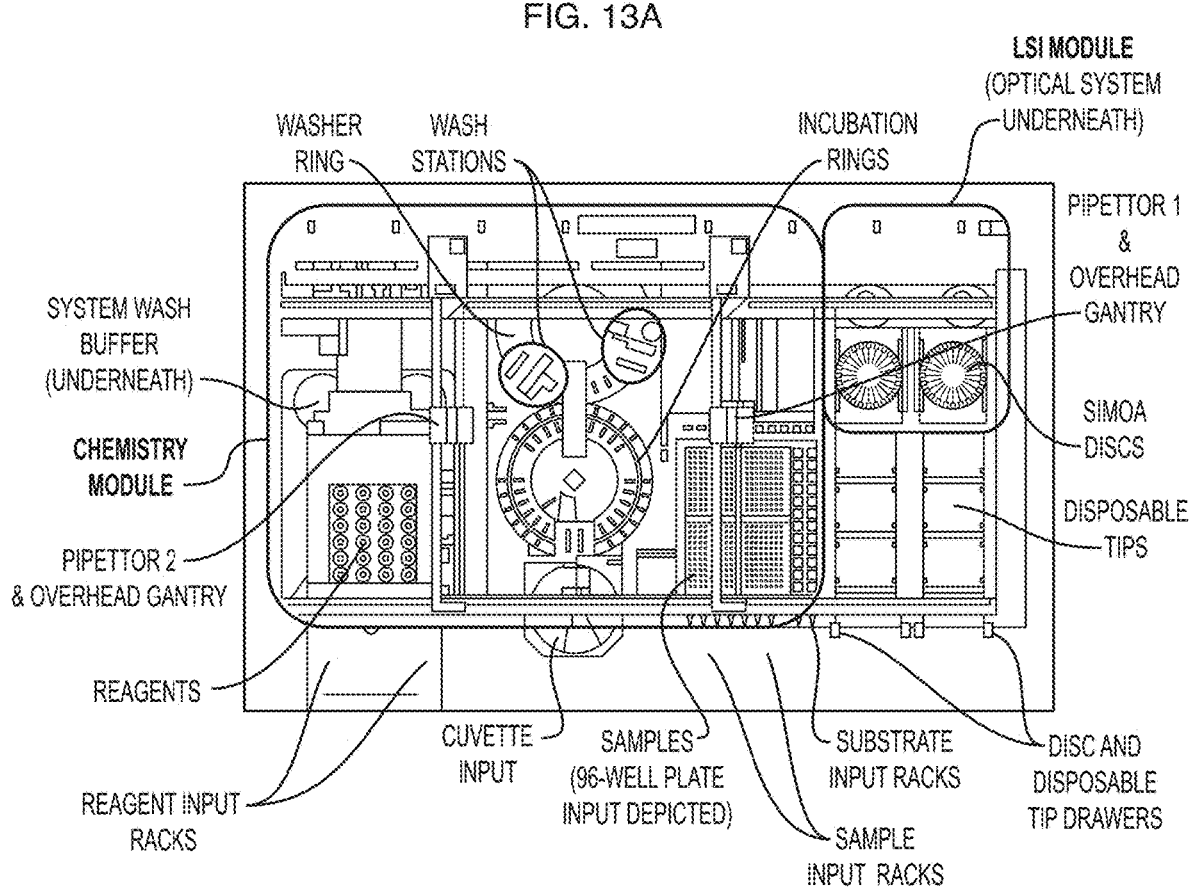

The Simoa assay process has been automated using the Simoa HD-1 Analyzer (Quanterix), pictured in FIGS. 13A and 13B. The instrument contains separate bays for loading assay reagents and 96-well plates with samples. Once the reagents and samples are programmed and loaded, two automated pipettors in the instrument are used to distribute user-programmed volumes of reagents and samples from their respective bays into individual cuvettes, where the binding steps of the assay take place. The incubation and wash steps are performed in two rings inside the instrument. The rotating incubation ring shakes the cuvettes to keep the beads suspended in solution, allowing the capture and detection reagents to interact with the sample. The rotating wash ring contains four wash stations and magnets that pellet the beads to the side of the cuvette, aspirates the solution, and re-disperses the beads by pipetting wash buffer directly toward the bead pellet. The wash buffer steps are all pre-programmed, and the instrument transfers sample cuvettes between the two rings based on the process needed. Following the incubation steps, the pipettor loads the beads into the disc arrays.

A major advantage provided by the automation is the high-throughput capability, with a steady-state usage capacity of 66 samples per hour. Additionally, the instrument schedules sequential sample processing in 45 second "cadences" such that each sample is treated identically. Variation between replicate measurements are often below 15% CV as a result of the instrument's precise pipetting and consistent timing.

Diagnostic Kits

The invention provides kits for detecting or monitoring breast cancer. In one embodiment, the kit includes a bead that is optionally conjugated to a capture molecule (e.g., antibody) that specifically binds CA 15-3, CA 19-9, CDKN2D, CYR61, ER alpha, HER2, PR, or VEGF. In other embodiments, the kit comprises microarrays suitable for use in a Simoa assay. In some embodiments, the kit comprises a sterile container, which contains the beads or microarrays; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired the kit is provided together with instructions for using the kit in a Simoa assay to diagnose breast cancer. The instructions will generally include information about the use of the composition for diagnosing a subject as having breast cancer or having a propensity to develop breast cancer. In other embodiments, the instructions include at least one of the following: description of the binding agent; warnings; indications; counter-indications; animal study data; clinical study data; and/or references. The instructions may be printed directly on the container (when present), or as a label applied to the container, or as a separate sheet, pamphlet, card, or folder supplied in or with the container.

Subject Monitoring

The disease state or treatment of a subject having breast cancer or a propensity to develop such a condition can be monitored using the methods and compositions of the invention. In one embodiment, the expression of markers (e.g., CA 15-3, CA 19-9, CDKN2D, CYR61, ER alpha, HER2, PR, or VEGF) present in a bodily fluid, such as blood, blood serum, plasma, saliva, urine, peritoneal fluid or mammary cyst fluid, is monitored. Such monitoring may be useful, for example, in assessing the efficacy of a particular drug in a subject or in assessing disease progression. Therapeutics that normalize the expression of a marker of the invention (e.g., CA 15-3, CA 19-9, CDKN2D, CYR61, ER alpha, HER2, PR, and/or VEGF) are taken as particularly useful in the invention. In one embodiment, a marker is "normalized" where it substantially returns to levels present in a health reference or present in an earlier stage of disease.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Multiplex assays were developed and optimized for ER, PR, CDKN2D, CA 15-3, and CYR61.

Example 1: Multiplex Assay Results

The multiplex assays were developed by combining singleplex assays tested on commercially available serum. These singleplex assays were combined and tested for cross-reactivity to assess whether the proteins, detection antibodies, or dye-encoded beads resulted in any biochemical crosstalk between assays. The calibration curves were then evaluated by looking at the background of the assay, the signal-to-noise ratio, limit of detection, and the dynamic range of the assay as compared to values in serum based on singleplex results. The multiplex calibration curves and LODs are shown in FIG. 1. The LODs for the three-plex proteins ER, PR, and CYR61 were 0.34 pg/mL, 0.23 pg/mL, and 0.019 pg/mL respectively. The two-plex assay LODs were 0.39 pg/mL for CDKN2D and 0.03 U/mL for CA 15-3, and the singleplex CA 19-9 assay LOD was 0.013 U/mL. The other two-plex assay for HER2 and VEGF had LODs of 0.40 pg/mL and 0.20 pg/mL, respectively. There was some loss of sensitivity and an increase in background for these assays when transitioning from singleplex to multiplex format, but the sensitivity appeared to be sufficient for these assays based on previous measurements in commercially available serum. The reagents and conditions used in these assays are described below.

Once the calibration curves were established, several experiments were performed to develop an assay suitable for protein detection in serum samples. Spike and recovery experiments were performed in commercially available healthy serum (BioreclamationIVT) to determine several factors for serum sample testing: (1) determine which sample and calibration diluents were compatible, (2) choose the appropriate dilution to maximize protein recovery and mitigate matrix effects, and (3) ensure that measured concentrations would fall within the assay's dynamic range. The assay reagents did not cross-react significantly in multiplex format, and the spike and recovery experiments led to the use of a 25% newborn calf serum, PBS-based diluent for both calibrators and serum samples.

Example 2: Serum Measurement Results

There were two sets of serum samples tested, one healthy, and one breast cancer. The healthy samples (n=28) were purchased from BioreclamationIVT. The donors were all female, with an age range of 32-53 years. The breast cancer group (n=66), comprised of women ages 37-90 years old who had been diagnosed with breast cancer, but had not undergone any therapeutic intervention at the time of blood donation. The majority of these patients were diagnosed at Stage I or II with hormone receptor-positive cancer, with eight patients in Stage III-IV disease and eight triple negative breast cancer (TNBC) patients.

The breast cancer and healthy serum samples were tested for eight different markers, with results for both cohorts shown FIG. 2. The box plots reflect the samples above the calculated limit of detection for the assay, and the concentrations listed account for the sample dilution factor. ER and PR had the lowest number of detectable samples out of all the markers. It may be possible to further improve the assay LOD for these markers. The other six assays were sensitive enough to measure serum levels of these proteins.

Although these markers were expected to be overexpressed in the serum of breast cancer patients, CYR61, CA 15-3, and VEGF were shown to be altered (i.e., significantly lower) in breast cancer patients (FIG. 2). CA 15-3 was already described to be a poor individual marker of early stage breast cancer; given that 58 out of the 66 samples are Stage II or earlier, it is no surprise that less than 25% of the detectable samples were above the healthy 35 U/mL threshold.[2,3] Furthermore, it may be important for CYR61 and VEGF to determine individual baseline concentrations for patients over time and monitor changes over the course of disease progression and treatment. These markers may prove to be more informative as part of a larger biomarker signature, rather than as individual markers.

The table in FIG. 2 compares individual marker expression in further stratified groups of breast cancer patients using Mann-Whitney statistics.[17] Healthy expression levels were compared to "early stage" or Stage 0 through Stage II patients, where ER, CYR61, CDKN2D, CA 15-3, and CA 19-9 were shown to be differentially expressed. This appears to be promising for a predictive signature for early-stage cancer. Subtype-specific expression was also examined to compare hormone receptor (HR+) cancer and TNBC samples. CDKN2D appeared to be the only marker differentially expressed, but there were only a total of eight TNBC samples in the breast cancer group.

Based on the preliminary statistical analysis of individual biomarkers, it appears that ER and PR are generally at relatively low levels in serum, but there is not enough sample information to determine whether the level of expression would be indicative of disease state. HER2 did not display any statistical difference between subgroups of patients. Furthermore, there were only three HER2 positive patients in the breast cancer population, and these patients were not taken into account when examining subtype groups. Individual statistical analyses of CYR61, CA 15-3, CDKN2D, and CA 19-9 show these markers to be useful for early breast cancer detection, based on the expression differences between groups.

Example 3: Multivariate Classification of Serum Samples

Multivariate analysis was used to evaluate all eight markers simultaneously as a signature for the identification and stratification of breast cancer serum samples. Several multivariate methods are available for analyzing complicated data, with the aim of either clustering or classifying data based on the given variables. Clustering is an unsupervised technique, which is an unbiased approach to grouping data without having corresponding class group for each data point. Classification is a supervised technique that uses the sample class as an input to train the algorithm, which can then be validated and utilized on unknown samples.

Example 4: Partial Least Squares-Discriminant Analysis (PLS-DA

Principal Component Analysis (PCA) is an unsupervised technique that was used to reduce the dimensionality of the dataset to facilitate a simpler analysis without losing important information. In this analysis, principal components of the data are identified in which the data has maximum variance, and allows for the data to be visualized differently and identify any underlying structure. Data imputation was also implemented by the software (PLS Toolbox, Eigenvector, Inc.) during the PCA process, where missing data points were replaced using the current model as a template. A total of seven data points were imputed in a 94×9 matrix consisting of 94 samples, breast cancer and healthy combined, and input variables (eight protein marker concentrations and patient age). Serum measurements that fell below the LOD for an assay were assigned a value at half the LOD, and accounted for the dilution factor of the assay. These assigned values allowed for undetectable serum samples to be included in the model with minimal bias.

Once the principal components were identified, PLS-DA (Partial Least Squares-Discriminant Analysis) was used to find latent variables, which are linear combinations of the original variables, to maximize covariance between y-variables. This analysis method is common in chemometrics, and has been used for the interpretation of complex microarray data and metabolomics data toward predicting diagnosis and clinical outcome of a disease state. PLS-DA in this case was used to assign samples to a class (such as "healthy" or "breast cancer") based on the input variables.

Before PCA and PLS analysis were performed, the data was treated in order to account for a large spread in data; for this dataset, the data was autoscaled. The cross-validation method used 80% of the sample set for calibration, while the remaining 20% was used for validation. The process was repeated until the entire sample set had been used for validation. The autoscaling, data imputation, and cross validation procedures were executed for each of the models tested, which are described below.

Example 5: Predictive Modeling Results

The first model tested compared healthy samples and all breast cancer samples. A graphical representation of the PCA is shown FIG. 3, showing scores along PC1 and PC2. The healthy samples are shown in green and the red samples are all of the breast cancer samples. The 95% confidence level is shown as a dotted circle. As this method is unsupervised, the group classification was not taken into account creating this model—the clustering was entirely based upon protein expression and ages of the patients. Though most of the variance is contained in PC1 by definition (23%), the separation between the two groups primarily occurs along the PC2 axis. There is some overlap between the breast cancer and healthy groups, but each group clusters differently. PCA was also used to examine outliers, but eliminating these samples did not make a significant difference in downstream analysis, thus all samples were retained for the prediction model.

There are several ways to describe a classification model. Sensitivity, specificity, and precision (also known as positive predictive value) are metrics by which models can be assessed. Sensitivity is defined as the number of true positives divided by the number of true positives and false negatives, describing the ability of the model to detect or classify all of the true positive samples in a group. In the case of healthy vs breast cancer samples, breast cancer is considered the "positive". Sensitivity is a similar metric that evaluates the model's performance in identifying all of the "negative" (or in this case healthy) samples. Precision, or positive predictive value takes true positives and false positives into account by evaluating what percentage of positive classifications predicted by the model were accurate. Overall accuracy is defined by the number of correct classifications (true positives and true negatives) divided by the total number of samples.

Figure 4:
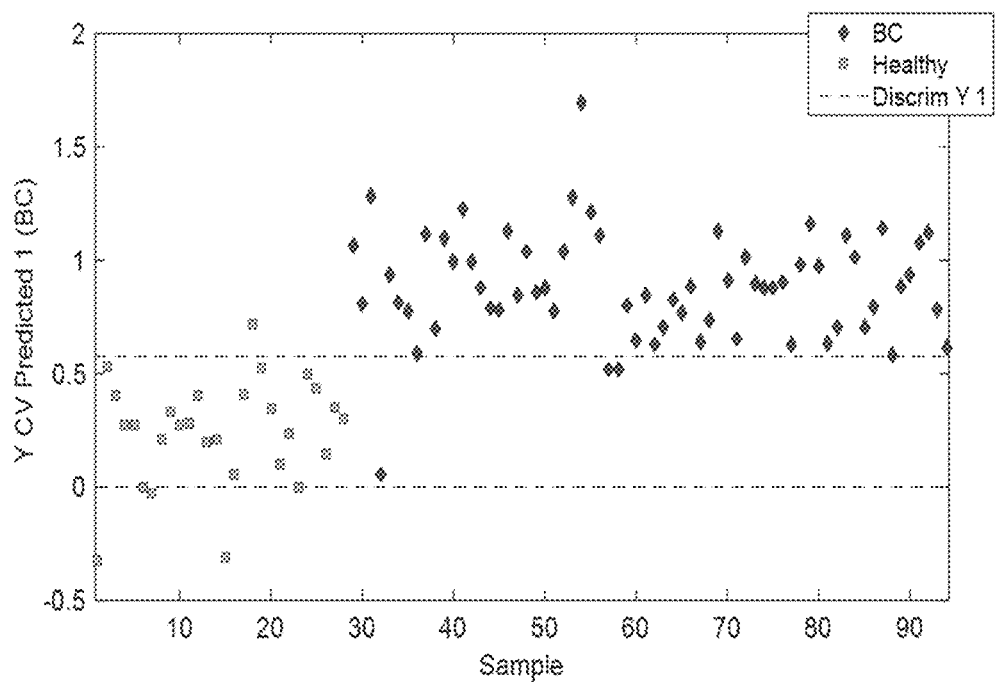
FIG. 4 provides a graph showing the partial least squares discriminant analysis of all breast cancer and healthy samples. Known healthy samples are light gray, while the breast cancer samples are shown in dark gray. The y-axis shows the y values returned by the cross-validation prediction of sample. The dotted red line shows the line of discrimination between predicted class groups. Samples on the other side of the discrimination line were misclassified in the cross validation.

PLS-DA was performed on all serum samples, with seven imputed data points and 122 undetectable measurements replaced with new values. FIG. 4 shows the classification results from the first model, comparing all breast cancer and healthy samples. Breast cancer samples are shown with dark gray diamonds, healthy samples are shown as light gray squares, and the line of discrimination between the two classes based on the model is shown as a=dotted line. Three of the 66 breast cancer samples were misclassified as healthy in the cross validation, a A common way of visualizing the sensitivity and specificity of a predictive model is a Receiver Operating Characteristic (ROC) curve. This curve plots sensitivity of the model against 1-specificity at different discrimination threshold settings. As the curve shifts to the top left quadrant of the plot or the (0,1) coordinate, the model is considered a better classifier. The diagonal line that spans from the origin to the (1,1) coordinate represents the threshold of no discrimination, where any points below this line would represents poor classifications (worse than random guessing). The area under the ROC curve, known as AUC, is used to quantify how proficient the model would be at discriminating positive and negative samples. An AUC value of 0.5 is a useless classifier, as it is no better than a random guess, while a score of 1 represents a perfect classifier. The PLS-DA models for the breast cancer serum samples will be described and evaluated using these classification terms.

Figure 5:
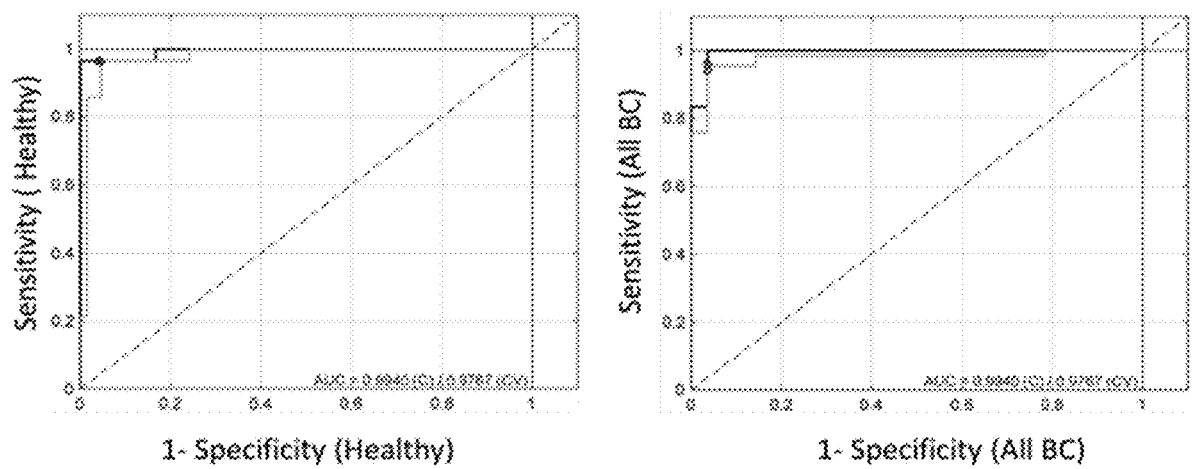
FIG. 5 provides a series of graphs showing Receiver Operating Characteristic (ROC) curves for Model 1 showing specificity and sensitivity for all healthy (n=28, left panel) and all breast cancer (n=66, right panel) serum samples based on patient age and an eight-protein signature. The circles on the curves mark the sensitivity and specificity at discrimination threshold values for the calibration and cross validation models, respectively. The Area Under the Curve (AUC) for the cross validated model is 0.98.

The first model compares all breast cancer and healthy samples, illustrated previously in FIG. 4. The ROC curves in FIG. 5 show a high degree of sensitivity for classifying both breast cancer and healthy samples, and breast cancer detection sensitivity at 95% and healthy sample detection sensitivity at 96%. The blue curve in the plot displays the results from the calibrated data, and the light gray line shows the data from the cross validation. The circles mark the threshold for discrimination in each model. The overall accuracy of the cross validated model is 96%, with an AUC value of 0.98.

Figure 6:
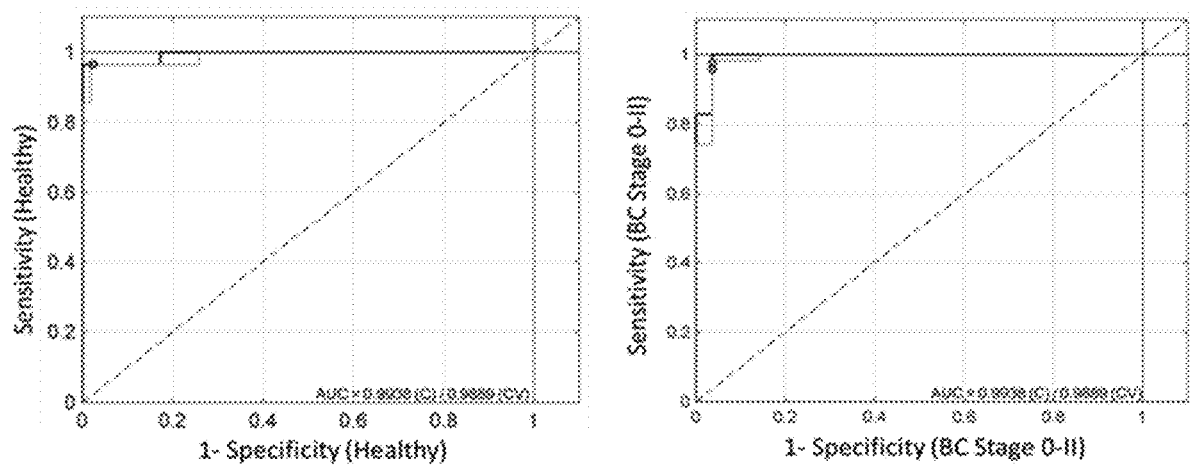
FIG. 6 provides a series of graphs showing Receiver Operating Characteristic (ROC) curves for Model 2 showing sensitivity and specificity for all healthy (n=28, left panel) and Stage 0-II breast cancer (n=58, right panel) serum samples based on patient age and an eight protein signature. The Area Under the Curve (AUC) for this model is 0.99. The circles on the curves mark the sensitivity and specificity at discrimination threshold values for the calibration and cross validation models, respectively FIG. 7 provides a series of graphs showing Receiver Operating Characteristic (ROC) curves for Model 3 showing sensitivity and specificity for Stage 0-II (n=58) breast cancer (left panel) and Stage III-IV breast cancer (n=8, right panel) serum samples based on patient age and an eight protein signature. The circles on the curves mark the sensitivity and specificity at discrimination threshold values for the calibration and cross validation models, respectively. The Area Under the Curve (AUC) for this model is 0.78.

The second model compares all of the healthy samples (n=28) to Stage 0-II breast cancer, which includes eight DCIS samples (Stage 0), 34 Stage I samples, and 16 Stage II samples. The ROC curves in FIG. 6 describe the results of this model; healthy samples were classified with a sensitivity of 96%, and breast cancer classification sensitivity was 97% these values are denoted by the circles on the light gray curves in each plot. Three samples were misclassified in total, with one false positive and two false negative samples. The AUC for this model is 0.99, with an overall accuracy of 97%. This model performed similarly to Model 1, which is expected given the overlap in sample class; the only data points excluded from this model were from eight Stage III-IV samples.

Figure 7:
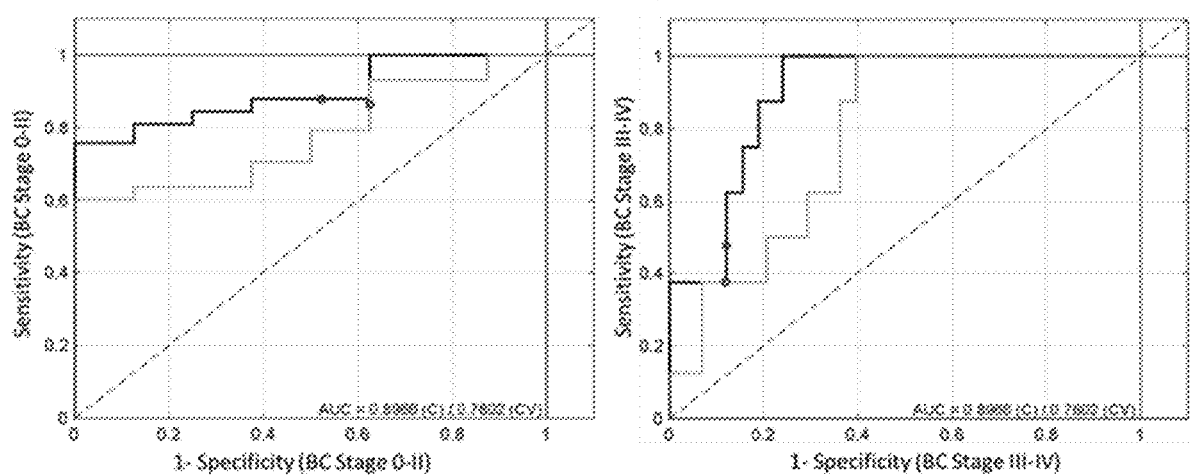

Model 3, illustrated in FIG. 7 compares Stage 0-II to Stage III-IV samples; Stage I-II samples were classified with a sensitivity of 88%, and Stage III-IV samples were classified with a sensitivity of 38%. The AUC for this model is 0.78, which does not perform as well as Model 1 or 2, but is still higher than the line of no discrimination. Seven of the 58 Stage I-II samples were misclassified, while five of the eight Stage III-IV samples were misclassified. Model 3 clearly classifies Stage 0-II samples with much higher sensitivity and precision than Stage and there is less agreement between the calibration and cross validation than in either Model 1 or 2.

Figure 8:
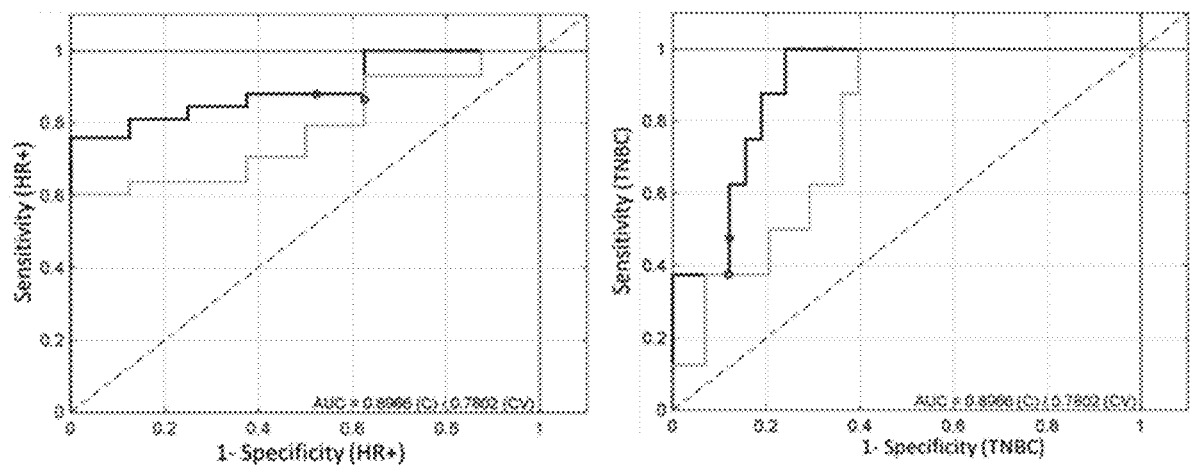
FIG. 8 provides a series of graphs showing Receiver Operating Characteristic (ROC) curves for Model 4 showing sensitivity and specificity for HR+(n=54) breast cancer (left panel) and triple negative breast cancer (n=8, right panel) serum samples based on patient age and an eight protein signature. The circles on the curves mark the sensitivity and specificity at discrimination threshold values for the calibration and cross validation models, respectively. The Area Under the Curve (AUC) for this model is 0.56.

Model 4 compares ER and/or PR positive (hormone receptor positive) samples (n=54) and triple negative breast cancer (TNBC) samples (n=8), shown in FIG. 8. This model is relevant to the diagnostic process, as treatment plan can be formulated to target one subtype of the disease, but can be ineffective for another subtype. The sensitivity for HR+ detection was 70%, with 38 of the 54 samples being classified correctly. The sensitivity for triple negative samples was 38%, with three of the eight TNBC samples correctly assigned. The AUC for this model is 0.56, which does not describe this model as a proficient classifier. The metrics of all four models are summarized in Table 1, including precision, sensitivity, AUC, and accuracy.

TABLE 1

Description of each PLS-DA model, with precision, true positive rate, AUC value, the number of samples in each group, and the overall accuracy.

| | Class Groups | Precision | True Positives | AUC | # Samples | Accuracy |
|---|---|---|---|---|---|---|
| Model 1 | Healthy | 90% | 96% | 0.98 | 28 | 96% |
| | All BC | 98% | 95% | | 66 | |
| Model 2 | Healthy | 93% | 96% | 0.99 | 28 | 97% |
| | BC Stage 0-II | 98% | 97% | | 58 | |

TABLE 1-continued

Description of each PLS-DA model, with precision,
true positive rate, AUC value, the number of samples
in each group, and the overall accuracy.

| | Class Groups | Precision | True Positives | AUC | # Samples | Accuracy |
|---|---|---|---|---|---|---|
| Model 3 | BC Stage 0-II | 91% | 88% | 0.78 | 58 | 82% |
| | BC Stage III-IV | 30% | 38% | | 8 | |
| Model 4 | HR + BC | 88% | 70% | 0.56 | 54 | 66% |
| | TNBC | 84% | 38% | | 8 | |

Figures 9A, 9B:
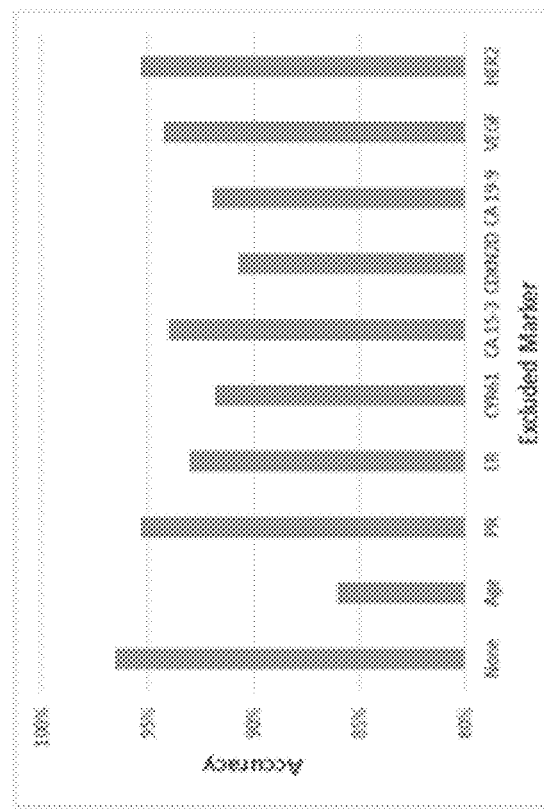
FIGS. 9A and 9B show a graph of accuracy versus excluded marker and a chart related to excluded markers and correct assignments in samples as described herein.

Individual contributions of each marker to the model were also evaluated by excluding one variable at a time and re-running the model. Each model had the same preprocessing and cross validation method, and the latent variable number with the best accuracy was chosen to represent that instance of the PLS-DA model. Model 2 (Healthy vs Stage 0-II) was chosen for this evaluation, since it displayed the highest accuracy and the largest AUC. The model assigned classes to samples with an overall 97% accuracy when all nine variables were included, and this accuracy declined to varying degrees when a single variable was excluded from the analysis. The largest change in accuracy occurred upon the exclusion of patient age, with a resulting accuracy of 86%. Age has been previously identified as a risk factor for breast cancer, so the impact on the model is reasonable. The protein markers with the most notable impact on the model were CDKN2D, CYR61, and CA 19-9. The accuracy of Model 2 decreased to 91% when CDKN2D was removed as a marker, and 92% when CYR61 and CA 19-9 were removed as markers. The other marker exclusions resulted in accuracy values ranging 93-95%. Detailed results of individual marker contributions to Model 2 are displayed in FIG. 9, summarizing the accuracy for each instance of the model.

The development and validation of three multiplex assays, for (a) CYR61, ER, and PR, (b) CA 15-3 and CDKN2D, (c) HER2 and VEGF is described herein. The CA 19-9 singleplex assay was used. These assays were all validated through cross-reactivity and spike and recovery experiments for serum measurements. Every Simoa assay displayed LODs lower than their ELISA counterparts. The serum samples used for assay testing consisted of serum taken from women who had positive mammogram and a positive diagnosis from a clinician. These newly diagnosed women had not yet undergone any therapeutic intervention at the time of sampling (n=66). Healthy serum controls from 28 females were purchased from a commercial source. The four assays were then used to test all 94 serum samples.

Initial investigation of the resulting data showed that the sensitivity achieved by Simoa was necessary in order to detect several biomarkers at low levels. Even with this heightened sensitivity, a number of samples were below the LOD for ER and PR. The dilution factor contributed to this need for sensitivity, but this also allowed for low volumes of serum (45-60 µL) to be consumed per assay. A total of 200 µL of serum were used to collect data on eight different protein markers. Statistical analysis of individual marker concentrations in serum showed CYR61, CA 19-9, CA 15-3, ER, and CDKN2D levels were correlated with the presence of early stage breast cancer compared to a healthy cohort. The other four markers showed no significant difference between healthy and breast cancer samples, nor did they distinguish between early and late stages in disease progression or subtype.

All of the data obtained for these serum samples were used as inputs to evaluate the combined utility of eight protein markers and patient age toward a breast cancer diagnostic signature. Four models were tested comparing healthy samples to all breast cancer samples, healthy and Stage 0-II samples, Stage 0-II and Stage III-IV samples, and HR+ and TNBC samples.

Model 1 compared all healthy cohorts to the entirety of the breast cancer cohort, a sensitivity and specificity of 95% and 96%, respectively. Model 1 displayed an overall accuracy of 96% and an AUC of 0.98, which describes a successful classifier. Model 2, which compared healthy samples to Stage 0-II breast cancer, performed slightly better with an overall of 97%, with sensitivity and specificity values at 97% and 96%, respectively. The metrics for both Model 1 and Model 2 show an improvement compared to the current gold standard in screening, mammography, which has 79% sensitivity and 90% specificity.[1] These results are promising for the development of a noninvasive screening test for breast cancer. Additionally, the variables with the highest impact on Model 2 were age, CDKN2D, CYR61, and CA 19-9 based on the exclusion of these markers from the models. These findings agree with the Mann-Whitney statistical evaluation of individual markers, which supports the use of such univariate statistics to help assess the utility of individual markers.

Model 3 evaluated the same biomarker signature to differentiate Stage 0-II and Stage III-IV breast cancer samples—this model demonstrated proficiency in classifying Stage 0-II samples with a sensitivity of 88%, but was less successful in identifying Stage which only had a sensitivity of 38%. The AUC for this model was 0.78, with 82% accuracy. Although Model 3 is not as successful as Model 1 and 2, the signature shows some promise for use in tracking disease progression. The most influential variables in this model were CA 15-3 and CA 19-9, which supports the idea that different markers in a signature could be used for different purposes (i.e. screening prior to mammography, therapeutic efficacy monitoring differential expression for return to healthy or early stage levels, recurrence monitoring monitoring for differential expression associated with return to early stage expression levels). Model 4 compared the hormone positive (HR+) population to the TNBC cohort, which performed poorly. Is model had an accuracy of 66% and an AUC of 0.56, which places this model slightly above the discrimination of a random guess. This signature does not appear to be appropriate for differentiating breast cancer subtypes. Out of the four models, the protein signature combined with patient age displayed the most discrimination between Stage 0-II breast cancer and healthy samples.

The high sensitivity and accuracy demonstrated by Models 1 and 2 are both promising and encouraging. There are several ways to improve upon this preliminary data, which focus on two aspects of the model: the biomarker assays and the tested samples. The ER and PR biomarker assays were not sensitive enough to detect half or more of the serum samples, and having these values may contribute to better discrimination in a stage-specific or disease-specific manner. In one embodiment, HIF1α is used to identify aggressive breast cancer as a circulating marker.

The models can also be improved by diversifying the sample pool further. The four models had an overwhelming majority of HR+, Stage I-II samples, so it is not surprising that, when trained on this set of data, the model identifies these samples with higher sensitivity and accuracy. Giving the model more data from aggressive, late-stage, and triple negative breast cancer cases may help train the model better, and thus allow it to identify these types of samples more accurately. The healthy cohort may also be improved upon by getting serum samples from women who have had negative mammograms. This type of cohort provides a better control for newly diagnosed women, and does not rely on self-reporting healthy patients, as was the case with the current healthy cohort.

The 66 samples tested in this work were chosen for the lack of therapeutic intervention, which avoided marker expression bias due to treatment. Samples outside of this group were classified "NED", or no evidence of disease detected. These should be tested with the eight-marker signature to find whether these samples would be classified as healthy. Additionally, there was a small group of serial timepoint samples that were taken from women who were diagnosed with breast cancer and underwent treatment. The serum taken from these patients at the time of diagnosis, treatment, and afterwards, contributes to the effort to create a test that tracks therapeutic efficacy. Overall, the current work has produced a biomarker signature that classified early breast cancer with an overall accuracy of 97%, and through this we have identified important predictive markers for cancer. Expanding the model further could prove useful for the diagnostic and prognostic aspects of breast cancer management.

The results described herein above, were obtained using the following methods and materials.

Bead Coupling

Approximately 100 µg of capture antibody is buffer exchanged into 50 mM MES, pH 6.2 using a 50 kDa, 0.5 mL Amicon Ultra centrifugal filter unit (Millipore), per the manufacturer's instructions. The concentration of the antibody is then measured using a Nanodrop ND-1000 Spectrophotometer (Nanodrop) and the volume is adjusted to 200 µL by adding MES. The final concentration of the capture antibody in this volume typically varies between 0.3 mg/mL and 0.5 mg/mL. Beads are prepared by transferring $2.8 \times 10^8$ paramagnetic carboxylated beads (Quanterix) into a conical 1.7 mL microcentrifuge tube. In the case of multiplex beads, the encoded beads are purchased with various dyes already conjugated to the surface (dyes listed below). The beads are washed by placing the tube on a magnetic separator, waiting for the beads to pellet, taking the supernatant out, resuspending the beads in buffer, vortexing the tube for five seconds, and centrifuging briefly. The beads are washed three times with 200 µL 1×PBS/1% Tween 20, then twice with cold MES. The final volume of the beads in MES is 190 µL. For multiplex beads, the final volume is 195 µL. The carboxylated beads are activated with EDC, or 1-ethyl-3-(3-dimethylaminopropyl)carbodiimide hydrochloride (Pierce Biotechnology). After dissolving 10 mg EDC in one mL of MES (10 mg/mL final concentration), 10 µL (5 µL for multiplex beads) of the EDC solution is added to the 190 or 195 µL bead solution. The bead solution is immediately placed on a microplate shaker (IKA) at 1000 rpm for 30 minutes in order to activate the bead surface for conjugation.

| Plex | Dye |
|------|-----|
| 488 | Alexa Fluor 488 (AF488) |
| 647 | Cyanine 5 Mono Hydrazide (Cy5) |
| 700 | Cyanine 5.5 (Cy5.5) |
| 750 | HiLyte Fluor 750 Hydrazide |

Dyes Coupled to Each Bead Plex in Simoa Multiplex Assays

After the 30 minute incubation, the beads are washed with 200 µL cold MES buffer and 200 µL of antibody solution, and then added to the beads and vortexed for 10 seconds. The bead solution is then placed back on the microplate shaker at 1000 rpm for two hours. After incubation, the supernatant is aspirated and placed into a separate microcentrifuge tube. The beads are washed twice with 1×PBS/1% Tween 20. The first of these washes is also saved in a separate microcentrifuge tube. 200 µL blocking buffer (1×PBS/1% BSA) is added to the beads, vortexed for five seconds, and placed on the microplate shaker for 30 minutes at 1000 rpm. After the blocking incubation, the beads are washed three times with 1×PBS/1% Tween 20, and twice with Bead Diluent Buffer (50 mM Tris buffer with Proclin, Quanterix). The beads are then transferred to a clean microcentrifuge tube and stored at 4° C. in bead diluent.

Bead Characterization

The antibody coupling efficiency is evaluated by measuring the antibody concentration in the saved supernatant and wash performed after the two hour coupling step. The Nanodrop ND-2000 (Nanodrop) was used to measure absorbance at 280 nm and calculate the amount of antibody in each solution. The total amount of antibody coupled to the beads is calculated by subtracting the amount of antibody in the washes from the original amount of antibody recovered from the buffer exchange.

The concentration and aggregation of the beads are characterized by using a Coulter Counter Z2 (Beckman Coulter). 10 µL of the coupled bead stock solution is pipetted into 10 mL of Zpak electrolyte buffer (Beckman Coulter) in a 15 mL Falcon tube. The tube is vortexed for 10 seconds and the solution is placed in a 20 mL cuvette (Accuvette) and placed into the instrument. Parameters are set to count particles between two and six µm. Results include particle concentration and size distribution of the particle population. The beads must be at least 80% monomeric to be of adequate quality for use in Simoa assays.

Detector Antibody Biotinylation

Approximately 100 µg of antibody is buffer exchanged into 1×PBS using 0.5 mL Amicon Ultra centrifugal filter unit (Millipore). The concentration of antibody is measured using a Nanodrop ND-1000 instrument (Nanodrop). A single, two mg vial of EZ-Link NHS-PEG$_4$-Biotin, no-weigh format (Thermo Scientific) is reconstituted in water. A working dilution was made in water and added to the tube of antibody at a 20× molar excess, 2.5% by volume. The antibody and biotin mixture is pipet mixed and allowed to incubate at room temperature for 30 minutes. After this incubation another 0.5 mL Amicon Ultra centrifugal filter unit (Millipore) is used to remove the excess unreacted biotin and buffer exchange the remaining antibody into fresh 1×PBS. The final concentration of the antibody is measured using a Nanodrop ND-1000 instrument (Nanodrop). The final product is stored at 4° C. for short term storage, and −20° C. for long term storage.

Reagent Preparation for HD-1 Assays

Capture antibody conjugated beads are diluted in Bead Diluent Buffer (Quanterix) to a concentration of $5 \times 10^6$ beads/mL in a 15 mL bottle (Quanterix). For multiplex assays (with at least three plexes), the total number of beads is increased to $6 \times 10^6$, but is split evenly between the number of plexes (e.g. $6 \times 10^6$ beads/mL divided by four plexes is $1.5 \times 10^6$ beads/mL). The appropriate volume was determined by multiplying the number of samples by 110 µL and adding 0.6 mL to account for dead volume in the bottle. The bead calculation requires 35 µL per sample of a $2 \times 10^7$ beads/mL solution.

Biotinylated detection antibody is diluted to a working concentration in Detector & Sample Diluent (Quanterix). Two-step assays typically require a working concentration of 1 µg/mL. The appropriate volume for a two-step assay is determined by multiplying the number of samples by 35 µL and adding the 0.6 mL dead volume. Streptavidin-β-galactosidase enzyme (SBG, Quanterix) is diluted to a concentration of 100-200 pM in SBG Diluent (Quanterix), depending on the individual assay. The appropriate volume is calculated in the same manner as the capture beads. The beads are placed in a Hulamixer rotator (Thermo Scientific) at 35 rpm for 10-15 minutes to prevent the beads from settling, and all reagents bottles are loaded into the reagent bay of the Simoa HD-1 Analyzer (Quanterix). The RGP substrate (Quanterix) is supplied by the manufacturer and used at a concentration of 100 µM.

Calibration and Sample Preparation

Calibrators are prepared by diluting protein stock into a standard diluent (1 XPBS/1% BSA or 25% newborn calf serum in PBS, 5 mM EDTA, 0.01% Tween 20, and ProClin 300, depending on the assay) to appropriate concentrations. Serum samples are prepared by pipetting into a 96-well round-bottom plate (VWR). If the HD-1 Analyzer has been programmed to dilute the samples by a factor of four, the serum would be pipetted neat, with a volume of 25 µL per replicate plus the dead volume (75 µL previously, 30 µL after the v1.5 software upgrade). If diluting offline, 100 µL of serum would be diluted in 300 µL of appropriate sample diluent in the plate. The plate wells have a maximum volume capacity of 450 µL.

HD-1 Procedure

For a two-step assay, 100 µL of $5 \times 10^6$ beads/mL bead solution is pipetted into a cuvette. The cuvette is held against a magnet to pellet the beads while the bead diluent is aspirated from the cuvette. 100 µL of sample is deposited into the cuvette, as well as 20 µL of detection antibody. This first shaking incubation lasts 35 minutes, followed by three washes with System Wash Buffer 1. 100 µL of SBG enzyme solution is then added to the cuvette and allowed to incubate for five minutes, followed by five washes with System Wash Buffer 1 and one wash with System Wash Buffer 2. After this last wash, 25 µL of the RGP substrate solution is added to the beads to resuspend them and 15 µL of this solution is loaded onto the Simoa HD-1 disc array and sealed with fluorocarbon oil (Krytox®, Dupont).

Image Acquisition

The HD-1 Analyzer (Quanterix) is equipped with a CCD camera that takes images of the arrays over a 45-second time period. The images are taken in different excitation/emission fluorescence channels in the following order: (1) 622/615 nm "dark field image", (2) 574/615 nm (resorufin), (3) 740/800 nm, (4) 680/720 nm, (5) 622/667 nm, (6) 574/615 nm, and (7) 490/530 nm. (1) establishes the position of the array to create a "well mask" for the other images, (2) and (4) image the fluorescence intensity of the product of the enzymatic reaction, (3)-(5) decode the identity of any dye-encoded beads, and (7) is used to decode the level of fluorescence in AF488-encoded beads and locate the position of all beads in the array.

Data Analysis

The array images are analyzed and decoded based on activity and bead type. A bead is considered "on" or "active" if fluorescence intensity of the well increases above a known threshold in the 30 seconds between the first and second resorufin channel images. The bead type or plex is determined by the presence and fluorescence intensity of the bead in a particular channel, which confirms bead identity.

The calibration AEB values extracted from the imaging data are fit to a four-parameter logistic curve with a $1/y^2$ weighting. The protein concentration of each sample is calculated using the fit equation of the generated curve. The LOD of the assay is determined by adding three standard deviations to the average signal generated by the blank, and using this signal value in the curve fit equation to calculate the concentration limit.

Three-Plex Assay

The three-plex assay was comprised of the ER, PR, and CYR61 reagents, with 700, 750, and 488 dye encoding, respectively. The antibodies and standards for all three assays were obtained from R&D Systems Duoset products (DYC5715, DYC5415, and DY4055). The assay format was a standard two-step procedure with a working concentration of $2 \times 10^6$ beads/mL per assay plex, for a total bead concentration of $6 \times 10^6$ beads/mL. The detector antibody working stock concentration was kept at 1 µg/mL per plex, and the enzyme concentration was 240 pM.

CA 15-3 and CDKN2D Two-Plex Assay

The CA 15-3 and CDKN2D two-plex assay was a standard two-step assay that was 488 and 750 dye encoded. The CA 15-3 assay reagents were obtained from Fitzgerald (10-CA15C, 10-CA15B, 30-AC17), with a bead concentration of $2.5 \times 10^6$ bead/mL, 3 µg/mL working stock detector concentration, and 200 pM enzyme. The CDKN2D capture antibody was obtained from Lifespan Biosciences (LS-C37972), the detector was from Abnova (H00001032-D01P), and the standard was from Origene (TB14065). The bead concentration was $2.5 \times 10^6$ bead/mL, 1 µg/mL working stock detector concentration, and 200 pM enzyme concentration.

HER2 and VEGF 2-Plex Assay

The HER2 and VEGF 2-plex assay was a standard two-step format with 488 and 700 dye encoding. HER2 reagents were purchased from R&D Systems, with the capture antibody and standard from a kit (DYC1129), and the detector antibody was purchased separately (BAF1129). The bead concentration was $2.5 \times 10^6$ beads/mL, with a detector antibody working stock concentration of 1 µg/mL, and an enzyme concentration of 25 pM. The VEGF assay capture antibody was obtained from Life Technologies (M808), and the standard and detector antibody were from R&D Systems (DY293B-05 and BAF293). The bead concentration was $2.5 \times 10^6$ beads/mL, with a detector antibody working stock concentration of 2 µg/mL, and an enzyme concentration of 25 pM.

CA 19-9 Assay

The CA 19-9 assay was run as a two-step singleplex assay on unencoded beads, with a bead concentration of $5 \times 10^6$/mL. CA 19-9 antibodies and standard were purchased from Fitzgerald, Inc (10-CA9B, 10-CA19A, 30-AC14S). The capture antibody was coupled to the magnetic beads and the detection antibody was biotinylated as previously described. The detection antibody was kept at a concentration of 2 µg/mL and SβG at a concentration of 100 pM.

Data Analysis

The protein standards and serum samples tested in this chapter were all diluted in 25% newborn calf serum PBS-based buffer. The serum samples tested by the HER2 and VEGF assays were manually diluted by a factor of six, while all other assay dilutions were by a factor of 8 before being placed in the HD-1 Analyzer (Quanterix).

Calibration curve fitting was performed the HD-1 Analyzer software (Stratec) using a 4PL equation, which was then used to calculate the protein concentrations in samples. Sample concentrations were corrected for the assay's dilution factor. The assay limit of detection was determined by adding three standard deviations of the blank measurement to the average blank signal, and using this value in the curve fitting formula to interpolate the LOD concentration. Statistical analysis of the single markers was performed using Prism 7 (Graphpad), and all multivariate analysis of the healthy and breast cancer serum data was done using a Matlab add-on software called PLS Toolbox v8.0.2 (Eigenvector).

Data was treated by first by replacing all undetectable samples with a value equal to half of the LOD of the assay, and multiplied by the dilution factor to minimally bias the model. Any missing data points were imputed by the software using the model as a template. The data was then autoscaled by the software and into the model. Cross validation was performed by splitting the data into five equal portions by way of random subsets, using 80% of the data for the calibration model, and the remaining 20% was used for validation. This was repeated until every portion of the data had been used for validation, then repeated five times. The sensitivity, specificity, precision, and accuracy values reported for each model were calculated from the confusion matrix generated from the PLS-DA classification.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A composition consisting of eight capture antibodies, each specifically binding to a different protein selected from the group consisting of Cancer Antigen (CA) 15-3 as set forth in SEQ ID NO: 1, CA 19-9 as set forth in SEQ ID NO: 3, Cyclin Dependent Kinase Inhibitor 2D (CDKN2D) as set forth in SEQ ID NO: 6, cysteine rich angiogenic inducer 61 (CYR61) as set forth in SEQ ID NO: 4, Estrogen Receptor (ER) alpha as set forth in SEQ ID NO: 8, Human Epidermal Growth Factor Receptor 2 (HER2) as set forth in SEQ ID NO: 10, progesterone receptor (PR) as set forth in SEQ ID NO: 12, and Vascular endothelial growth factor (VEGF) as set forth in SEQ ID NO: 14, wherein each of the eight capture antibodies is covalently conjugated to a substrate comprising a plurality of dye-conjugated paramagnetic carboxylated beads that are at least 80% monomeric, wherein each or a combination of one, two or three of the eight antibodies is covalently conjugated to the same bead to form one or more sets of beads in the plurality, wherein each set of beads comprises two, three, four or more fluorescent dyes, which provide unique identifiers for the bead set, and wherein the composition panel is capable of simultaneously capturing the eight proteins consisting of CA15-3 of SEQ ID NO: 1, CA 19-9 of SEQ ID NO: 3, CDKN2D of SEQ ID NO: 6, CYR61 of SEQ ID NO: 4, ER of SEQ ID NO: 8, HER2 of SEQ ID NO: 10, PR of SEQ ID NO: 12, and VEGF of SEQ ID NO: 14, from a serum or plasma biological sample obtained from a stage 0 or stage 1 breast cancer patient, in a single plex or multiplex assay for detection and quantification.

2. The composition of claim 1, wherein the bead is between about 2 and 3 µm in diameter.

3. The composition of claim 1, wherein the composition is present in suspension in a solution.

4. The composition of claim 1, wherein the sets of beads consist of a combination of a first set of beads, wherein each bead is covalently conjugated with three capture antibodies, each capture antibody specific to a different protein from the proteins of claim 1 and selected from the group consisting of ER, PR, and CYR61; a second set of beads, wherein each bead is covalently conjugated with two capture antibodies, each capture antibody specific to a different protein from the proteins of claim 1 and selected from the group consisting of CA 15-3 and CDKN2D; a third set of beads, wherein each bead is covalently conjugated with two capture antibodies, each capture antibody specific to a different protein from the proteins of claim 1 and selected from the group consisting of HER2, and VEGF; and a fourth set of beads, wherein each bead is covalently conjugated with a capture antibody specific to CA 19-9.

* * * * *